(12) United States Patent
Yagyu et al.

(10) Patent No.: US 12,100,434 B2
(45) Date of Patent: *Sep. 24, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventors: Daisuke Yagyu, Ichihara (JP); Tsuyoshi Kato, Ichihara (JP); Ayano Asano, Ichihara (JP); Natsumi Shibata, Ichihara (JP); Naoya Fukumoto, Ichihara (JP)

(73) Assignee: Resonac Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/797,177

(22) PCT Filed: Feb. 2, 2021

(86) PCT No.: PCT/JP2021/003708
§ 371 (c)(1),
(2) Date: Aug. 3, 2022

(87) PCT Pub. No.: WO2021/157563
PCT Pub. Date: Aug. 12, 2021

(65) Prior Publication Data
US 2023/0115042 A1    Apr. 13, 2023

(30) Foreign Application Priority Data

Feb. 7, 2020   (JP) .............. JP2020-020180

(51) Int. Cl.
*G11B 5/725*   (2006.01)
*C07D 303/28*  (2006.01)
(Continued)

(52) U.S. Cl.
CPC .......... *G11B 5/7257* (2020.08); *C07D 303/28* (2013.01); *C07D 309/12* (2013.01);
(Continued)

(58) Field of Classification Search
CPC . G11B 5/7257; C10M 107/38; C10M 105/54; C10M 105/70; C10M 105/72;
(Continued)

(56) References Cited

U.S. PATENT DOCUMENTS 4,360,645 A   11/1982   Krespan et al.
4,526,833 A   7/1985    Burguette et al.
(Continued)

FOREIGN PATENT DOCUMENTS

CN   1705698 A    12/2005
CN   101121908 A  2/2008
(Continued)

OTHER PUBLICATIONS

English abstract of WO 2019/054148, Japan, Mar. 2019, pp. 1-5 (Year: 2019).*

(Continued)

*Primary Examiner* — Holly Rickman
(74) *Attorney, Agent, or Firm* — Sughrue Mion, PLLC

(57) ABSTRACT

A fluorine-containing ether compound represented by a formula (1) shown below.

$$R^1-(O(CH_2)_a)_b-[A]-[B]-O-CH_2-R^2-CH_2-R^3 \quad (1)$$

(In the formula (1), $R^1$ is an alkyl group which may have a substituent, or an organic group having at least one double bond or triple bond. Further, a represents an integer of 2 to 4, and b is 0 or 1. [A] is represented by a formula (2): $-(OCH_2CH(OH)CH_2)_c-$ (wherein c is 1 or 2). [B] is represented by a formula (3): $-(O(CH_2)_eCH(OH)CH_2)_d-$ (wherein d is 0 or 1, and e represents an integer of 2 to 4).

(Continued)

However, the sum of c in the formula (2) and d in the formula (3) is 2. $R^2$ is a perfluoropolyether chain. $R^3$ is represented by a formula (4): —(OCH$_2$CH(OH)CH$_2$)$_2$—O—CH$_2$(CH$_2$)$_f$OH (wherein f represents an integer of 2 to 5).

11 Claims, 1 Drawing Sheet

(51) Int. Cl.
| | |
|---|---|
| C07D 309/12 | (2006.01) |
| C07D 405/12 | (2006.01) |
| C07D 407/12 | (2006.01) |
| C07D 409/12 | (2006.01) |
| C10M 105/54 | (2006.01) |
| C10M 105/70 | (2006.01) |
| C10M 105/72 | (2006.01) |
| C10N 20/04 | (2006.01) |
| C10N 40/18 | (2006.01) |

(52) U.S. Cl.
CPC ......... *C07D 405/12* (2013.01); *C07D 407/12* (2013.01); *C07D 409/12* (2013.01); *C10M 105/54* (2013.01); *C10M 105/70* (2013.01); *C10M 105/72* (2013.01); *C10M 2211/0425* (2013.01); *C10M 2215/305* (2013.01); *C10M 2219/102* (2013.01); *C10N 2020/04* (2013.01); *C10N 2040/18* (2013.01)

(58) Field of Classification Search
CPC .... C10M 2211/0425; C10M 2215/305; C10M 2219/102; C10M 2213/043; C10N 2040/18; C10N 2020/04; C10N 2030/06; C10N 2050/025; C07D 303/28; C07D 309/12; C07D 405/12; C07D 407/12; C07D 409/12; C07C 43/13; C07C 43/178; C07C 43/23; C07C 255/13; C07C 255/50

See application file for complete search history.

(56) References Cited

U.S. PATENT DOCUMENTS

| | | | |
|---|---|---|---|
| 5,157,066 A | 10/1992 | Shoji et al. | |
| 5,221,494 A | 6/1993 | Ikeda et al. | |
| 5,604,032 A | 2/1997 | Kai et al. | |
| 5,959,058 A | 9/1999 | Tonelli et al. | |
| 6,323,163 B1 | 11/2001 | Sasaki et al. | |
| 10,803,898 B2 | 10/2020 | Fukumoto et al. | |
| 11,011,200 B2 | 5/2021 | Uetake et al. | |
| 11,220,649 B2 | 1/2022 | Fukumoto et al. | |
| 11,225,624 B2 | 1/2022 | Kato et al. | |
| 11,261,394 B2 * | 3/2022 | Kato | C10M 107/38 |
| 11,279,664 B2 * | 3/2022 | Yagyu | C07C 43/23 |
| 11,427,779 B2 | 8/2022 | Yamaguchi et al. | |
| 11,639,330 B2 * | 5/2023 | Nanko | C07C 255/19 428/848 |
| 2004/0235685 A1 | 11/2004 | Russo et al. | |
| 2005/0123855 A1 | 6/2005 | Hegel | |
| 2005/0197408 A1 | 9/2005 | Shirakawa et al. | |
| 2006/0111251 A1 | 5/2006 | Tonelli et al. | |
| 2009/0281250 A1 | 11/2009 | Desimone et al. | |
| 2010/0233513 A1 | 9/2010 | Imai et al. | |
| 2010/0261039 A1 | 10/2010 | Itoh et al. | |
| 2012/0008228 A1 | 1/2012 | Mabuchi et al. | |
| 2012/0225217 A1 | 9/2012 | Itoh et al. | |
| 2012/0231297 A1 | 9/2012 | Sugiura et al. | |
| 2013/0209837 A1 | 8/2013 | Sagata et al. | |
| 2015/0274960 A1 | 10/2015 | Fukuda et al. | |
| 2015/0371672 A1 | 12/2015 | Sagata | |
| 2016/0068778 A1 | 3/2016 | Conley et al. | |
| 2016/0203839 A1 | 7/2016 | Shimizu | |
| 2017/0152456 A1 | 6/2017 | Sagata et al. | |
| 2017/0260472 A1 | 9/2017 | Sagata et al. | |
| 2017/0331155 A1 | 11/2017 | Yang et al. | |
| 2018/0009773 A1 | 1/2018 | Uetake et al. | |
| 2018/0022851 A1 | 1/2018 | Takao et al. | |
| 2018/0047419 A1 | 2/2018 | Fukumoto et al. | |
| 2018/0127543 A1 | 5/2018 | Watanabe et al. | |
| 2019/0084911 A1 | 3/2019 | Yagyu et al. | |
| 2019/0185621 A1 | 6/2019 | Naitou et al. | |
| 2019/0352573 A1 | 11/2019 | Hatta et al. | |
| 2019/0382675 A1 | 12/2019 | Fukumoto et al. | |
| 2019/0382676 A1 | 12/2019 | Yamaguchi et al. | |
| 2020/0010619 A1 | 1/2020 | Minami et al. | |
| 2021/0062101 A1 | 3/2021 | Kato et al. | |
| 2021/0062102 A1 | 3/2021 | Kato et al. | |
| 2021/0155751 A1 | 5/2021 | Kato | |
| 2021/0188766 A1 | 6/2021 | Nanko et al. | |
| 2022/0169941 A1 * | 6/2022 | Shibata | C08G 65/331 |
| 2022/0372390 A1 * | 11/2022 | Asano | C07C 217/28 |
| 2023/0090239 A1 * | 3/2023 | Nanko | C08G 65/3312 428/835.8 |

FOREIGN PATENT DOCUMENTS

| | | |
|---|---|---|
| CN | 102639477 A | 8/2012 |
| CN | 107849235 A | 3/2018 |
| CN | 114341094 A | 4/2022 |
| CN | 114599631 A | 6/2022 |
| EP | 1 479 753 A2 | 11/2004 |
| EP | 3 081 549 A1 | 10/2016 |
| JP | 57-176973 A | 10/1982 |
| JP | 61-126052 A | 6/1986 |
| JP | 3-7798 A | 1/1991 |
| JP | 5-12655 A | 1/1993 |
| JP | 8-259882 A | 10/1996 |
| JP | 10-106822 A | 4/1998 |
| JP | 11-60720 A | 3/1999 |
| JP | 11-71440 A | 3/1999 |
| JP | 2866622 B2 | 3/1999 |
| JP | 11-131083 A | 5/1999 |
| JP | 2000-264883 A | 9/2000 |
| JP | 2001-134924 A | 5/2001 |
| JP | 2001-209924 A | 8/2001 |
| JP | 2002-69037 A | 3/2002 |
| JP | 2003-113389 A | 4/2003 |
| JP | 2004-115640 A | 4/2004 |
| JP | 2004-346318 A | 12/2004 |
| JP | 2006-131874 A | 5/2006 |
| JP | 2009-266360 A | 11/2009 |
| JP | 2010-143855 A | 7/2010 |
| JP | 2010-241831 A | 10/2010 |
| JP | 2010-282707 A | 12/2010 |
| JP | 4632144 B2 | 2/2011 |
| JP | 2012-9090 A | 1/2012 |
| JP | 2012-33253 A | 2/2012 |
| JP | 2013-163667 A | 8/2013 |
| JP | 2013-181014 A | 9/2013 |
| JP | 2013-181140 A | 9/2013 |
| JP | 2014-509677 A | 4/2014 |
| JP | 5465454 B2 | 4/2014 |
| JP | 5613916 B2 | 10/2014 |
| JP | 5909837 B2 | 4/2016 |
| JP | 6122191 B1 | 4/2017 |
| JP | 2018-002673 A | 1/2018 |
| JP | 2018-024614 A | 2/2018 |
| JP | 2018-035348 A | 3/2018 |
| JP | 2018-076404 A | 5/2018 |
| JP | 2018-521183 A | 8/2018 |
| JP | 2018-178079 A | 11/2018 |
| WO | 98/17617 A1 | 4/1998 |
| WO | 2006/011387 A1 | 2/2006 |
| WO | 2009/035075 A1 | 3/2009 |
| WO | 2009/123043 A1 | 10/2009 |
| WO | 2011/099131 A1 | 8/2011 |
| WO | 2012/170009 A2 | 12/2012 |
| WO | 2015/087615 A1 | 6/2015 |
| WO | 2015/199037 A1 | 12/2015 |

(56) References Cited

FOREIGN PATENT DOCUMENTS

| | | |
|---|---|---|
| WO | 2016/084781 A1 | 6/2016 |
| WO | 2017/005834 A1 | 1/2017 |
| WO | 2017/145995 A1 | 8/2017 |
| WO | 2017/154403 A1 | 9/2017 |
| WO | 2018/116742 A1 | 6/2018 |
| WO | 2018/139058 A1 | 8/2018 |
| WO | 2018/139174 A1 | 8/2018 |
| WO | 2018/147017 A1 | 8/2018 |
| WO | 2018/159232 A1 | 9/2018 |
| WO | 2019/039200 A1 | 2/2019 |
| WO | 2019/039265 A1 | 2/2019 |
| WO | 2019/049585 A1 | 3/2019 |
| WO | 2019/054148 A1 | 3/2019 |
| WO | 2019/087548 A1 | 5/2019 |

OTHER PUBLICATIONS

English abstract of WO2019/039200, Japan, Feb. 2019, pp. 1-4 (Year: 2019).*
International Search Report for PCT/JP2021/003708 dated Mar. 23, 2021.
Non-Final Office Action dated Apr. 26, 2023 in U.S. Appl. No. 17/788,075.
R.J. Waltman, "Z-Tetraol composition and bonding to the underlying carbon surface", Journal of Colloid and Interface Science, 2009, vol. 333, pp. 540-547 (8 pages total).
International Search Report for PCT/JP2020/047987, dated Feb. 16, 2021.
International Search Report of PCT/JP2018/028455 dated Oct. 2, 2018.
First Office Action dated May 7, 2022 issued by the Chinese Patent Office in Chinese Application No. 201880053594.9.
Non-Final Office Action dated Sep. 15, 2022 in U.S. Appl. No. 16/640,132.
Notice of Allowance dated Jan. 5, 2023 in U.S. Appl. No. 16/640,132.
International Search Report for PCT/JP2020/041613, dated Dec. 28, 2020.
Office Action issued May 24, 2023 in U.S. Appl. No. 17/772,043.
"Cihai Sciences vol. 1" Edited by Cihai Editorial Committee, Shanghai Lexicographical Publishing House, Aug. 30, 1980, p. 329 (3 pages total).
Advisory Action dated Aug. 11, 2021, issued in U.S. Appl. No. 16/480,464.
Communication dated Dec. 24, 2019, from the Japanese Patent Office in Application No. 2016-133653.
International Search Report for PCT/JP2017/003165 dated May 9, 2017.
International Search Report for PCT/JP2017/043451 dated Feb. 27, 2018 [PCT/ISA/210].
International Search Report for PCT/JP2018/031161, dated Nov. 27, 2018 (PCT/ISA/210).
International Search Report for PCT/JP2019/033697 dated Nov. 5, 2019.
International Search Report for PCT/JP2019/033700 dated Nov. 12, 2019 [PCT/ISA/210].
International Search Report for PCT/JP2020/033971 dated Nov. 24, 2020 [PCT/ISA/210].
Notice of Allowance Dated Sep. 10, 2021 issued in U.S. Appl. No. 16/480,464.
Notice of Allowance dated Feb. 8, 2021 from the US Patent & Trademark Office in U.S. Appl. No. 15/640,729.
Notice of Allowance dated Nov. 16, 2021 from the US & Patent & Trademark Office in U.S. Appl. No. 16/082,349.
Notice of Allowance issued May 5, 2022 in U.S. Appl. No. 16/480,483.
Notice of Allowance issued Nov. 9, 2021 in U.S. Appl. No. 16/644,586.
Office Action dated Dec. 2, 2020 from the China National Intellectual Property Administration in CN Application No. 201780012469.9.
Office Action dated Jun. 10, 2019 from the US & Patent & Trademark Office in U.S. Appl. No. 15/640,729.
Office Action dated Jun. 8, 2021 from the US & Patent & Trademark Office in U.S. Appl. No. 16/082,349.
Office Action dated Mar. 11, 2021 from the China National Intellectual Property Administration in CN Application No. 201780070908.1.
Office Action dated Mar. 4, 2021 from the US & Patent & Trademark Office in U.S. Appl. No. 15/640,729.
Office Action dated May 13, 2020 from the US & Patent & Trademark Office in U.S. Appl. No. 15/640,729.
Office Action dated May 25, 2021 from the China National Intellectual Property Administration in CN Application No. 201780012469.9.
Office Action dated Nov. 12, 2020 from the US & Patent & Trademark Office in U.S. Appl. No. 15/640,729.
Office Action dated Oct. 29, 2019 from the US & Patent & Trademark Office in U.S. Appl. No. 15/640,729.
Office Action Final Dated Apr. 16, 2021 Issued in U.S. Appl. No. 16/480,464.
Office Action issued Dec. 21, 2022 in U.S. Appl. No. 17/274,466.
Office Action issued Jan. 19, 2022 in U.S. Appl. No. 16/480,483.
Office Action issued Jul. 23, 2021 in U.S. Appl. No. 16/644,586.
Office Action issued Oct. 25, 2022 in U.S. Appl. No. 17/274,702.
Office Action Non-Final dated Jan. 28, 2021, issued in U.S. Appl. No. 16/480,464.
Restriction Election Requirement dated Nov. 23, 2020, issued in U.S. Appl. No. 16/480,464.
Supplemental Notice of Allowance issued Dec. 2, 2021 in U.S. Appl. No. 16/644,586.
Office Action issued Jan. 19, 2023 in U.S. Appl. No. 17/437,251.
International Search Report of PCT/JP2020/010759 dated May 26, 2020 [PCT/ISA/21 0].
International Search Report for PCT/JP2018/000071 dated Mar. 6, 2018 [PCT/ISA/210].
Office Action issued Jun. 21, 2021 in U.S. Appl. No. 16/480,483.
Notice of Allowance issued Feb. 9, 2023 in U.S. Appl. No. 17/274,702.
Paul H. Kasai et al., "Perfluoropolyethers with dialkylamine end groups: ultrastable lubricant for magnetic disk application", Tribology Letters, Feb. 2002, vol. 12, No. 2, pp. 117-122 (6 pages total).

* cited by examiner

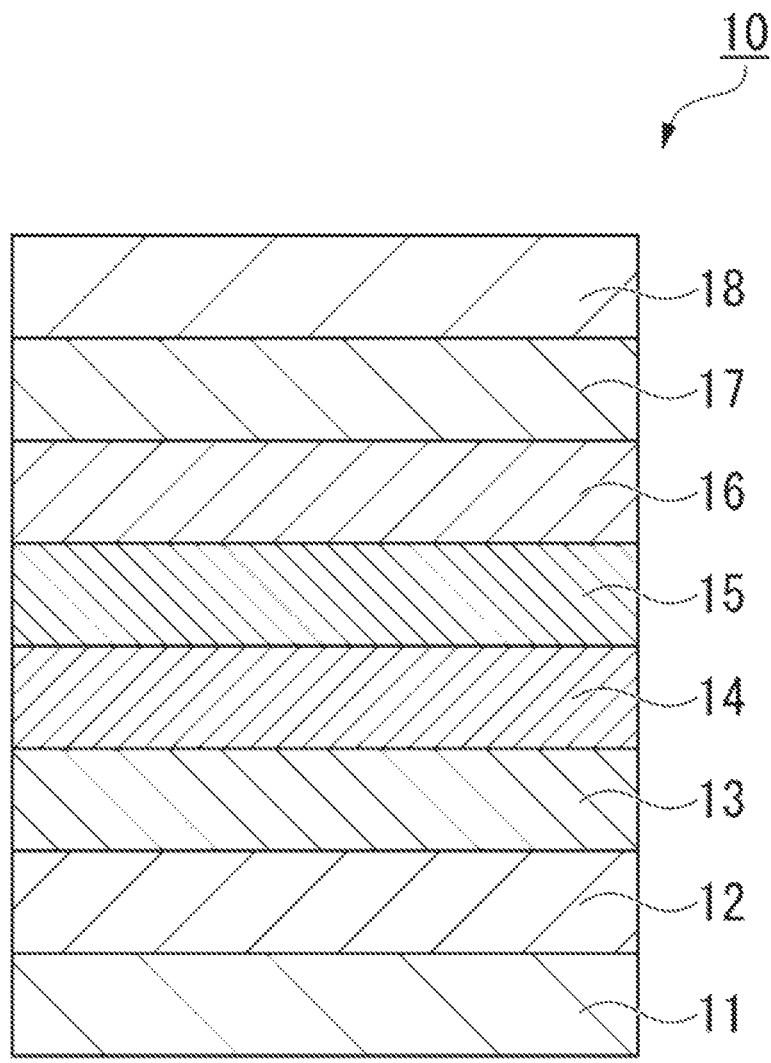

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2021/003708 filed Feb. 2, 2021, claiming priority based on Japanese Patent Application No. 2020-020180 filed Feb. 7, 2020, the content of which is incorporated herein by reference.

TECHNICAL FIELD

The present invention relates to a fluorine-containing ether compound that is suitable for lubricant applications in magnetic recording media, and a magnetic recording medium lubricant and a magnetic recording medium that include the fluorine-containing ether compound.

BACKGROUND ART

In recent years, with the volume of information processing through the internet increasing dramatically, much attention has become focused on the development of recording media for storing that information. Magnetic recording media, which represent one type of recording media, enable large-volume storage at low cost, and are anticipated to act as a particularly important receptacle for this ever increasing information.

In a magnetic recording medium, in order to ensure favorable durability and reliability for the magnetic recording medium, a protective layer and a lubricant layer are provided on top of the magnetic layer (magnetic recording layer) that is formed on top of the substrate. The lubricant layer, which is disposed on the outermost surface, requires particularly favorable levels of a variety of characteristics such as long-term stability, chemical substance resistance (to prevent contamination from siloxanes and the like), wear resistance, and heat resistance.

Examples of lubricants that have been proposed for magnetic recording media include lubricants containing a compound composed of a fluorine-based polymer having a repeating structure containing $CF_2$ and having polar groups such as hydroxyl groups at the polymer terminals (for example, see Patent Documents 1 to 7).

Specifically, Patent Document 1 discloses a compound having a plurality of hydroxyl groups at both terminal portions of a fluorine-based polymer, wherein the closest distance between hydroxyl groups is at least a 3-atom spacing.

Patent Document 2 discloses a fluoropolyether compound having an aromatic group at one terminal of a fluorine-based polymer, and having a hydroxyl group at the other terminal.

Patent Document 3 discloses a compound having a perfluoropolyether main chain, wherein a terminal group of the molecule has an aromatic group and a hydroxyl group, and the aromatic group and the hydroxyl group are bonded to different carbon atoms.

Patent Document 4 discloses a fluorine-containing ether compound having a perfluoropolyether chain. At one terminal of this perfluoropolyether chain, a terminal group containing an organic group having at least one double bond or triple bond is bonded via a divalent linking group that is bonded via an etheric oxygen. At the other terminal of the perfluoropolyether chain is a terminal group which contains two or three polar groups, wherein each of the polar groups is bonded to a different carbon atom, and the carbon atoms to which the polar groups are bonded are linked together by a linking group containing a carbon atom to which no polar group is bonded.

Patent Document 5 discloses a fluorine-containing ether compound having a perfluoropolyether chain. Both terminal groups of this fluorine-containing ether compound are composed of one of an alkyl group that may have a substituent, an organic group having at least one double bond or triple bond, and a hydrogen atom. Further, a linking group containing a hydroxyl group is disposed between the perfluoropolyether chain and each of the terminal groups.

Patent Document 6 discloses a fluorine-containing ether compound having a perfluoropolyether chain. At one terminal of the perfluoropolyether chain, an alkyl group that may have a substituent is bonded via a divalent linking group. At the other terminal of the perfluoropolyether chain is a terminal group which contains two or three polar groups, wherein each of the polar groups is bonded to a different carbon atom, and the carbon atoms to which the polar groups are bonded are linked together by a linking group containing a carbon atom to which no polar group is bonded.

Patent Document 7 discloses a fluorine-containing ether compound having a perfluoropolyether chain. At least one of the terminal groups of the fluorine-containing ether compound is a group composed of an organic group of 1 to 8 carbon atoms in which one or more hydrogen atoms have each been substituted with a cyano group. Further, a divalent linking group having a polar group is disposed between the perfluoropolyether chain and the terminal group.

PRIOR ART LITERATURE

Patent Documents

Patent Document 1: Japanese Patent (Granted) Publication No. 4632144
Patent Document 2: Japanese Patent (Granted) Publication No. 5909837
Patent Document 3: Japanese Patent (Granted) Publication No. 5465454
Patent Document 4: International Patent Publication No. 2017/154403
Patent Document 5: International Patent Publication No. 2019/054148
Patent Document 6: International Patent Publication No. 2019/049585
Patent Document 7: International Patent Publication No. 2019/039200

DISCLOSURE OF INVENTION

Problems to be Solved by the Invention

In order to increase the recording density of magnetic recording media to enable larger volume storage, it is necessary to reduce the magnetic spacing, which describes the distance between the magnetic head and the magnetic layer of the magnetic recording medium. Potential methods for reducing the magnetic spacing include lowering the floating height of the magnetic head, and reducing the thickness of the lubricant layer.

However, lowering the floating height of the magnetic head increases the likelihood of pickup, in which the fluorine-containing ether compound in the lubricant layer adheres to the magnetic head as foreign matter (smears).

In recent years, the rotational speed of magnetic recording media has increased. This has increased the likelihood of spin-off of the lubricant layer. Spin-off describes a phenomenon in which the lubricant can fly off or volatilize as a result of the centrifugal force that accompanies rotation of the magnetic recording medium or heating.

Reducing the average molecular weight of the lubricant enables a reduction in the thickness of the lubricant layer, but spin-off is more likely to occur in such cases.

The present invention has been developed in light of the above circumstances, and has an object of providing a fluorine-containing ether compound that can be used favorably as a material for a magnetic recording medium lubricant that is capable of forming a lubricant layer that can suppress pickup and spin-off, while being unaffected by the average molecular weight of the fluorine-containing ether compound in the lubricant.

Further, the present invention also has an object of providing a magnetic recording medium lubricant containing the fluorine-containing ether compound of the present invention.

Furthermore, the present invention also has an object of providing a magnetic recording medium having a lubricant layer containing the fluorine-containing ether compound of the present invention.

Means for Solving the Problems

The inventors of the present invention conducted intensive research aimed at achieving the above objects.

As a result, they discovered that by using a magnetic recording medium lubricant containing a fluorine-containing ether compound having a specific molecular structure, a lubricant layer could be formed that exhibited favorable adhesion with the protective layer, and was capable of suppressing pickup and spin-off even when the molecular weight was reduced, thus enabling them to complete the present invention.

In other words, the present invention relates to the following items.

[1] A fluorine-containing ether compound represented by a formula (1) shown below.

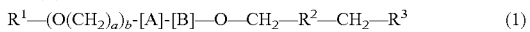

(In the formula (1), $R^1$ is an alkyl group which may have a substituent, or an organic group having at least one double bond or triple bond. Further, a represents an integer of 2 to 4, and b is 0 or 1. [A] is represented by a formula (2) shown below, and c in the formula (2) is 1 or 2. [B] is represented by a formula (3) shown below, wherein d in the formula (3) is 0 or 1, and e represents an integer of 2 to 4, provided that the sum of c in the formula (2) and d in the formula (3) is 2. $R^2$ is a perfluoropolyether chain. $R^3$ is represented by a formula (4) shown below, and f in the formula (4) represents an integer of 2 to 5.)

[Chemical formula 1]

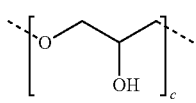

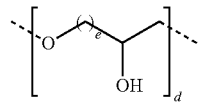

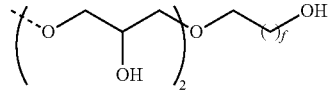

[2] The fluorine-containing ether compound according to [1], wherein the fluorine-containing ether compound has a number average molecular weight within a range from 1,000 to 2,300.

[3] The fluorine-containing ether compound according to [1] or [2], wherein $R^1$ in the formula (1) is an alkyl group of 1 to 6 carbon atoms.

[4] The fluorine-containing ether compound according to [1] or [2], wherein $R^1$ in the formula (1) is an alkyl group of 1 to 6 carbon atoms that has a substituent, and the substituent is a fluoro group or a cyano group.

[5] The fluorine-containing ether compound according to [1] or [2] wherein $R^1$ in the formula (1) is any one of an organic group of 6 to 12 carbon atoms containing an aromatic hydrocarbon, an organic group of 3 to 10 carbon atoms containing an aromatic heterocycle, an alkenyl group of 2 to 8 carbon atoms, and an alkynyl group of 3 to 8 carbon atoms.

[6] The fluorine-containing ether compound according to [1] or [2], wherein $R^1$ in the formula (1) is one group selected from a group consisting of a methyl group, ethyl group, n-propyl group, isopropyl group, 2,2,2-trifluoroethyl group, 2,2,3,3,3-pentafluoropropyl group, 2,2,2,2,2-hexafluoroisopropyl group, 2-cyanoethyl group, 3-cyanopropyl group, 4-cyanobutyl group, phenyl group, methoxyphenyl group, cyanophenyl group, phenethyl group, thienylethyl group, N-methylpyrazolylmethyl group, allyl group, 3-butenyl group, 4-pentenyl group, propargyl group, 3-butynyl group, and 4-pentynyl group.

[7] The fluorine-containing ether compound according to any one of [1] to [6], wherein $R^2$ in the formula (1) is represented by one of formulas (5) to (8) shown below.

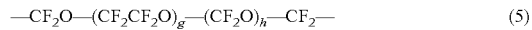

(In the formula (5), g and h indicate average polymerization degrees, wherein g represents a number from 3 to 8, and h represents a number from 3 to 8.)

(In the formula (6), i indicates an average polymerization degree, and represents a number from 5 to 13.)

(In the formula (7), j indicates an average polymerization degree, and represents a number from 3 to 8.)

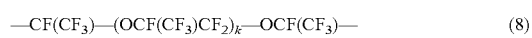

(in the formula (8), k indicates an average polymerization degree, and represents a number from 3 to 8.)

[8] The fluorine-containing ether compound according to [1], wherein the compound represented by the formula (1) is a compound represented by one of formulas (A1) to (A3), (B1) to (B3), (L1) and (M1) shown below.

[Chemical formula 2]

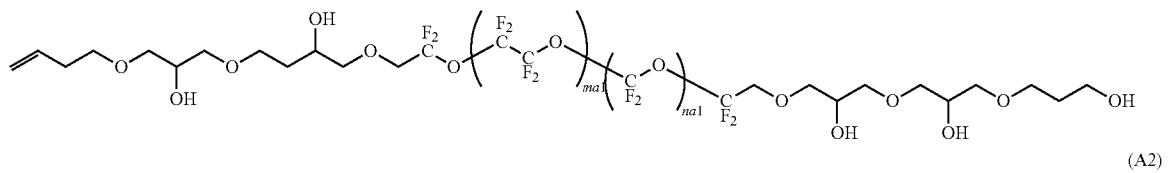
(A1)

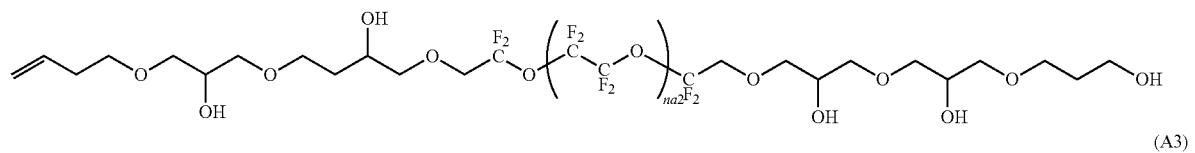
(A2)

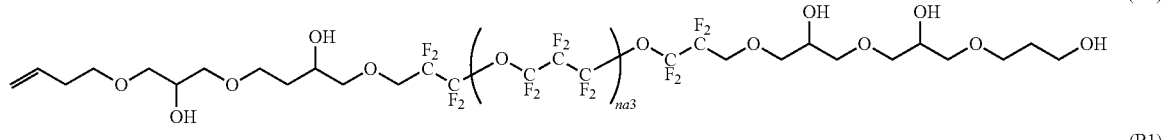
(A3)

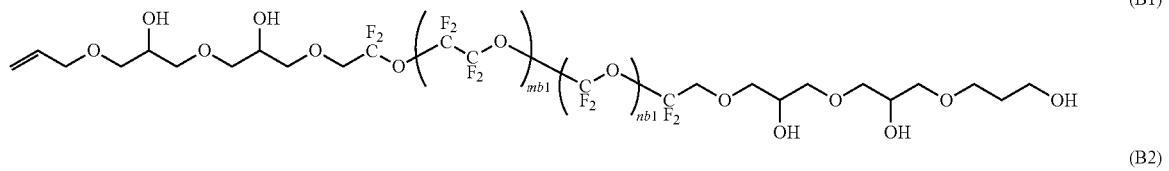
(B1)

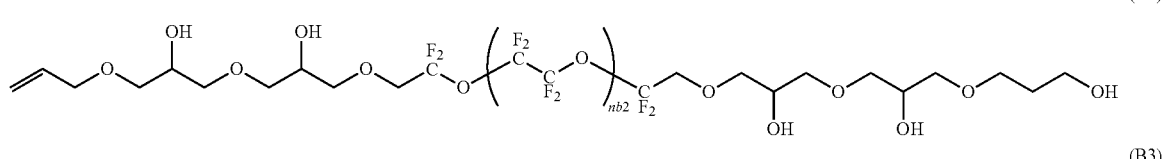
(B2)

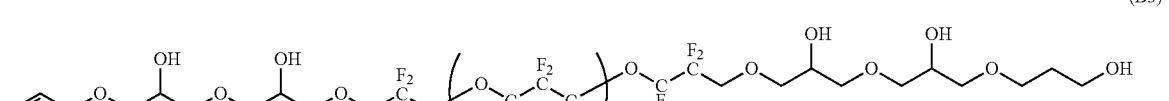
(B3)

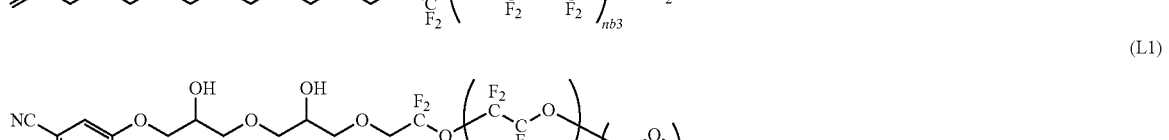
(L1)

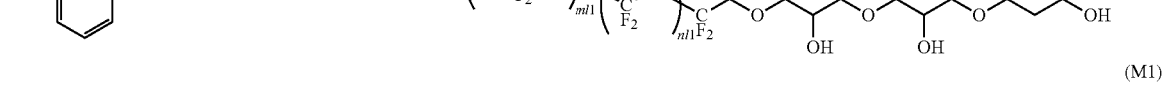
(M1)

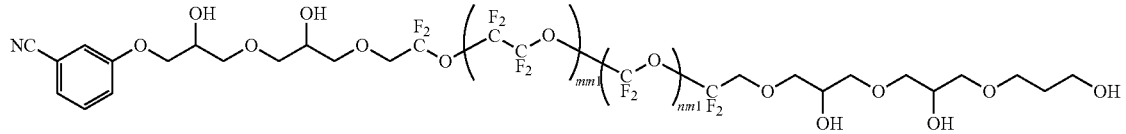

(In the formula (A1), ma1 and na1 indicate average polymerization degrees, wherein ma1 represents a number from 3 to 8, and na1 represents a number from 3 to 8.)

(In the formula (A2), na2 indicates an average polymerization degree, and represents a number from 5 to 13.)

(In the formula (A3), na3 indicates an average polymerization degree, and represents a number from 3 to 8.)

(In the formula (B1), mb1 and nb1 indicate average polymerization degrees, wherein mb1 represents a number from 3 to 8, and nb1 represents a number from 3 to 8.)

(In the formula (B2), nb2 indicates an average polymerization degree, and represents a number from 5 to 13.)

(In the formula (B3), nb3 indicates an average polymerization degree, and represents a number from 3 to 8.)

(In the formula (L1), ml1 and nl1 indicate average polymerization degrees, wherein ml1 represents a number from 3 to 8, and nl1 represents a number from 3 to 8.)

(In the formula (M1), mm1 and nm1 indicate average polymerization degrees, wherein mm1 represents a number from 3 to 8, and nm1 represents a number from 3 to 8.)

[9] A lubricant for a magnetic recording medium, the lubricant containing the fluorine-containing ether compound according to any one of [1] to [8].

[10] A magnetic recording medium containing at least a magnetic layer, a protective layer and a lubricant layer provided sequentially on a substrate, wherein the lubricant layer contains the fluorine-containing ether compound according to any one of [1] to [8].

[11] The magnetic recording medium according to [10], wherein the average thickness of the lubricant layer is within a range from 0.5 nm to 2.0 nm.

Effects of the Invention

The fluorine-containing ether compound of the present invention is a compound represented by the formula (I) shown above, and is ideal as a material for a lubricant for a magnetic recording medium.

The lubricant for a magnetic recording medium according to the present invention contains the fluorine-containing ether compound of the present invention. As a result, a lubricant layer can be formed that has good adhesion to the protective layer, and can suppress pickup and spin-off, while being unaffected by the average molecular weight of the fluorine-containing ether compound in the lubricant.

The magnetic recording medium of the present invention has a lubricant layer that has good adhesion to the protective layer, and can suppress pickup and spin-off.

BRIEF DESCRIPTION OF THE DRAWINGS

The FIGURE is a schematic cross-sectional view illustrating one embodiment of a magnetic recording medium of the present invention.

EMBODIMENTS FOR CARRYING OUT THE INVENTION

In order to achieve the objects described above, the inventors of the present invention focused their attention on the relationship between the protective layer and the molecular structure of the fluorine-containing ether compound contained in the lubricant layer, and conducted intensive research as outlined below.

The molecular structure of the fluorine-containing ether compound contained in the lubricant layer has a large effect on the thickness and adhesion characteristics of the lubricant layer.

Conventionally, in order to obtain a lubricant layer having favorable adhesion characteristics to the protective layer, a perfluoropolyether-based compound (hereafter sometimes referred to as a "PFPE-based compound") having a hydroxyl group within the molecule has been used as the lubricant. However, even in the case of a lubricant layer containing a PFPE-based compound having a plurality of hydroxyl groups within the molecule, satisfactory adhesion of the lubricant layer to the protective layer has sometimes been unattainable.

As a result of intensive investigation, the inventors of the present invention discovered that even in the case of a lubricant layer containing a PFPE-based compound having a plurality of hydroxyl groups, if the hydroxyl groups within the PFPE-based compound do not participate effectively in the bonding with the active sites on the protective layer, then satisfactory adhesion with the protective layer cannot be achieved.

Moreover, as a result of intensive investigation, the inventors of the present invention also discovered that if large numbers of hydroxyl groups that do not participate in the bonding with the active sites on the protective layer exist within the PFPE-based compound contained in the lubricant layer, then the following trends are observed. Namely, spin-off that causes a reduction in the lubricant tends to occur as a result of the lubricant flying off or volatilizing due to the centrifugal force during high-speed rotation or heating, and pickup in which the lubricant adheres to the magnetic head as foreign matter (smears) also tends to occur more readily.

Accordingly, the inventors of the present invention conducted research focused on the molecular structure of the fluorine-containing ether compound, with the aim of promoting bonding between the plurality of hydroxyl groups within the fluorine-containing ether compound and the active sites on the protective layer, thus enabling them to complete the present invention.

The fluorine-containing ether compound, the lubricant for a magnetic recording medium (hereafter sometimes abbreviated as simply "the lubricant"), and the magnetic recording medium according to the present invention are described below in detail. However, the present invention is not limited solely to the embodiments described below.

[Fluorine-Containing Ether Compound]

The fluorine-containing ether compound of an embodiment of the present invention is represented by a formula (1) shown below.

$$R^1—(O(CH_2)_a)_b-[A]-[B]—O—CH_2—R^2—CH_2—R^3 \quad (1)$$

(In the formula (1), $R^1$ is an alkyl group which may have a substituent, or an organic group having at least one double bond or triple bond. Further, a represents an integer of 2 to 4, and b is 0 or 1. [A] is represented by a formula (2) shown below, and c in the formula (2) is 1 or 2. [B] is represented by a formula (3) shown below, wherein d in the formula (3) is 0 or 1, and e represents an integer of 2 to 4, provided that the sum of c in the formula (2) and d in the formula (3) is 2. $R^2$ is a perfluoropolyether chain. $R^3$ is represented by a formula (4) shown below, and f in the formula (4) represents an integer of 2 to 5.)

[Chemical formula 3]

(2)

(3)

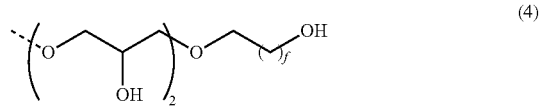

(4)

In the fluorine-containing ether compound represented by the formula (1), $R^1$ is a terminal group, and represents either an alkyl group which may have a substituent, or an organic group having at least one double bond or triple bond. The alkyl group which may have a substituent, and the organic group having at least one double bond or triple bond may also contain any of an oxygen atom, a sulfur atom, and a nitrogen atom.

$R^1$ may represent an alkyl group of 1 to 6 carbon atoms, or an alkyl group of 1 to 6 carbon atoms that has a substituent. Examples of the substituent include a fluoro group or a cyano group, and one or more of the hydrogen atoms of the alkyl group may be substituted. All of the hydrogen atoms of the alkyl group may also be substituted with substituents.

Further, the alkyl group of 1 to 6 carbon atoms, and the alkyl group of 1 to 6 carbon atoms that has a substituent may be either linear or branched.

Examples of the alkyl group of 1 to 6 carbon atoms include a methyl group, ethyl group, n-propyl group, isopropyl group, n-butyl group, sec-butyl group, isobutyl group, tert-butyl group, n-pentyl group and structural isomers thereof, and n-hexyl group and structural isomers thereof.

Examples of alkyl groups of 1 to 6 carbon atoms in which at least one hydrogen atom has been substituted with a fluoro group include a trifluoromethyl group, perfluoroethyl group, perfluoropropyl group, perfluorobutyl group, perfluoropentyl group, perfluorohexyl group, 2,2,2-trifluoroethyl group, 2,2,3,3,3-pentafluoropropyl group, 2,2,2,2,2,2-hexafluoroisopropyl group, 2,2,3,3,4,4,4-heptafluorobutyl group, 2,2,3,3,4,4,5,5,5-nonafluoropentyl group, and 2,2,3,3,4,4,5,5,6,6,6-undecafluorohexyl group.

In the alkyl groups of 1 to 6 carbon atoms in which at least one hydrogen atom has been substituted with a cyano group, the number of cyano groups may be either one, or two or more. If the number of cyano groups is too large, then the polarity of the fluorine-containing ether compound may become too high, and therefore the number of cyano groups is preferably not more than two, and is most preferably one.

Examples of alkyl groups of 1 to 6 carbon atoms in which at least one hydrogen atom has been substituted with a cyano group include a 2-cyanoethyl group, 3-cyanopropyl group, 4-cyanobutyl group, 5-cyanopentyl group, 6-cyanohexyl group, 2-cyano-1-methylethyl group, and 2,2'-dicyanoisopropyl group.

The organic group having at least one double bond or triple bond is preferably an organic group of 6 to 12 carbon atoms containing an aromatic hydrocarbon, an organic group of 3 to 10 carbon atoms containing an aromatic heterocycle, an alkenyl group of 2 to 8 carbon atoms, or an alkynyl group of 3 to 8 carbon atoms, and may be either a linear group or a branched group.

Examples of the organic group of 6 to 12 carbon atoms containing an aromatic hydrocarbon include a phenyl group, methoxyphenyl group, dimethoxyphenyl group, cyanophenyl group, dicyanophenyl group, fluorophenyl group, naphthyl group, methoxynaphthyl group, benzyl group, methoxybenzyl group, phenethyl group, methoxyphenethyl group, fluorophenethyl group, naphthylmethyl group, and naphthylethyl group. In those cases where the aromatic hydrocarbon has a substituent, the substituent position may be any position.

Examples of the organic group of 3 to 10 carbon atoms containing an aromatic heterocycle include a pyrrolyl group, pyrazolyl group, methylpyrazolylmethyl group, imidazolyl group, furyl group, furfuryl group, oxazolyl group, isoxazolyl group, thienyl group, thienylmethyl group, thienylethyl group, thiazolyl group, methylthiazolylethyl group, isothiazolyl group, pyridyl group, pyrimidinyl group, pyridazinyl group, pyrazinyl group, indolinyl group, benzofuranyl group, benzothienyl group, benzimidazolyl group, benzoxazolyl group, benzothiazolyl group, benzopyrazolyl group, benzisoxazolyl group, benzisothiazolyl group, quinolyl group, isoquinolyl group, quinazolinyl group, quinoxalinyl group, phthalazinyl group, and cinnolinyl group.

Examples of the alkenyl group of 2 to 8 carbon atoms include a vinyl group, allyl group, 1-propenyl group, isopropenyl group, 3-butenyl group and structural isomers thereof, 4-pentenyl group and structural isomers thereof, 5-hexenyl group and structural isomers thereof, 6-heptenyl group and structural isomers thereof, and 7-octenyl group and structural isomers thereof.

Examples of the alkynyl group of 3 to 8 carbon atoms include a 1-propynyl group, propargyl group, 3-butynyl group and structural isomers thereof, 4-pentynyl group and structural isomers thereof, 5-hexynyl group and structural isomers thereof, 6-heptynyl group and structural isomers thereof, and 7-octynyl group and structural isomers thereof.

From the viewpoints of availability and/or ease of synthesis, $R^1$ in the fluorine-containing ether compound represented by the formula (1) is preferably a methyl group, ethyl group, n-propyl group, isopropyl group, 2,2,2-trifluoroethyl group, 2,2,3,3,3-pentafluoropropyl group, 2,2,2,2,2,2-hexafluoroisopropyl group, 2-cyanoethyl group, 3-cyanopropyl group, 4-cyanobutyl group, phenyl group, methoxyphenyl group, cyanophenyl group, phenethyl group, thienylethyl group, N-methylpyrazolylmethyl group, allyl group, 3-butenyl group, 4-pentenyl group, propargyl group, 3-butynyl group, or 4-pentynyl group, and is most preferably a methyl group, ethyl group, n-propyl group, 2,2,2-trifluoroethyl group, 2,2,3,3,3-pentafluoropropyl group, 3-cyanopropyl group, 4-cyanobutyl group, methoxyphenyl group, cyanophenyl group, allyl group, or 3-butenyl group.

In the fluorine-containing ether compound of an embodiment of the present invention, a in the formula (1) represents an integer of 2 to 4. Further, b in the formula (1) is 0 or 1. In those cases where b is 0, an increase in the surface free energy of the overall molecule, due to a decrease in the proportion of fluorine atoms in the fluorine-containing ether compound molecule, can be suppressed.

In those cases where b is 1, the terminal group $R^1$ in the formula (1) and [A] represented by the formula (2) are linked via an ether bond, and this ether bond has the effect of imparting the fluorine-containing ether compound represented by the formula (1) with flexibility, thus facilitating adsorption to the protective layer. When b is 1, a is preferably an integer of 2 to 3, and is more preferably 2. In those cases where a is 2, an increase in the surface free energy of the overall molecule, due to a decrease in the proportion of fluorine atoms in the fluorine-containing ether compound molecule, can be suppressed.

If a is 1, then the molecule tends to be chemically unstable and prone to degradation, and therefore a is an integer of 2 to 4.

In the fluorine-containing ether compound represented by the formula (1), [A] and [B] are divalent linking groups represented by the formula (2) and formula (3) respectively. Formula (1) always includes two secondary hydroxyl groups within the combination of [A] and [B], and the carbon atoms to which the hydroxyl groups are bonded are linked via a linking group composed of a methylene group (—CH$_2$—) and an ether bond (—O—). Accordingly, the two hydroxyl groups contained within the -[A]-[B]— structure have an appropriate distance between hydroxyl groups. Moreover, as a result of also having etheric oxygen atoms, the -[A]-[B]— structure imparts an appropriate level of flexibility to the molecular structure of the fluorine-containing ether compound represented by the formula (1). For these reasons, when a lubricant layer containing the fluorine-containing ether compound of an embodiment of the present invention is formed on top of a protective layer, the two hydroxyl groups within the -[A]-[B]— structure can more readily participate in bonding between the active sites on the protective layer and the lubricant layer. Accordingly, the lubricant layer containing the fluorine-containing ether compound of this embodiment exhibits excellent adhesion to the protective layer. As a result, pickup and spin-off can be suppressed.

In the formula (2), c represents 1 or 2, whereas in the formula (3), d represents 0 or 1, and e represents an integer of 2 to 4. However, the sum of the values of c and d is always 2. From the viewpoint of the adhesion with the protective layer, it is preferable that either c=2 and d=0, or c=1 and d=1. In those cases where c=2 and d=0, the hydroxyl groups are disposed in the same direction three-dimensionally, and a tendency is observed for improved adsorption of the hydroxyl groups to the protective layer. In those cases where c=1 and d=1, the distance between the hydroxyl groups contained within the -[A]-[B]— structure increases, interactions (such as hydrogen bonding) within the fluorine-containing ether compound represented by the formula (1) decrease, and the affinity with the protective layer can be enhanced. When c=1 and d=1, the value of e is preferably an integer of 2 to 3, and is most preferably 2.

As shown in the formula (1), the fluorine-containing ether compound of an embodiment of the present invention has a perfluoropolyether chain (hereafter sometimes abbreviated as "the PFPE chain") represented by $R^2$. When the lubricant containing the fluorine-containing ether compound is applied to the protective layer to form a lubricant layer, the PFPE chain coats the surface of the protective layer, and also imparts lubricity to the lubricant layer, thereby reducing the frictional force between the magnetic head and the protective layer. There are no particular limitations on the structure of $R^2$, and the structure may be selected appropriately in accordance with the performance and the like required of the lubricant containing the fluorine-containing ether compound.

Examples of the PFPE chain include chains composed of a perfluoromethylene oxide polymer, perfluoroethylene oxide polymer, perfluoro-n-propylene oxide polymer, perfluoroisopropylene oxide polymer, or copolymers of these compounds.

Specifically, $R^2$ in the formula (1) is preferably a structure represented by one of formulas (5) to (8) shown below. When $R^2$ is represented by any one of formulas (5) to (8), a fluorine-containing ether compound that yields a lubricant layer having good lubricity is obtained.

In the formula (5), there are no particular limitations on the sequence order of the ($CF_2$—$CF_2$—O) and ($CF_2$—O) repeating units. In the formula (5), the number g indicating the average polymerization degree of ($CF_2$—$CF_2$—O) and the number h indicating the average polymerization degree of ($CF_2$—O) may be the same or different. Formula (5) may include a random copolymer, block copolymer or alternating copolymer composed of the ($CF_2$—$CF_2$—O) and ($CF_2$—O) monomer units.

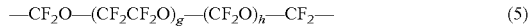
$$—CF_2O—(CF_2CF_2O)_g—(CF_2O)_h—CF_2— \quad (5)$$

(In the formula (5), g and h indicate average polymerization degrees, wherein g represents a number from 3 to 8, and h represents a number from 3 to 8.)

$$—CF_2O—(CF_2CF_2O)_i—CF_2— \quad (6)$$

(In the formula (6), i indicates an average polymerization degree, and represents a number from 5 to 13.)

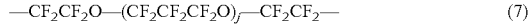
$$—CF_2CF_2O—(CF_2CF_2CF_2O)_j—CF_2CF_2— \quad (7)$$

(In the formula (7), j indicates an average polymerization degree, and represents a number from 3 to 8.)

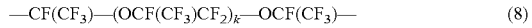
$$—CF(CF_3)—(OCF(CF_3)CF_2)_k—OCF(CF_3)— \quad (8)$$

(In the formula (8), k indicates an average polymerization degree, and represents a number from 3 to 8.)

In the formula (5), the average polymerization degree g is a number from 3 to 8, and is preferably from 4 to 7, and more preferably from 4 to 5. Further, the average polymerization degree h is a number from 3 to 8, and is preferably from 4 to 7, and more preferably from 4 to 5.

In the formula (6), when i is a number from 5 to 13, the number average molecular weight of the fluorine-containing ether compound of an embodiment of the present invention is more likely to fall within the preferred range. The value of i is preferably from 6 to 10, and more preferably from 6 to 8.

In the formula (7), when j is a number from 3 to 8, the number average molecular weight of the fluorine-containing ether compound of an embodiment of the present invention is more likely to fall within the preferred range. The value of j is preferably from 3.5 to 7, and more preferably from 3.5 to 5.

In the formula (8), when k is a number from 3 to 8, the number average molecular weight of the fluorine-containing ether compound of an embodiment of the present invention is more likely to fall within the preferred range. The value of k is preferably from 3.5 to 7, and more preferably from 3.5 to 5.

In those cases where $R^2$ in the formula (1) is represented by one of formulas (5) to (8), synthesis of the fluorine-containing ether compound is easier, and consequently preferred. Further, when $R^2$ in the formula (1) is represented by one of formulas (5) to (8), the ratio of the number of oxygen atoms (number of ether bonds (—O—)) relative to the number of carbon atoms in the PFPE chain, and the positioning of the oxygen atoms within the PFPE chain are appropriate. Consequently, a fluorine-containing ether compound having an appropriate level of hardness is obtained. As a result, the fluorine-containing ether compound applied to the protective layer is unlikely to undergo aggregation on the protective layer, and a thinner lubricant layer can be formed with a satisfactory coverage rate.

When $R^2$ in the formula (1) is represented by the formula (5), the raw materials are readily available, which is particularly desirable.

In the fluorine-containing ether compound of an embodiment of the present invention represented by the formula (1), $R^3$ is a terminal group represented by the formula (4). $R^3$ has two secondary hydroxyl groups and one primary hydroxyl group, and the carbon atoms to which the hydroxyl groups are bonded are linked via linking groups composed of a methylene group (—$CH_2$—) and an ether bond (—O—). As a result, the three hydroxyl groups contained in $R^3$ are disposed with an appropriate distance between the hydroxyl groups. Moreover, as a result of including the etheric oxygen atoms. $R^3$ imparts an appropriate level of flexibility to the molecular structure of the fluorine-containing ether compound represented by the formula (1). For these reasons, when a lubricant layer containing the fluorine-containing ether compound of an embodiment of the present invention is formed on top of a protective layer, the three hydroxyl groups within $R^3$ can more readily participate in bonding between the active sites on the protective layer and the lubricant layer. Accordingly, the lubricant layer containing the fluorine-containing ether compound of this embodiment exhibits excellent adhesion to the protective layer. As a result, the problem that can arise when fluorine-containing ether compound that has not adhered (adsorbed) to the protective layer undergoes aggregation and adheres to the magnetic head as foreign matter (smears) can be prevented, and pickup is suppressed. Further, spin-off that causes a reduction in the lubricant layer thickness as a result of the lubricant flying off or volatilizing due to the centrifugal force during high-speed rotation and/or heating can be suppressed.

Moreover, f in the formula (4) represents an integer of 2 to 5. Further, f is more preferably an integer of 2 to 3, and is most preferably 2.

If f is 1, then the structure stabilizes as a result of a regular alignment of five-membered ring-based intramolecular hydrogen bonding between the etheric oxygen atom and the hydroxyl group within the formula (4), causing a deterioration in the adhesion to the protective layer. By ensuring f is 2 or greater, this regular alignment is lost, and intramolecular interactions between the hydroxyl groups are inhibited, resulting in dramatically improved adhesion to the protective layer. If f is 6 or greater, then the proportion of fluorine atoms in the fluorine-containing ether compound molecule decreases, and the surface free energy of the overall molecule increases, which is undesirable.

In the fluorine-containing ether compound of an embodiment of the present invention represented by the formula (1), the two hydroxyl groups contained within the -[A]-[B]— structure and the three hydroxyl groups contained in $R^3$ are positioned with good balance at both terminals of $R^2$ (the PFPE chain) with methylene groups (—$CH_2$—) disposed therebetween. In addition, because the hydroxyl groups at each of these terminals are disposed with an appropriate distance between the hydroxyl groups, and have a structure with an appropriate level of flexibility, they can participate more easily in bonding between the active sites of the protective layer and the lubricant layer. Accordingly, with the fluorine-containing ether compound of an embodiment of the present invention, these hydroxyl groups adhere effectively to the protective layer at both terminals of the PFPE chain, with the resulting synergistic effect yielding excellent adhesion characteristics.

For the reasons outlined above, a lubricant layer containing the fluorine-containing ether compound of an embodiment of the present invention exhibits excellent adhesion to the protective layer. As a result, pickup and spin-off can be suppressed.

Specifically, the fluorine-containing ether compound represented by the formula (1) is preferably a compound represented by one of formulas (A1) to (T1) shown below. The numbers of repeating units represented by ma1 to mt1 and na1 to nt1 in the formulas (A1) to (T1) are numbers indicating average polymerization degrees, and need not necessarily be integers.

[Chemical formula 4]

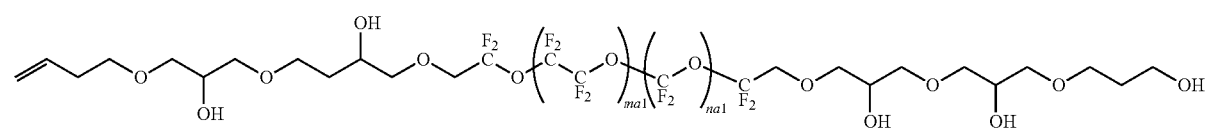

(A1)

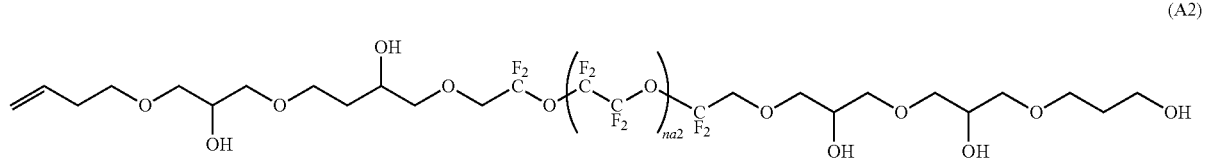

(A2)

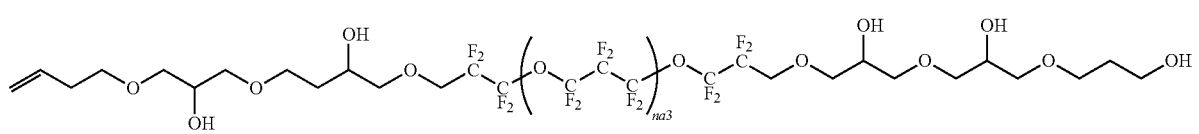

(A3)

(In the formula (A1), ma1 and na1 indicate average polymerization degrees, wherein ma1 represents a number from 3 to 8, and na1 represents a number from 3 to 8.)
(In the formula (A2), na2 indicates an average polymerization degree, and represents a number from 5 to 13.)
(In the formula (A3), na3 indicates an average polymerization degree, and represents a number from 3 to 8.)

[Chemical formula 5]

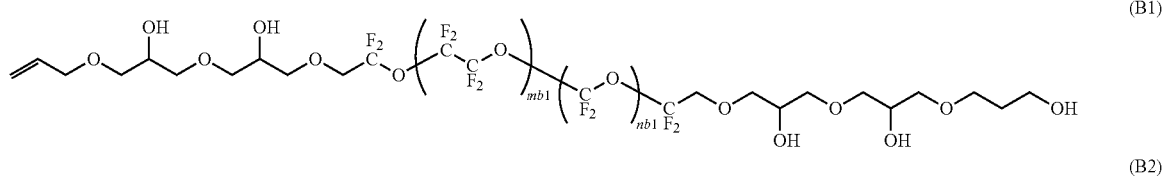
(B1)

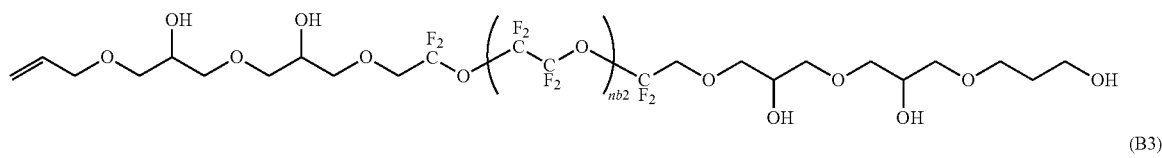
(B2)

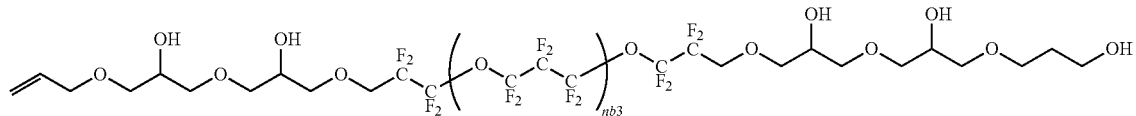
(B3)

(In the formula (B1), mb1 and nb1 indicate average polymerization degrees, wherein mb1 represents a number from 3 to 8, and nb1 represents a number from 3 to 8.)
(In the formula (B2), nb2 indicates an average polymerization degree, and represents a number from 5 to 13.)
(In the formula (B3), nb3 indicates an average polymerization degree, and represents a number from 3 to 8.)

[Chemical formula 6]

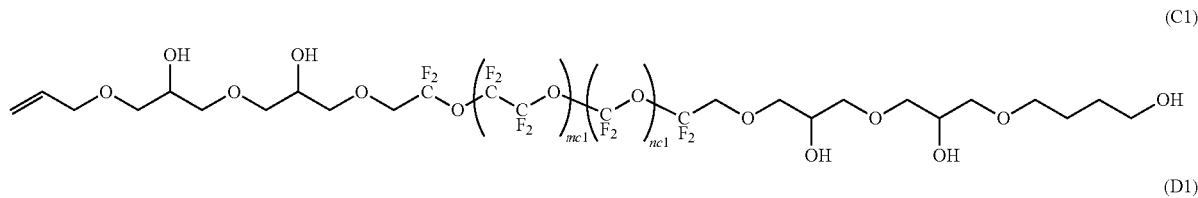
(C1)

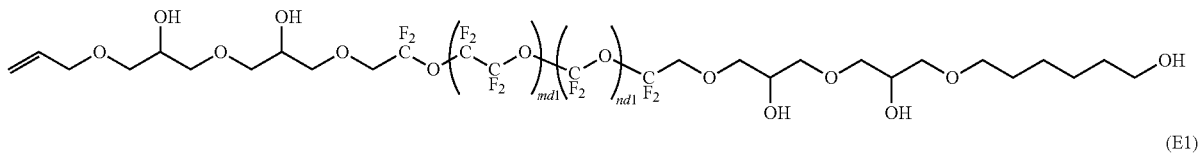
(D1)

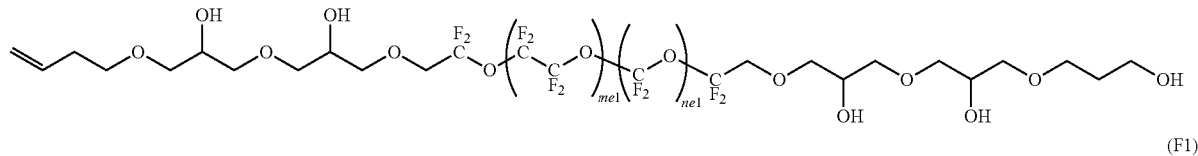
(E1)

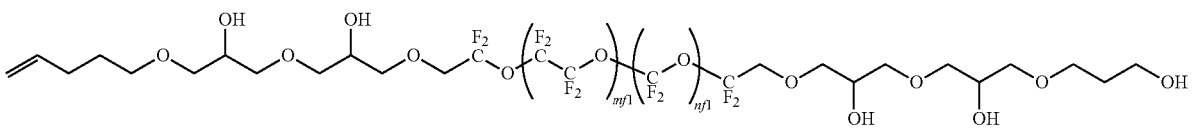
(F1)

(In the formula (C1), mc1 and nc1 indicate average polymerization degrees, wherein mc1 represents a number from 3 to 8, and nc1 represents a number from 3 to 8.)
(In the formula (D1), md1 and nd1 indicate average polymerization degrees, wherein md1 represents a number from 3 to 8, and nd1 represents a number from 3 to 8.)
(In the formula (E1), me1 and ne1 indicate average polymerization degrees, wherein me1 represents a number from 3 to 8, and ne1 represents a number from 3 to 8.)
(In the formula (F1), mf1 and nf1 indicate average polymerization degrees, wherein mf1 represents a number from 3 to 8, and nf1 represents a number from 3 to 8.)

[Chemical formula 7]

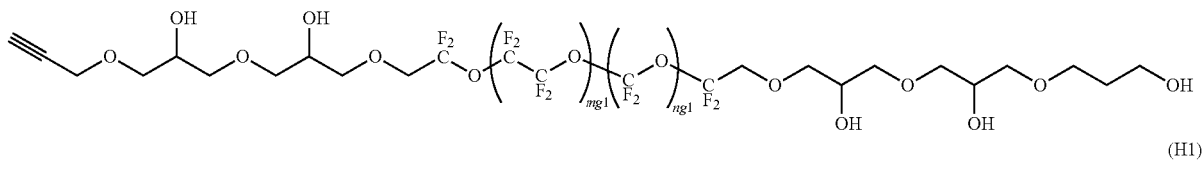

(G1)

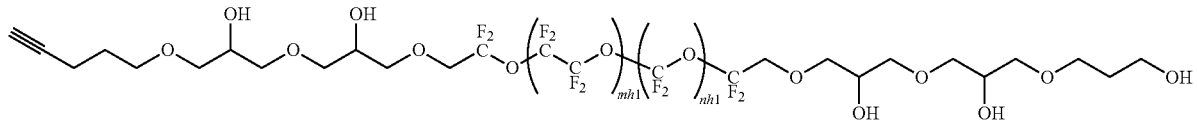

(H1)

(In the formula (G1), mg1 and ng1 indicate average polymerization degrees, wherein mg1 represents a number from 3 to 8, and ng1 represents a number from 3 to 8.)
(In the formula (H1), mh1 and nh1 indicate average polymerization degrees, wherein mh1 represents a number from 3 to 8, and nh1 represents a number from 3 to 8.)

[Chemical formula 8]

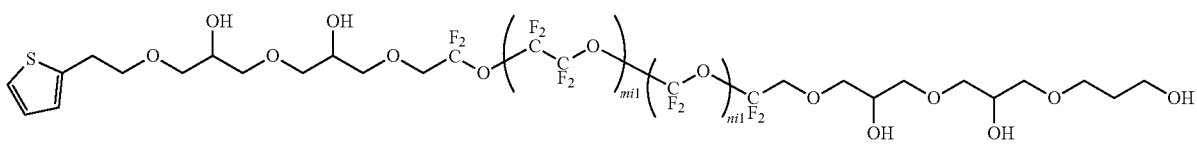

(I1)

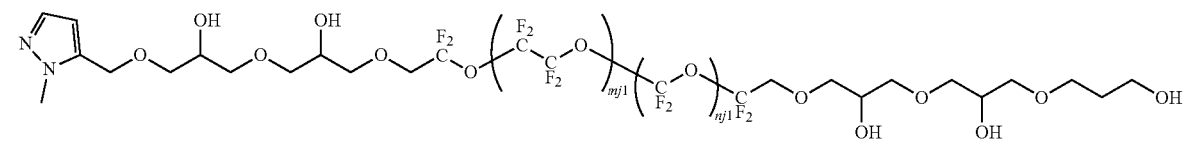

(J1)

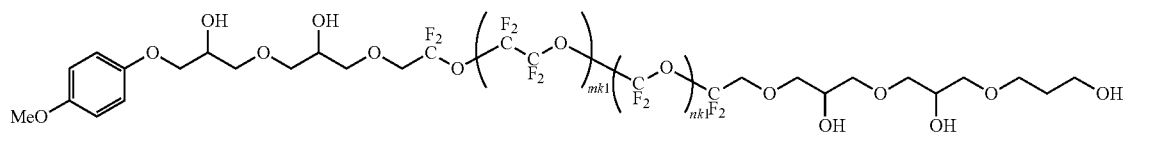

(K1)

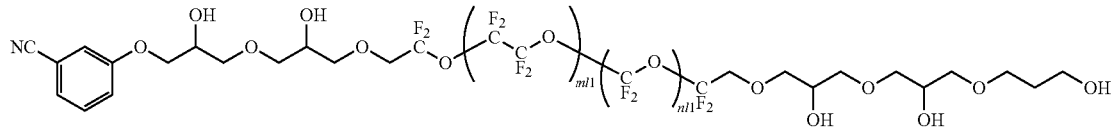

(L1)

(In the formula (I1), mi1 and ni1 indicate average polymerization degrees, wherein mi1 represents a number from 3 to 8, and ni1 represents a number from 3 to 8.)
(In the formula (J1), mj1 and nj1 indicate average polymerization degrees, wherein mj1 represents a number from 3 to 8, and nj1 represents a number from 3 to 8.)
(In the formula (K1), mk1 and nk1 indicate average polymerization degrees, wherein mk1 represents a number from 3 to 8, and nk1 represents a number from 3 to 8.)
(In the formula (L1), ml1 and nl1 indicate average polymerization degrees, wherein ml1 represents a number from 3 to 8, and nl1 represents a number from 3 to 8.)

[Chemical formula 9]

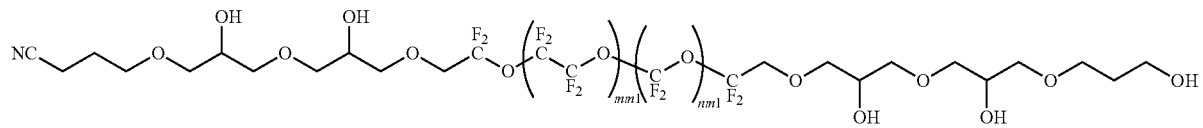

(M1)

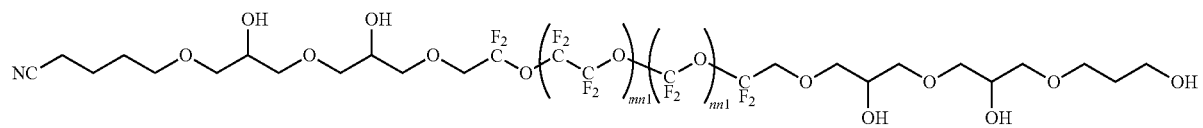

(N1)

(In the formula (M1), mm1 and nm1 indicate average polymerization degrees, wherein mm1 represents a number from 3 to 8, and nm1 represents a number from 3 to 8.)
(In the formula (N1), mn1 and nn1 indicate average polymerization degrees, wherein mn1 represents a number from 3 to 8, and nn1 represents a number from 3 to 8.)

[Chemical formula 10]

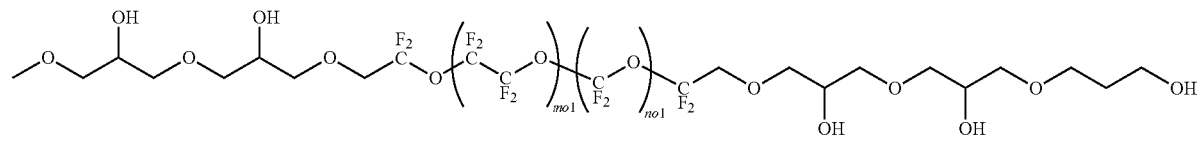

(O1)

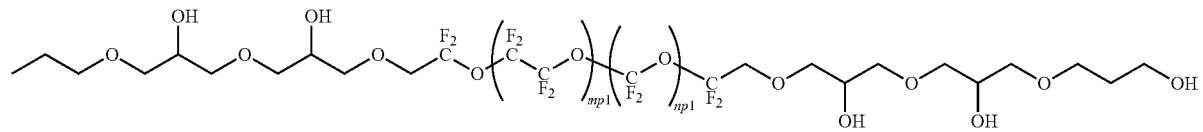

(P1)

(In the formula (O1), mo1 and no1 indicate average polymerization degrees, wherein mn1 represents a number from 3 to 8, and no1 represents a number from 3 to 8.)
(In the formula (P1), mp1 and np1 indicate average polymerization degrees, wherein mp1 represents a number from 3 to 8, and np1 represents a number from 3 to 8.)

[Chemical formula 11]

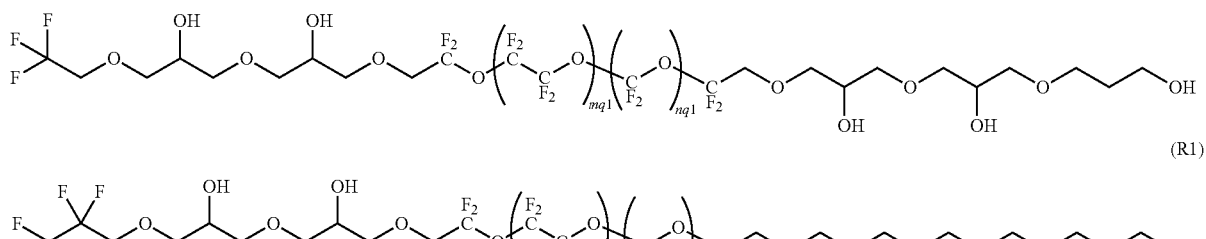

(In the formula (O1), mq1 and nq1 indicate average polymerization degrees, wherein mq1 represents a number from 3 to 8, and nq1 represents a number from 3 to 8.)
(In the formula (P1), mr1 and nr1 indicate average polymerization degrees, wherein mr1 represents a number from 3 to 8, and nr1 represents a number from 3 to 8.)

[Chemical formula 12]

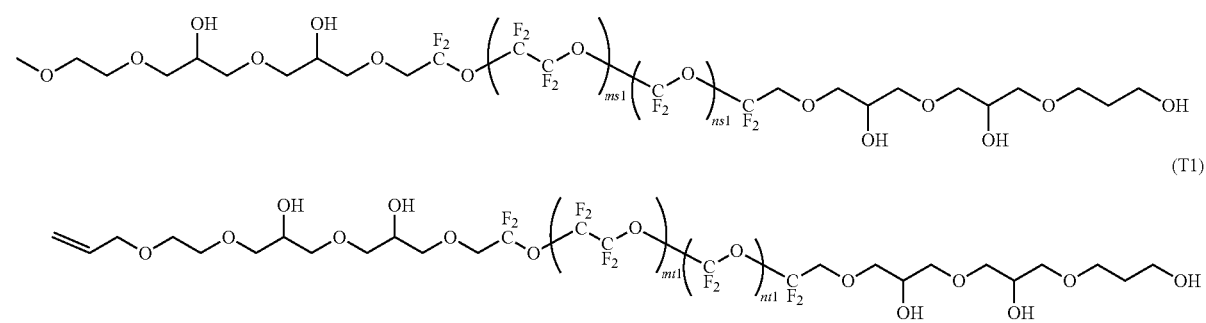

(In the formula (S1), ms1 and ns1 indicate average polymerization degrees, wherein ms1 represents a number from 3 to 8, and ns1 represents a number from 3 to 8.)
(In the formula (T1), mt1 and nt1 indicate average polymerization degrees, wherein mt1 represents a number from 3 to 8, and nt1 represents a number from 3 to 8.)

The fluorine-containing ether compound of an embodiment of the present invention has a number average molecular weight (Mn) that is preferably within a range from 1,000 to 2,300, more preferably within a range from 1,100 to 2,100, particularly preferably within a range from 1,200 to 1,800, and most preferably within a range from 1,200 to 1,600.

When the number average molecular weight is at least 1,000, the lubricant containing the fluorine-containing ether compound of this embodiment is more resistant to evaporation. Accordingly, when the number average molecular weight is at least 1,000, pickup and spin-off can be better prevented. Further, when the number average molecular weight is not more than 2,300, the viscosity of the fluorine-containing ether compound does not become overly high, and a viscosity appropriate for a lubricant is obtained. If the number average molecular weight exceeds 2,300, then the viscosity of the fluorine-containing ether compound increases, and the handling tends to deteriorate.

In terms of ease of availability of the raw materials for the PFPE chain, the number average molecular weight is preferably within a range from 1,100 to 2,100. When the number average molecular weight is within a range from 1,200 to 1,800, the coverage rate does not worsen even if the thickness of the lubricant layer is reduced, and favorable chemical substance resistance and wear resistance can be maintained. A number average molecular weight within a range from 1,200 to 1,600 provides the best balance of performance in terms of preventing pickup and spin-off while enabling a reduction in the thickness of the lubricant layer.

[Production Method]

Them are no particular limitations on the method used for producing the fluorine-containing ether compound of an embodiment of the present invention, and production may be conducted using conventional production methods. For example, the fluorine-containing ether compound of an embodiment of the present invention may be produced using the production method described below.

First, a fluorine-based compound is prepared that has a PFPE chain corresponding with $R^2$ in the formula (1), with hydroxymethyl groups (—$CH_2OH$) disposed at both terminals of the molecule.

Subsequently, the hydroxyl group of the hydroxymethyl group positioned at one of the terminals of this fluorine-based compound is substituted with a group composed of $R^1$—$(O(CH_2)_a)_b$-[A]-[B]—O— from formula (1) (the first reaction). The hydroxyl group of the hydroxymethyl group positioned at the other terminal is then substituted with a terminal group composed of —$R^1$ from formula (1) (the second reaction).

The first reaction and the second reaction can be conducted using conventional methods, and these methods may be selected appropriately in accordance with the types of terminals in the formula (1). Further, either of the first reaction and the second reaction may be conducted first.

[Lubricant for Magnetic Recording Medium]

A lubricant for a magnetic recording medium according to an embodiment of the present invention contains the fluorine-containing ether compound represented by the formula (1).

The lubricant of this embodiment may be mixed, as required, with conventional materials typically used as lubricant materials, provided that the characteristics achieved as a result of including the fluorine-containing ether compound represented by the formula (1) are not impaired.

Specific examples of these conventional materials include Fomblin (a registered trademark) ZDIAC, Fomblin ZDEAL and Fomblin AM-2001 (all manufactured by Solvay Solexis S.A.), and Moresco A20H (manufactured by Moresco Corporation). Conventional materials that are mixed and used with the lubricant of an embodiment of the present invention preferably have a number average molecular weight within a range from 1,000 to 10,000.

In those cases where the lubricant of an embodiment of the present invention contains materials other than the fluorine-containing ether compound represented by the formula (1), the amount of the fluorine-containing ether compound represented by the formula (1) within the lubricant of the embodiment is preferably at least 50% by mass, and more preferably 70% by mass or greater. The amount of the fluorine-containing ether compound represented by the formula (1) may be at least 80% by mass, or may be 90% by mass or greater.

Since the lubricant of an embodiment of the present invention contains the fluorine-containing ether compound represented by the formula (1), a lubricant layer can be obtained which exhibits favorable adhesion to the protective layer, and good suppression of pickup and spin-off, even when the molecular weight is low.

[Magnetic Recording Medium]

A magnetic recording medium according to an embodiment of the present invention contains at least a magnetic layer, a protective layer and a lubricant layer provided sequentially on a substrate.

In the magnetic recording medium of this embodiment, one or two or more base layers may be provided between the substrate and the magnetic layer if required. Further, an adhesive layer and/or a soft magnetic layer may be provided between the base layer and the substrate.

The FIGURE is a schematic cross-sectional view illustrating one embodiment of the magnetic recording medium of an embodiment of the present invention.

The magnetic recording medium 10 of this embodiment has a structure in which an adhesive layer 12, a soft magnetic layer 13, a first base layer 14, a second base layer 15, a magnetic layer 16, a protective layer 17, and a lubricant layer 18 are provided in sequence on top of a substrate 11.

[Substrate]

Examples of materials that may be used as the substrate 11 include non-magnetic substrates having a film composed of NiP or a NiP alloy formed on a substrate composed of a metal or an alloy material such as Al or an Al alloy.

Further, non-magnetic substrates formed from non-metal materials such as glass, ceramic, silicon, silicon carbide, carbon or resin may also be used as the substrate 11, and non-magnetic substrates having a film composed of NiP or a NiP alloy formed on a substrate formed from any of these non-metal materials may also be used.

Glass substrates are rigid and have excellent smoothness, and are therefore ideal for increasing recording density. Examples of glass substrates include aluminosilicate glass substrates, and chemically strengthened aluminosilicate glass substrates are particularly suitable.

The roughness of the main surface of the substrate 11 is preferably extremely smooth, with an Rmax value of not more than 6 nm, and an Ra value of 0.6 nm or less. These surface roughness Rmax and Ra values refer to the values prescribed in JIS B0601.

[Adhesive Layer]

The adhesive layer 12 prevents any progression of corrosion of the substrate 11 that can occur when the substrate 11 is positioned in contact with the soft magnetic layer 13 that is provided on top of the adhesive layer 12.

The material for the adhesive layer 12 may be selected appropriately, for example, from among Cr, Cr alloys, Ti, Ti alloys, CrTi, NiAl, and AlRu alloys and the like. The adhesive layer 12 can be formed, for example, by a sputtering method.

[Soft Magnetic Layer]

The soft magnetic layer 13 preferably has a structure in which a first soft magnetic film, an intermediate layer formed from a Ru film, and a second soft magnetic film are stacked sequentially. In other words, the soft magnetic layer 13 preferably has a structure in which, by sandwiching an intermediate layer formed from a Ru film between two layers of soft magnetic films, the soft magnetic films above and below the intermediate layer are linked by antiferromagnetic coupling (AFC).

Examples of the materials for the first soft magnetic film and the second soft magnetic film include CoZrTa alloys and CoFe alloys.

Any of Zr, Ta and Nb is preferably added to the CoFe alloy used in the first soft magnetic film and the second soft magnetic film. This promotes the amorphization of the first soft magnetic film and the second soft magnetic film, enables the orientation of the first base layer (seed layer) to be improved, and also enables a reduction in the floating height of the magnetic head.

The soft magnetic layer 13 can be formed, for example, by a sputtering method.

[First Base Layer]

The first base layer 14 is a layer for controlling the orientation and crystal size of the second base layer 15 and the magnetic layer 16 provided on top of the first base layer 14.

Examples of the first base layer 14 include a Cr layer, Ta layer, Ru layer, or a CrMo alloy layer, CoW alloy layer, CrW alloy layer, CrV alloy layer, or CrTi alloy layer or the like.

The first base layer 14 can be formed, for example, by a sputtering method.

[Second Base Layer]

The second base layer 15 is a layer that controls the orientation of the magnetic layer 16 to achieve a favorable orientation. The second base layer 15 is preferably a layer formed from Ru or a Ru alloy.

The second base layer 15 may be composed of a single layer, or may be composed of a plurality of layers. When the second base layer 15 is composed of a plurality of layers, all of the layers may be formed from the same material, or at least one layer may be formed from a different material.

The second base layer 15 can be formed, for example, by a sputtering method.

[Magnetic Layer]

The magnetic layer 16 is formed from a magnetic film having an easy axis of magnetization that is oriented in either the perpendicular direction or the horizontal direction relative to the substrate surface. The magnetic layer 16 is a layer containing Co and Pt, and may also contain oxides, or Cr, B, Cu, Ta or Zr or the like in order to improve the SNR (Signal to Noise Ratio) characteristics.

Examples of oxides that may be included in the magnetic layer 16 include $SiO_2$, SiO, $Cr_2O_3$, CoO, $Ta_2O_3$ and $TiO_2$.

The magnetic layer 16 may be composed of a single layer, or may be composed of a plurality of magnetic layers formed from materials having different compositions.

For example, in the case where the magnetic layer 16 is composed of three layers, namely a first magnetic layer, a second magnetic layer and a third magnetic layer stacked in that order from the lower side, the first magnetic layer preferably has a granular structure formed from a material containing Co, Cr and Pt, and also containing an oxide. Examples of preferred oxides that may be included in the first magnetic layer include oxides of Cr, Si, Ta, Al, Ti, Mg and Co, Among these, oxides such as $TiO_2$, $Cr_2O_3$ and $SiO_2$ can be used particularly favorably. Further, the first magnetic layer is preferably formed from a composite oxide in which two or more oxides are added. Among such composite oxides. $Cr_2O_3$—$SiO_2$, $Cr_2O_3$—$TiO_2$, and $SiO_2$—$TiO_2$ and the like can be used particularly favorably.

The first magnetic layer may also contain, in addition to Co, Cr, Pt and the oxide, one or more elements selected from among B, Ta, Mo, Cu, Nd, W, Nb, Sm, Tb, Ru and Re. The same materials as those used for the first magnetic layer can be used for the second magnetic layer. The second magnetic layer preferably has a granular structure.

The third magnetic layer preferably has a non-granular structure formed from a material containing Co, Cr and Pt, but containing no oxides. In addition to Co, Cr and Pt, the third magnetic layer may also contain one or more elements selected from among B, Ta, Mo, Cu, Nd, W, Nb, Sm, Tb, Ru, Re and Mn.

In those cases where the magnetic layer 16 is composed of a plurality of magnetic layers, a non-magnetic layer is preferably provided between adjacent magnetic layers.

When the magnetic layer 16 is composed of three layers, namely a first magnetic layer, a second magnetic layer and a third magnetic layer, a non-magnetic layer is preferably provided between the first magnetic layer and the second magnetic layer, and between the second magnetic layer and the third magnetic layer.

Examples of materials that may be used favorably for the non-magnetic layers provided between the adjacent magnetic layers of the magnetic layer 16 include Ru, Ru alloys, CoCr alloys, and CoCrX1 alloys (wherein X1 represents one element, or two or more elements, selected from among Pt, Ta, Zr, Re, Ru, Cu, Nb, Ni, Mn, Ge, Si, O, N, W, Mo, Ti, V and B) and the like.

Alloy materials containing oxides, metal nitrides or metal carbides are preferably used for the non-magnetic layers provided between the adjacent magnetic layers of the magnetic layer 16. Specific examples of oxides that may be used include $SiO_2$, $Al_2O_3$, $Ta_2O_5$, $Cr_2O_3$, MgO, $Y_2O_3$ and $TiO_2$. Examples of metal nitrides that may be used include AlN, $Si_3N_4$, TaN and CrN. Examples of metal carbides that may be used include TaC, BC and SiC.

The non-magnetic layers may be formed, for example, by a sputtering method.

In order to achieve a higher recording density, the magnetic layer 16 is preferably a magnetic layer for perpendicular magnetic recording in which the easy axis of magnetization is oriented in a direction perpendicular to the substrate surface. However, the magnetic layer 16 may also be a magnetic layer for in-plane magnetic recording.

The magnetic layer 16 may be formed using any conventional method such as a vapor deposition method, ion beam sputtering method or magnetron sputtering method. The magnetic layer 16 is usually formed by a sputtering method.

[Protective Layer]

The protective layer 17 protects the magnetic layer 16. The protective layer 17 may be composed of a single layer, or may be composed of a plurality of layers. Examples of the material for the protective layer 17 include carbon, carbon which contains nitrogen, and silicon carbide.

A carbon-based protective layer can be used favorably as the protective layer 17, and an amorphous carbon protective layer is particularly preferred. When the protective layer 17 is a carbon-based protective layer, the interactions with the polar groups (particularly the hydroxyl groups) contained in the fluorine-containing ether compound included in the lubricant layer 18 can be further enhanced, which is desirable. The adhesive strength between the carbon-based protective layer and the lubricant layer 18 can be controlled by using a hydrogenated carbon and/or nitrogenated carbon for the carbon-based protective layer, and then adjusting the hydrogen content and/or nitrogen content within the carbon-based protective layer.

The hydrogen content in the carbon-based protective layer, when measured by hydrogen forward scattering (HFS), is preferably within a range from 3 atomic % to 20 atomic %. Further, the nitrogen content in the carbon-based protective layer, when measured by X-ray photoelectron spectroscopy (XPS), is preferably within a range from 4 atomic % to 12 atomic %.

The hydrogen and/or nitrogen contained in the carbon-based protective layer need not necessarily be distributed uniformly through the entire carbon-based protective layer. For example, the carbon-based protective layer preferably has a composition gradient in which the nitrogen is incorporated in the protective layer 17 near the lubricant layer 18 and the hydrogen is incorporated in the protective layer 17 near the magnetic layer 16. In this case, the adhesive strength between the carbon-based protective layer and the magnetic layer 16 and lubricant layer 18 can be further improved. This is because the nitrogen within the protective layer 17 functions as active sites, promoting the bonding with the lubricant layer. The hydrogen or nitrogen within the carbon-based protective layer has a function as an active site.

The thickness of the protective layer 17 is preferably within a range from 1 nm to 7 nm. When the thickness of the protective layer 17 is at least 1 nm, satisfactory performance as the protective layer 17 can be achieved. When the thickness of the protective layer 17 is not more than 7 nm, it is preferable from the viewpoint of keeping the protective layer 17 thin.

Examples of the method used for depositing the protective layer 17 include sputtering methods using a target material containing carbon. CVD (chemical vapor deposition) methods using a hydrocarbon raw material such as ethylene or toluene, and IBD (ion beam deposition) methods.

In those cases where a carbon-based protective layer is formed as the protective layer 17, the protective layer can be deposited, for example, using a DC magnetron sputtering method. In particular, when forming a carbon-based protective layer as the protective layer 17, deposition of an amorphous carbon protective layer using a plasma CVD method is preferred. An amorphous carbon protective layer deposited by a plasma CVD method has a uniform surface with very little roughness.

[Lubricant Layer]

The lubricant layer 18 prevents contamination of the magnetic recording medium 10. Further, the lubricant layer 18 also reduces the frictional force of the magnetic head of the magnetic recording and playback device that slides across the top of the magnetic recording medium 10, and improves the durability of the magnetic recording medium 10.

As illustrated in the FIGURE, the lubricant layer 18 is formed so as to contact the protective layer 17. The lubricant layer 18 contains the fluorine-containing ether compound of an embodiment of the present invention.

In those cases where the protective layer 17 disposed beneath the lubricant layer 18 is a carbon-based protective layer, the lubricant layer 18 bonds to the protective layer 17 with a particularly powerful bonding strength. As a result, even if the thickness of the lubricant layer 18 is reduced, a magnetic recording medium 10 in which the surface of the protective layer 17 is coated with a high coverage rate can be obtained easily, and contamination of the surface of the magnetic recording medium 10 can be effectively prevented.

The average thickness of the lubricant layer 18 is preferably within a range from 0.5 nm (5 Å) to 3.0 nm (30 Å), and more preferably from 0.5 nm (5 Å) to 2.0 nm (20 Å). When the average thickness of the lubricant layer 18 is at least 0.5 nm, the lubricant layer 18 is formed with uniform thickness without becoming an island-like or mesh-like layer. As a result, the surface of the protective layer 17 can be coated with the lubricant layer 18 with a high coverage rate. Further, when the average thickness of the lubricant layer 18 is not more than 3.0 nm, the lubricant layer 18 can be kept suitably thin, and the floating height of the magnetic head can be satisfactorily reduced.

When the surface of the protective layer 17 is not coated with the lubricant layer 18 with a satisfactorily high coverage rate, environmental substances adsorbed to the surface of the magnetic recording medium 10 can pass through voids in the lubricant layer 18 and penetrate beneath the lubricant layer 18. Environmental substances that penetrate beneath the lubricant layer 18 can adsorb and bond to the protective layer 17, producing contaminants. Then, during magnetic recording or playback, these contaminants (aggregated components) can adhere (transfer) to the magnetic head as smears, and may cause damage to the magnetic head, or cause a deterioration in the magnetic recording and playback characteristics of the magnetic recording and playback device.

Examples of environmental substances that produce contaminants include siloxane compounds (cyclic siloxanes and linear siloxanes), ionic impurities, hydrocarbons having comparatively large molecular weights such as octacosane, and plasticizers such as dioctyl phthalate. Examples of metal ions that may be incorporated in the ionic impurities include sodium ions and potassium ions. Examples of inorganic ions that may be incorporated in the ionic impurities include chloride ions, bromide ions, nitrate ions, sulfate ions and ammonium ions. Examples of organic ions that may be incorporated in the ionic impurities include oxalate ions and formate ions.

[Lubricant Layer Formation Method]

One example of the method used for forming the lubricant layer 18 is a method in which a partially produced magnetic recording medium is first prepared having each of the layers up to and including the protective layer 17 formed on the substrate 11, and a solution for forming the lubricant layer is then applied to the protective layer 17 and dried.

The solution for forming the lubricant layer may be obtained by dispersing or dissolving the lubricant for magnetic recording medium of an embodiment described above in a solvent as required, so as to achieve a viscosity and concentration that are suitable for the coating method.

Examples of the solvent used in the solution for forming the lubricant layer include fluorine-based solvents such as Vertrel (a registered trademark) XF (a product name, manufactured by Mitsui DuPont Fluorochemicals Co., Ltd.) and the like.

There are no particular limitations on the coating method used for applying the solution for forming the lubricant layer, and examples include spin-coating methods, spray methods, paper coating methods, and dipping methods.

When a dipping method is used, for example, the method described below may be used. First, the substrate 11 having the various layers up to and including the protective layer 17 formed thereon is dipped in the solution for forming the lubricant layer housed in the dipping tank of a dip coating device. Subsequently, the substrate 11 is pulled up out of the dipping tank at a prescribed speed. This coats the solution for forming the lubricant layer onto the surface of the protective layer 17 of the substrate 11.

By using a dipping method, the solution for forming the lubricant layer can be applied uniformly to the surface of the protective layer 17, enabling the lubricant layer 18 to be formed with a uniform thickness on the protective layer 17.

In this embodiment, the substrate 11 having the lubricant layer 18 formed thereon is preferably subjected to a heat treatment. Conducting a heat treatment improves the adhesion between the lubricant layer 18 and the protective layer 17, and increases the adhesive strength between the lubricant layer 18 and the protective layer 17.

The heat treatment temperature is preferably within a range from 100° C. to 180° C. When the heat treatment temperature is at least 100° C., the effect of improving the adhesion between the lubricant layer 18 and the protective layer 17 can be achieved sufficiently. Further, when the heat treatment temperature is not more than 180° C. thermal degradation of the lubricant layer 18 can be prevented. The heat treatment time is preferably within a range from 10 minutes to 120 minutes.

In one embodiment of the present invention, in order to further improve the adhesive strength of the lubricant layer 18 to the protective layer 17, a treatment in which the lubricant layer 18 on the substrate 11 is irradiated with ultraviolet radiation (UV) may be conducted either before the heat treatment or after the heat treatment.

The magnetic recording medium 10 of an embodiment of the present invention has at least the magnetic layer 16, the protective layer 17 and the lubricant layer 18 provided sequentially on the substrate 11. In the magnetic recording medium 10 of this embodiment, the lubricant layer 18 containing the fluorine-containing ether compound described above is formed on top of the protective layer 17.

With conventional lubricants, reducing the thickness of the lubricant layer while maintaining the reliability and durability of the magnetic recording medium is difficult, and if the molecular weight of the fluorine-containing ether compound used in the lubricant is reduced to enable formation of a thinner lubricant layer, then spin-off problems have tended to occur.

Since the lubricant of an embodiment of the present invention contains the fluorine-containing ether compound represented by the formula (1), a lubricant layer can be formed that is capable of suppressing pickup and spin-off even when the molecular weight is reduced.

Accordingly, the lubricant layer 18 of an embodiment of the present invention exhibits favorable adhesion to the protective layer, and can suppress pickup and spin-off even when the molecular weight is reduced. As a result, the magnetic recording medium 10 of an embodiment of the present invention has excellent reliability and durability. Further, by using the lubricant layer 18 of an embodiment of the present invention, a further reduction in magnetic spacing can be achieved, which can contribute to an increase in recording density on the magnetic recording medium. Consequently, the magnetic recording medium 10 of an embodiment of the present invention is particularly ideal as the magnetic disk loaded in an LUL (Load Unload) magnetic disk device.

EXAMPLES

The present invention is described below in further detail using a series of examples and comparative examples. However, the present invention is not limited solely to the following examples.

[NMR Measurement Method]

Structural identification of the compounds obtained in the following Examples 1 to 54 was conducted by $^1$H-NMR and $^{19}$F-NMR measurements using an AVANCE III-400 device manufactured by Bruker BioSpin Corporation.

A sample of about 10 mg for use in the NMR measurements was weighed and dissolved in about 0.5 mL of deuterated acetone (containing added hexafluorobenzene as a standard) before being used in the measurements. The standard used for the $^1$H-NMR chemical shift was the acetone peak at 2.05 ppm. The standard used for the $^{19}$F-NMR chemical shift was the hexafluorobenzene peak at −164.7 ppm.

The number average molecular weight of each compound shown in Tables 2 to 4 was calculated from the $^{19}$F-NMR measurement results. Specifically, the number of repeating units in the PFPE chain was calculated front the fluorine atom integral intensity measured by $^{19}$F-NMR, and this was used to determine the number average molecular weight.

Example 1

A compound (A1) represented by the formula (A1) shown above (wherein within the formula (A1), the average polymerization degree represented by ma1 is 3.4, and the average polymerization degree represented by na1 is 3.4) was obtained using the method described below.

First, a compound represented by a formula (10) shown below was synthesized using the method described below. Specifically, 2 equivalents of 3-buten-1-ol and 1 equivalent of epichlorohydrin were reacted to synthesize a compound (9) represented by a formula (9) shown below. Following reaction of the thus obtained compound (9) with 3,4-dihydro-2H-pyran to protect the hydroxyl group with a tetrahydropyranyl group, n-chloroperbenzoic acid was used to oxidize the double bond at one end of the molecule, thus synthesizing the compound (10) represented by the formula (10) shown below.

[Chemical formula 13]

(9)

(10)

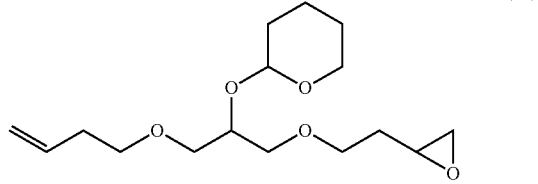

Further, a compound represented by a formula (12) shown below was synthesized using the method described below. Specifically, the primary hydroxyl group of 3-allyloxy-1,2-propanediol was protected with a t-butyldimethylsilyl group. The secondary hydroxyl group was then protected with a methoxymethyl group, and by subsequently removing the t-butyldimethylsilyl group from the resulting compound, a compound (11) represented by a formula (11) shown below was synthesized. By reacting the thus obtained compound (11) with 2-(3-chloropropoxy)tetrahydropyran, and then using m-chloroperbenzoic acid to oxidize the double bond, the compound (12) represented by the formula (12) shown below was synthesized.

[Chemical formula 14]

(11)

(12)

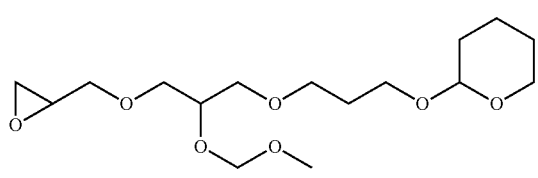

Under a nitrogen gas atmosphere, a 200 mL round-bottom flask was charged with a fluoropolyether represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1) (40.0 g), the compound (10) represented by the formula (10) shown above (9.01 g), and t-BuOH (tertiary butyl alcohol) (40.0 mL), and the contents were stirred at room temperature until a uniform mixture was obtained. Subsequently, t-BuOK (potassium tertiary butoxide) (1.68 g) was added to the round-bottom flask, and the resulting mixture was reacted under stirring at 70° C., for 12 hours.

Subsequently, the obtained reaction product was cooled to 25° C. water was added. Vertrel (a registered trademark) XF, manufactured by Mitsui DuPont Fluorochemicals Co., Ltd. (hereafter sometimes referred to as "Vertrel XF"), was added as a solvent, and the organic layer was extracted and washed with water. The organic layer was then dried over anhydrous sodium sulfate, and following removal of the desiccant by filtration, the filtrate was concentrated. The residue was purified by silica gel column chromatography, yielding a compound (13) represented by a formula (13) shown below (22.0 g).

erization degree represented by ma1 is 6.2, and the average polymerization degree represented by na1 is 6.2) was obtained using the method described below.

With the exception of replacing the fluoropolyether in Example 1 represented by $HOCH_2CF_2O(CF_2CF_2O)_g(CF_2O)_nCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_nCF_2CH_2OH$ (wherein the average polymerization degree represented by g is 6.2, and the average polymerization degree represented by h is 6.2) (number average molecular weight: 1,300, molecular weight distribution: 1.1) (40.0 g), the same operations as Example 1 were conducted, yielding 14.8 g of the compound (A1).

[Chemical formula 15]

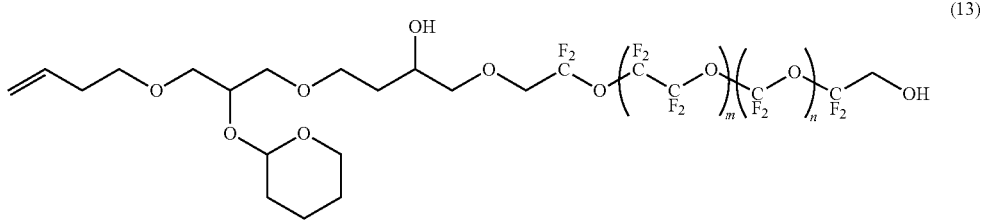

(13)

(In the formula (13), the average polymerization degree represented by nm is 3.4, and the average polymerization degree represented by n is 3.4.)

Under a nitrogen gas atmosphere, a 200 ml round-bottom flask was charged with the compound (13) represented by the formula (13) shown above (22.0 g), the compound (12) represented by the formula (12) shown above (7.36 g), and t-BuOH (tertiary butyl alcohol)(65.0 mL), and the contents were stirred at room temperature until a uniform mixture was obtained. Subsequently, t-BuOK (potassium tertiary butoxide) (0.67 g) was added to the round-bottom flask, and the resulting mixture was reacted under stirring at 70° C., for 16 hours.

Subsequently, the obtained reaction product was cooled to 25° C., a 7% hydrogen chloride/methanol reagent (104.2 g) was added, and a deprotection reaction was conducted by stirring the mixture at room temperature for 3 hours.

A 7% sodium bicarbonate solution (250 mL) was added to neutralize the obtained reaction product. Vertrel XF was added, and the organic layer was extracted and washed with water. The organic layer was then dried over anhydrous sodium sulfate, and following removal of the desiccant by filtration, the filtrate was concentrated. The residue was purified by silica gel column chromatography, yielding 17.1 g of the compound (A1).

$^1$H-NMR and $^{19}$F-NMR measurements of the obtained compound (A1) were conducted, and the structure was identified based on the following results.

$^1$H-NMR (acetone-$d_6$): δ [ppm]=1.58 to 1.82 (4H), 2.34 (2H), 3.48 to 4.20 (35H), 4.98 (1H), 5.05 (1H), 5.82 (1H)

$^{19}$F-NMR (acetone-$d_6$): δ [ppm]=−51.99 to −55.72 (6.8F), −78.48 (2F), −80.66 (2F), −89.16 to −91.14 (13.6F)

Example 2

A compound (A1) represented by the formula (A1) shown above (wherein within the formula (A1), the average polym- $^1$H-NMR and $^{19}$F-NMR measurements of the obtained compound (A1) were conducted, and the structure was identified based on the following results.

$^1$H-NMR (acetone-$d_6$): δ [ppm]=1.58 to 1.82 (4H), 2.34 (2H), 3.48 to 4.20 (35H), 4.98 (1H), 5.05 (1H), 5.82 (1H)

$^{19}$F-NMR (acetone-$d_6$): δ [ppm]=−51.99 to −55.72 (12.4F), −78.48 (2F), −80.66 (2F), −89.16 to −91.14 (24.8F)

Example 3

A compound (A1) represented by the formula (A1) shown above (wherein within the formula (A1), the average polymerization degree represented by ma1 is 7.8, and the average polymerization degree represented by na1 is 7.8) was obtained using the method described below.

With the exception of replacing the fluoropolyether in Example 1 represented by $HOCH_2CF_2O(CF_2CF_2O)_g(CF_2O)_nCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_nCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 1 were conducted, yielding 14.2 g of the compound (A1).

$^1$H-NMR and $^{19}$F-NMR measurements of the obtained compound (A1) were conducted, and the structure was identified based on the following results.

$^1$H-NMR (acetone-$d_6$): δ [ppm]=1.58 to 1.82 (4H), 2.34 (2H), 3.48 to 4.20 (35H), 4.98 (1H), 5.05 (1H), 5.82 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Example 41

A compound (A2) represented by the formula (A2) shown above (wherein within the formula (A2), the average polymerization degree represented by na2 is 5.4) was obtained using the method described below.

With the exception of replacing the fluoropolyether in Example 1 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_iCF_2CH_2OH$ (wherein the average polymerization degree represented by i is 5.4) (number average molecular weight: 800, molecular weight distribution: 1.1) (40.0 g), the same operations as Example 1 were conducted, yielding 13.4 g of the compound (A2).

$^1$H-NMR and $^{19}$F-NMR measurements of the obtained compound (A2) were conducted, and the structure was identified based on the following results.

$^1$H-NMR (acetone-$d_6$): δ [ppm]=1.59 to 1.81 (4H), 2.34 (2H), 3.40 to 4.20 (35H), 4.99 (1H), 5.08 (1H), 5.84 (1H)

$^{19}$F-NMR (acetone-$d_6$): δ [ppm]=−78.57 (4F), −88.92 to −89.57 (21.6F)

Example 5

A compound (A2) represented by the formula (A2) shown above (wherein within the formula (A2), the average polymerization degree represented by na2 is 9.7) was obtained using the method described below.

With the exception of replacing the fluoropolyether in Example 1 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_iCF_2CH_2OH$ (wherein the average polymerization degree represented by i is 9.7) (number average molecular weight: 1,300, molecular weight distribution: 1.1) (40.0 g), the same operations as Example 1 were conducted, yielding 12.4 g of the compound (A2).

$^1$H-NMR and $^{19}$F-NMR measurements of the obtained compound (A2) were conducted, and the structure was identified based on the following results.

$^1$H-NMR (acetone-$d_6$): δ [ppm]=1.59 to 1.81 (4H), 2.34 (2H), 3.40 to 4.20 (35H), 4.99 (1H), 5.08 (1H), 5.84 (H)

$^{19}$F-NMR (acetone-$d_6$): δ [ppm]=−78.57 (4F), −88.92 to −89.57 (38.8F)

Example 6

A compound (A2) represented by the formula (A2) shown above (wherein within the formula (A2), the average polymerization degree represented by na2 is 12.3) was obtained using the method described below.

With the exception of replacing the fluoropolyether in Example 1 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_iCF_2CH_2OH$ (wherein the average polymerization degree represented by i is 12.3) (number average molecular weight: 1,600, molecular weight distribution: 1.1) (40.0 g), the same operations as Example 1 were conducted, yielding 11.1 g of the compound (A2).

$^1$H-NMR and $^{19}$F-NMR measurements of the obtained compound (A2) were conducted, and the structure was identified based on the following results.

$^1$H-NMR (acetone-$d_6$): δ [ppm]=1.59 to 1.81 (4H), 2.34 (2H), 3.40 to 4.20 (35H), 4.99 (1H), 5.08 (1H), 5.84 (1H)

$^{19}$F-NMR (acetone-$d_6$): δ [ppm]=−78.57 (4F), −88.92 to −89.57 (49.2F)

Example 71

A compound (A3) represented by the formula (A3) shown above (wherein within the formula (A3), the average polymerization degree represented by na3 is 3.1) was obtained using the method described below.

With the exception of replacing the fluoropolyether in Example 1 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2CF_2O(CF_2CF_2CF_2O)_jCF_2CF_2CH_2OH$ (wherein the average polymerization degree represented by j is 3.1) (number average molecular weight: 800, molecular weight distribution: 1.1) (40.0 g), the same operations as Example 1 were conducted, yielding 13.6 g of the compound (A3).

$^1$H-NMR and $^{19}$F-NMR measurements of the obtained compound (A3) were conducted, and the structure was identified based on the following results.

$^1$H-NMR (acetone-$d_6$): δ [ppm]=1.58 to 1.82 (4H), 2.34 (2H), 3.38 to 4.25 (35H), 4.98 (1H), 5.08 (1H), 5.82 (1H)

$^{19}$F-NMR (acetone-$d_6$): δ [ppm]=−84.22 (12.4F), −86.40 (4F), −124.30 (4F), −130.08 (6.2F)

Example 81

A compound (A3) represented by the formula (A3) shown above (wherein within the formula (A3), the average polymerization degree represented by na3 is 6.2) was obtained using the method described below.

With the exception of replacing the fluoropolyether in Example 1 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2CF_2O(CF_2CF_2CF_2O)_jCF_2CF_2CH_2OH$ (wherein the average polymerization degree represented by j is 6.2) (number average molecular weight: 1,300, molecular weight distribution: 1.1) (40.0 g), the same operations as Example 1 were conducted, yielding 14.1 g of the compound (A3).

$^1$H-NMR and $^{19}$F-NMR measurements of the obtained compound (A3) were conducted, and the structure was identified based on the following results.

$^1$H-NMR (acetone-$d_6$): δ [ppm]=1.58 to 1.82 (4H), 2.34 (2H), 3.38 to 4.25 (35H), 4.98 (1H), 5.08 (10H), 5.82 (1H)

$^{19}$F-NMR (acetone-$d_6$): δ [ppm]=−84.22 (24.8F), −86.40 (4F), −124.30 (4F), −130.08 (12.4F)

Example 9

A compound (A3) represented by the formula (A3) shown above (wherein within the formula (A3), the average polymerization degree represented by na3 is 8) was obtained using the method described below.

With the exception of replacing the fluoropolyether in Example 1 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2CF_2O(CF_2CF_2CF_2O)_jCF_2CF_2CH_2OH$ (wherein the average polymerization degree represented by j is 8) (number average molecular weight: 1,600, molecular weight distribution: 1.1) (40.0 g), the same operations as Example 1 were conducted, yielding 11.1 g of the compound (A3).

$^1H$-NMR and $^{19}F$-NMR measurements of the obtained compound (A3) were conducted, and the structure was identified based on the following results.

$^1H$-NMR (acetone-$d_6$): δ [ppm]=1.58 to 1.82 (4H), 2.34 (2H), 3.38 to 4.25 (35H), 4.98 (1H), 5.08 (1H), 5.82 (1H)

$^{19}F$-NMR (acetone-$d_6$): δ [ppm]=−84.22 (32F), −86.40 (4F), −124.30 (4F), −130.08 (16F)

Example 10

A compound (B1) represented by the formula (B1) shown above (wherein within the formula (B1), the average polymerization degree represented by mb1 is 3.4, and the average polymerization degree represented by nb1 is 3.4) was obtained using the method described below.

First, a compound (15) represented by a formula (15) shown below was synthesized using the method described below. Specifically, 1,3-diallyloxy-2-propanol and 3,4-dihydro-2H-pyran were reacted to synthesize a compound represented by a formula (14) shown below. The double bond at one end of the obtained compound (14) was then oxidized using m-chloroperbenzoic acid, thus synthesizing the compound (15) represented by the formula (15) shown below.

[Chemical formula 16]

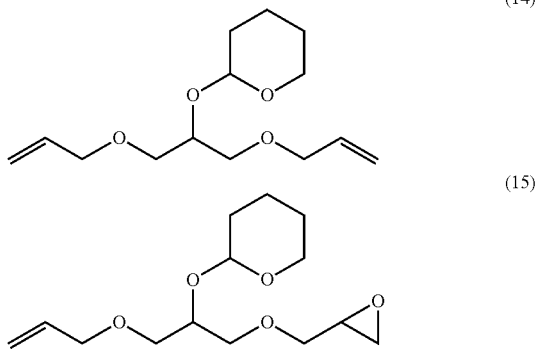

(14)

(15)

With the exception of replacing the compound (10) represented by the formula (10) used in Example 1, and instead using the compound (15) represented by the formula (15) (8.17 g), the same operations as Example 1 were conducted, yielding 16.7 g of the compound (B1).

$^1H$-NMR and $^{19}F$-NMR measurements of the obtained compound (B1) were conducted, and the structure was identified based on the following results.

$^1H$-NMR (acetone-$d_6$): δ [ppm]=1.75 (2H), 3.40 to 4.20 (35H), 5.10 (H), 5.25 (1H), 5.91 (1H)

$^{19}F$-NMR (acetone-$d_6$): δ [ppm]=−51.99 to −55.72 (6.8F), −78.48 (2F), −80.66 (2F), −89.16 to −91.14 (13.6F)

Example 11

A compound (B1) represented by the formula (B1) shown above (wherein within the formula (B1), the average polymerization degree represented by mb1 is 6.2, and the average polymerization degree represented by nb1 is 6.2) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2OH$ (wherein the average polymerization degree represented by g is 6.2, and the average polymerization degree represented by h is 6.2) (number average molecular weight: 1,300, molecular weight distribution: 1.1) (40.0 g), the same operations as Example 10 were conducted, yielding 16.2 g of the compound (B1).

$^1H$-NMR and $^{19}F$-NMR measurements of the obtained compound (B1) were conducted, and the structure was identified based on the following results.

$^1H$-NMR (acetone-$d_6$): δ [ppm]=1.75 (2H), 3.40 to 4.20 (35H), 5.10 (1H), 5.25 (1H), 5.91 (1H)

$^{19}F$-NMR (acetone-$d_6$): δ [ppm]=−51.99 to −55.72 (12.4F), −78.48 (2F), −80.66 (2F), −89.16 to −91.14 (24.8F)

Example 121

A compound (B1) represented by the formula (B1) shown above (wherein within the formula (B1), the average polymerization degree represented by mb1 is 7.8, and the average polymerization degree represented by nb1 is 7.8) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2OH$ (wherein the average polymerization degree represented by g is 7.8, and the average polymerization degree represented by h is 7.8) (number average molecular weight: 1,600, molecular weight distribution: 1.1) (40.0 g), the same operations as Example 10 were conducted, yielding 16.8 g of the compound (B1).

$^1H$-NMR and $^{19}F$-NMR measurements of the obtained compound (B1) were conducted, and the structure was identified based on the following results.

$^1H$-NMR (acetone-$d_6$): δ [ppm]=1.75 (2H), 3.40 to 4.20 (35H), 5.10 (H), 5.25 (1H), 5.91 (1H)

$^{19}F$-NMR (acetone-$d_6$): δ [ppm]=−51.99 to −55.72 (15.6F), −78.48 (2F), −80.66 (2F), −89.16 to −91.14 (31.2F)

Example 13

A compound (B2) represented by the formula (B2) shown above (wherein within the formula (B2), the average polymerization degree represented by nb2 is 5.4) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_iCF_2CH_2OH$ (wherein the average polymerization degree represented by i is 5.4) (number average molecular weight: 800, molecular weight distribution: 1.1) (40.0 g), the same operations as Example 10 were conducted, yielding 16.2 g of the compound (B2).

$^1$H-NMR and $^{19}$F-NMR measurements of the obtained compound (B2) were conducted, and the structure was identified based on the following results.

$^1$H-NMR (acetone-$d_6$): δ [ppm]=1.75 (2H), 3.42 to 4.24 (35H), 5.10 (1H), 5.25 (1H), 5.91 (1H)

$^{19}$F-NMR (acetone-$d_6$): δ [ppm]=−78.57 (4F), −88.92 to −89.57 (21.6F)

Example 14

A compound (B2) represented by the formula (B2) shown above (wherein within the formula (B2), the average polymerization degree represented by nb2 is 9.7) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_iCF_2CH_2OH$ (wherein the average polymerization degree represented by i is 9.7) (number average molecular weight: 1.300, molecular weight distribution: 1.1) (40.0 g), the same operations as Example 10 were conducted, yielding 16.1 g of the compound (B2).

$^1$H-NMR and $^{19}$F-NMR measurements of the obtained compound (B2) were conducted, and the structure was identified based on the following results.

$^1$H-NMR (acetone-$d_6$): δ [ppm]=1.75 (2H), 3.42 to 4.24 (35H), 5.10 (1H), 5.25 (1H), 5.91 (1H)

$^{19}$F-NMR (acetone-$d_6$): δ [ppm]=−78.57 (4F), −88.92 to −89.57 (38.8F)

Example 151

A compound (B2) represented by the formula (B2) shown above (wherein within the formula (B2), the average polymerization degree represented by nb2 is 12.3) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_iCF_2CH_2OH$ (wherein the average polymerization degree represented by i is 12.3) (number average molecular weight: 1,600, molecular weight distribution: 1.1) (40.0 g), the same operations as Example 10 were conducted, yielding 16.7 g of the compound (B2).

$^1$H-NMR and $^{19}$F-NMR measurements of the obtained compound (B2) were conducted, and the structure was identified based on the following results.

$^1$H-NMR (acetone-$d_6$): δ [ppm]=1.75 (2H), 3.42 to 4.24 (35H), 5.10 (1H), 5.25 (1H), 5.91 (1H)

$^{19}$F-NMR (acetone-$d_6$): δ [ppm]=−78.57 (4F), −88.92 to −89.57 (49.2F)

Example 161

A compound (B3) represented by the formula (B3) shown above (wherein within the formula (B3), the average polymerization degree represented by nb3 is 3.1) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2CF_2O(CF_2CF_2CF_2O)_jCF_2CF_2CH_2OH$ (wherein the average polymerization degree represented by j is 3.1) (number average molecular weight: 800, molecular weight distribution: 1.1) (40.0 g), the same operations as Example 10 were conducted, yielding 14.6 g of the compound (B3).

$^1$H-NMR and $^{19}$F-NMR measurements of the obtained compound (B3) were conducted, and the structure was identified based on the following results.

$^1$H-NMR (acetone-$d_6$): δ [ppm]=1.75 (2H), 3.38 to 4.19 (35H), 5.10 (1H), 5.25 (1H), 5.91 (1H)

$^{19}$F-NMR (acetone-$d_6$): δ [ppm]=−84.22 (12.4F), −86.40 (4F), −124.30 (4F), −130.08 (6.2F)

Example 17

A compound (B3) represented by the formula (B3) shown above (wherein within the formula (B3), the average polymerization degree represented by nb3 is 6.2) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2CF_2O(CF_2CF_2CF_2O)_jCF_2CF_2CH_2OH$ (wherein the average polymerization degree represented by j is 6.2) (number average molecular weight: 1.300, molecular weight distribution: 1.1) (40.0 g), the same operations as Example 10 were conducted, yielding 15.2 g of the compound (B3).

$^1$H-NMR and $^{19}$F-NMR measurements of the obtained compound (B3) were conducted, and the structure was identified based on the following results.

$^1$H-NMR (acetone-$d_6$): δ [ppm]=1.75 (2H), 3.38 to 4.19 (35H), 5.10 (1H), 5.25 (1H), 5.91 (1H)

$^{19}$F-NMR (acetone-$d_6$): δ [ppm]=−84.22 (24.8F), −86.40 (4F), −124.30 (4F), −130.08 (12.4F)

Example 18

A compound (B3) represented by the formula (B3) shown above (wherein within the formula (83), the average polymerization degree represented by nb3 is 8) was obtained using the method described below.

With the exception of replacing the fluoropolyether in Example 10 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2CF_2O(CF_2CF_2CF_2O)_jCF_2CF_2CH_2OH$ (wherein the average polymerization degree represented by j is 8)

(number average molecular weight: 1.600, molecular weight distribution: 1.1) (40.0 g), the same operations as Example 10 were conducted, yielding 12.5 g of the compound (B3).

$^1$H-NMR and $^{19}$F-NMR measurements of the obtained compound (63) were conducted, and the structure was identified based on the following results.

$^1$H-NMR (acetone-$d_6$): δ [ppm]=1.75 (2H), 3.38 to 4.19 (35H), 5.10 (1H), 5.25 (1H), 5.91 (1H)

$^{19}$F-NMR (acetone-$d_6$): δ [ppm]=−84.22 (32F), −86.40 (4F), −124.30 (4F), −130.08 (16F)

Example 19

A compound (C1) represented by the formula (C1) shown above (wherein within the formula (C1), the average polymerization degree represented by mc1 is 3.4, and the average polymerization degree represented by nc1 is 3.4) was obtained using the method described below.

First, a compound represented by a formula (16) shown below was synthesized using the method described below. Specifically, 2-(4-chlorobutoxy)tetrahydropyran was reacted with the compound (11) shown above in Example 1, and the double bond was then oxidized using m-chloroperbenzoic acid, thus synthesizing the compound (16) represented by the formula (16) shown below.

[Chemical formula 17]

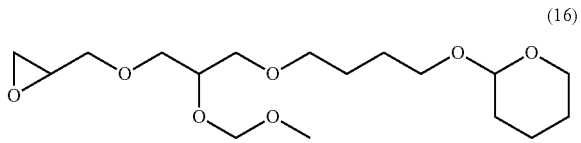

(16)

With the exception of replacing the compound (12) represented by the formula (12) used in Example 10, and instead using the compound (16) represented by the formula (16) (7.67 g), the same operations as Example 10 were conducted, yielding 16.9 g of the compound (C1).

$^1$H-NMR and $^{19}$F-NMR measurements of the obtained compound (C1) were conducted, and the structure was identified based on the following results.

$^1$H-NMR (acetone-$d_6$): δ [ppm]=1.68 to 1.75 (4H), 3.40 to 4.20 (35H), 5.10 (1H), 5.25 (1H), 5.91 (1H)

$^{19}$F-NMR (acetone-$d_6$): δ [ppm]=−51.99 to −55.72 (6.8F), −78.48 (2F), −80.66 (2F), −89.16 to −91.14 (13.6F)

Example 20

A compound (C1) represented by the formula (C1) shown above (wherein within the formula (C1), the average polymerization degree represented by mc1 is 7.8, and the average polymerization degree represented by nc1 is 7.8) was obtained using the method described below.

With the exception of replacing the fluoropolyether in Example 19 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2HO$ (wherein the average polymerization degree represented by g is 7.8, and the average polymerization degree represented by h is 7.8) (number average molecular weight: 1.600, molecular weight distribution: 1.1) (40.0 g), the same operations as Example 19 were conducted, yielding 16.5 g of the compound (C1).

$^1$H-NMR and $^{19}$F-NMR measurements of the obtained compound (C1) were conducted, and the structure was identified based on the following results.

$^1$H-NMR (acetone-$d_6$): δ [ppm]=1.68 to 1.75 (4H), 3.40 to 4.20 (35H), 5.10 (1H), 5.25 (1H), 5.91 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Example 21

A compound (D1) represented by the formula (D1) shown above (wherein within the formula (D1), the average polymerization degree represented by md1 is 3.4, and the average polymerization degree represented by nd1 is 3.4) was obtained using the method described below.

First, a compound (17) represented by a formula (17) shown below was synthesized using the method described below. Specifically, 2-(6-chlorohexyloxy)tetrahydropyran was reacted with the compound (11) shown above in Example 1, and the double bond was then oxidized using m-chloroperbenzoic acid, thus synthesizing the compound (17) represented by the formula (17) shown below.

[Chemical formula 18]

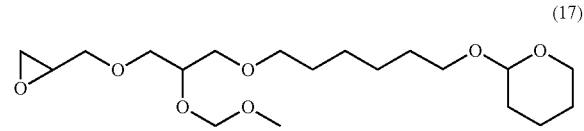

(17)

With the exception of replacing the compound (12) represented by the formula (12) used in Example 10, and instead using the compound (17) represented by the formula (7) (8.28 g), the same operations as Example 10 were conducted, yielding 17.3 g of the compound (D1).

$^1$H-NMR and $^{19}$F-NMR measurements of the obtained compound (D1) were conducted, and the structure was identified based on the following results.

$^1$H-NMR (acetone-$d_6$): δ [ppm]=1.46 to 1.62 (8H), 3.40 to 4.20 (35H), 5.10 (1H), 5.25 (1H), 5.91 (1H)

$^{19}$F-NMR (acetone-$d_6$): δ [ppm]=−51.99 to −55.72 (6.8F), −78.48 (2F), −80.66 (2F), −89.16 to −91.14 (13.6F)

Example 22

A compound (D1) represented by the formula (D1) shown above (wherein within the formula (D1), the average polymerization degree represented by md1 is 7.8, and the average polymerization degree represented by nd1 is 7.8) was obtained using the method described below.

With the exception of replacing the fluoropolyether in Example 21 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 21 were conducted, yielding 17.8 g of the compound (D).

¹H-NMR and ¹⁹F-NMR measurements of the obtained compound (D1)) were conducted, and the structure was identified based on the following results.

¹H-NMR (acetone-d₆): δ [ppm]=1.46 to 1.62 (8H), 3.40 to 4.20 (35H), 5.10 (1H), 5.25 (H), 5.91 (1H)

¹⁹F-NMR (acetone-d₆): δ [ppm]=−51.99 to −55.72 (15.6F), −78.48 (2F), −80.66 (2F), −89.16 to −91.14 (31.2F)

Example 23

A compound (E1) represented by the formula (E1) shown above (wherein within the formula (E1), the average polymerization degree represented by me1 is 3.4, and the average polymerization degree represented by ne1 is 3.4) was obtained using the method described below.

First, a compound (19) represented by a formula (19) shown below was synthesized using the method described below. Specifically, following reaction of epibromohydrin with 3-buten-1-ol, the epoxy group was hydrolyzed under acidic conditions to synthesize a compound (18) represented by a formula (18) shown below. Following protection of the primary hydroxyl group of the obtained compound (18) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (19) represented by the formula (19) shown below.

[Chemical formula 19]

(18)

(19)

With the exception of replacing the compound (10) represented by the formula (10) used in Example 1, and instead using the compound (19) represented by the formula (19) (7.39 g), the same operations as Example 1 were conducted, yielding 16.9 g of the compound (E1).

¹H-NMR and ¹⁹F-NMR measurements of the obtained compound (E1) were conducted, and the structure was identified based on the following results.

¹H-NMR (acetone-d₆): δ [ppm]=1.75 (2H), 2.34 (2H), 3.40 to 4.20 (35H), 4.98 (1H), 5.05 (1H), 5.82 (1H)

¹⁹F-NMR (acetone-d₆): δ [ppm]=−51.99 to −55.72 (6.8F), −78.48 (2F), −80.66 (2F), −89.16 to −91.14 (13.6F)

Example 24

A compound (E1) represented by the formula (E1) shown above (wherein within the formula (E1), the average polymerization degree represented by me1 is 7.8, and the average polymerization degree represented by ne1 is 7.8) was obtained using the method described below.

With the exception of replacing the fluoropolyether in Example 23 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 23 were conducted, yielding 15.7 g of the compound (E1).

¹H-NMR and ¹⁹F-NMR measurements of the obtained compound (E1) were conducted, and the structure was identified based on the following results.

¹H-NMR (acetone-d₆): δ [ppm]=1.75 (2H), 2.34 (2H), 3.40 to 4.20 (35H), 4.98 (1H), 5.05 (1H), 5.82 (1H)

¹⁹F-NMR (acetone-d₆): δ [ppm]=−51.99 to −55.72 (15.6F), −78.48 (2F), −80.66 (2F), −89.16 to −91.14 (31.2F)

Example 25

A compound (F1) represented by the formula (F1) shown above (wherein within the formula (F1), the average polymerization degree represented by mf1 is 3.4, and the average polymerization degree represented by nf1 is 3.4) was obtained using the method described below.

First, a compound (21) represented by a formula (21) shown below was synthesized using the method described below. Specifically, following reaction of epibromohydrin with 4-penten-1-ol, the epoxy group was hydrolyzed under acidic conditions to synthesize a compound (20) represented by a formula (20) shown below. Following protection of the primary hydroxyl group of the obtained compound (20) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (21) represented by the formula (21) shown below.

[Chemical formula 20]

(20)

(21)

With the exception of replacing the compound (10) represented by the formula (10) used in Example 1, and instead using the compound (21) represented by the formula (21) (7.81 g), the same operations as Example 1 were conducted, yielding 17.1 g of the compound (F1).

¹H-NMR and ¹⁹F-NMR measurements of the obtained compound (F1) were conducted, and the structure was identified based on the following results.

¹H-NMR (acetone-d₆): δ [ppm]=1.67 (2H), 1.75 (2H), 2.15 (2H), 3.40 to 4.20 (35H), 4.97 (1H), 5.03 (1H), 5.82 (1H)

¹⁹F-NMR (acetone-d₆): δ [ppm]=−51.99 to −55.72 (6.8F), −78.48 (2F), −80.66 (2F), −89.16 to −91.14 (13.6F)

Example 26

A compound (F1) represented by the formula (F1) shown above (wherein within the formula (F1), the average polymerization degree represented by mf1 is 7.8, and the average polymerization degree represented by nf1 is 7.8) was obtained using the method described below.

With the exception of replacing the fluoropolyether in Example 25 represented by $HOCH_2CF_2O(CF_2CF_2O)_g(CF_2)_nCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_nCF_2CH_2OH$ (wherein the average polymerization degree represented by g is 7.8, and the average polymerization degree represented by h is 7.8) (number average molecular weight: 1,600, molecular weight distribution: 1.1) (40.0 g), the same operations as Example 25 were conducted, yielding 17.7 g of the compound (F1).

$^1$H-NMR and $^{19}$F-NMR measurements of the obtained compound (F1) were conducted, and the structure was identified based on the following results.

$^1$H-NMR (acetone-$d_6$): δ [ppm]=1.67 (2H), 1.75 (2H), 2.15 (2H), 3.40 to 4.20 (35H), 4.97 (H), 5.03 (1H), 5.82 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Example 27

A compound (G1) represented by the formula (G1) shown above (wherein within the formula (G1), the average polymerization degree represented by mg1 is 3.4, and the average polymerization degree represented by ng1 is 3.4) was obtained using the method described below.

First, a compound (23) represented by a formula (23) shown below was synthesized using the method described below. Specifically, following reaction of epibromohydrin with propargyl alcohol, the epoxy group was hydrolyzed under acidic conditions to synthesize a compound (22) represented by a formula (22) shown below. Following protection of the primary hydroxyl group of the obtained compound (22) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (23) represented by the formula (23) shown below.

{Chemical formula 21]

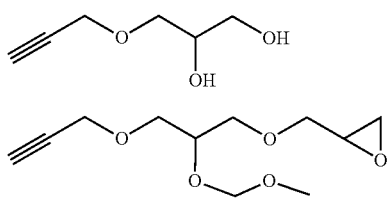

With the exception of replacing the compound (10) represented by the formula (10) used in Example 1, and instead using the compound (23) represented by the formula (23) (6.91 g), the same operations as Example 1 were conducted, yielding 16.7 g of the compound (G1).

$^1$H-NMR and $^{19}$F-NMR measurements of the obtained compound (G1) were conducted, and the structure was identified based on the following results.

$^1$H-NMR (acetone-$d_6$): δ [ppm]=1.75 (2H), 2.48 (1H), 3.40 to 4.20 (35H)

$^{19}$F-NMR (acetone-$d_6$): δ [ppm]=−51.99 to −55.72 (6.8F), −78.48 (2F), −80.66 (2F), −89.16 to −91.14 (13.6F)

Example 28

A compound (G1) represented by the formula (G1) shown above (wherein within the formula (G1), the average polymerization degree represented by mg1 is 7.8, and the average polymerization degree represented by ng1 is 7.8) was obtained using the method described below.

With the exception of replacing the fluoropolyether in Example 27 represented by $HOCH_2CF_2O(CF_2CF_2O)_g(CF_2O)_nCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_nCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 27 were conducted, yielding 16.2 g of the compound (G1).

$^1$H-NMR and $^{19}$F-NMR measurements of the obtained compound (G1) were conducted, and the structure was identified based on the following results.

$^1$H-NMR (acetone-$d_6$): δ [ppm]=1.75 (2H), 2.48 (1H), 3.40 to 4.20 (35H)

$^{19}$F-NMR (acetone-$d_6$): δ [ppm]=−51.99 to −55.72 (15.6F), −78.48 (2F), −80.66 (2F), −89.16 to −91.14 (31.2F)

Example 29

A compound (H1) represented by the formula (H1) shown above (wherein within the formula (H1), the average polymerization degree represented by mh1 is 3.4, and the average polymerization degree represented by nh1 is 3.4) was obtained using the method described below.

First, a compound (25) represented by a formula (25) shown below was synthesized using the method described below. Specifically, following reaction of epibromohydrin with 4-pentyn-1-ol, the epoxy group was hydrolyzed under acidic conditions to synthesize a compound (24) represented by a formula (24) shown below. Following protection of the primary hydroxyl group of the obtained compound (24) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (25) represented by the formula (25) shown below.

[Chemical formula 22]

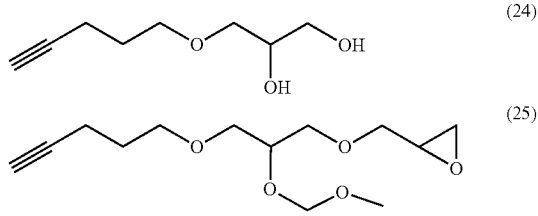

With the exception of replacing the compound (10) represented by the formula (10) used in Example 1, and instead using the compound (25) represented by the formula (25) (7.75 g), the same operations as Example 1 were conducted, yielding 17.1 g of the compound (H1).

$^1$H-NMR and $^{19}$F-NMR measurements of the obtained compound (H1) were conducted, and the structure was identified based on the following results.

$^1$H-NMR (acetone-$d_6$): δ [ppm]=1.75 to 1.78 (4H), 2.00 (1H), 2.30 (2H), 3.40 to 4.20 (35H)

$^{19}$F-NMR (acetone-$d_6$): δ [ppm]=−51.99 to −55.72 (6.8F), −78.48 (2F), −80.66 (2F), −89.16 to −91.14 (13.6F)

Example 30

A compound (H1) represented by the formula (H1) shown above (wherein within the formula (H1), the average polymerization degree represented by mh1 is 7.8, and the average polymerization degree represented by nh1 is 7.8) was obtained using the method described below.

With the exception of replacing the fluoropolyether in Example 29 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CFO(CF$_2$CF$_2$O)$_k$(CF$_2$O)$_h$CF$_2$CH$_2$OH (wherein the average polymerization degree represented by g is 7.8, and the average polymerization degree represented by h is 7.8) (number average molecular weight: 1.600, molecular weight distribution: 1.1) (40.0 g), the same operations as Example 29 were conducted, yielding 16.5 g of the compound (H1).

$^1$H-NMR and $^{19}$F-NMR measurements of the obtained compound (H1) were conducted, and the structure was identified based on the following results.

$^1$H-NMR (acetone-$d_6$): δ [ppm]=1.75 to 1.78 (4H), 2.00 (1H), 2.30 (2H), 3.40 to 4.20 (35H)

$^{19}$F-NMR (acetone-$d_6$): δ [ppm]=−51.99 to −55.72 (15.6F), −78.48 (2F), −80.66 (2F), −89.16 to −91.14 (31.2F)

Example 31

A compound (I1) represented by the formula (I1) shown above (wherein within the formula (I1), the average polymerization degree represented by mi1 is 3.4, and the average polymerization degree represented by ni1 is 3.4) was obtained using the method described below.

First, a compound (27) represented by a formula (27) shown below was synthesized using the method described below. Specifically, following reaction of epibromohydrin with 2-thiopheneethanol, the epoxy group was hydrolyzed under acidic conditions to synthesize a compound (26) represented by a formula (26) shown below. Following protection of the primary hydroxyl group of the obtained compound (26) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (27) represented by the formula (27) shown below.

[Chemical formula 23]

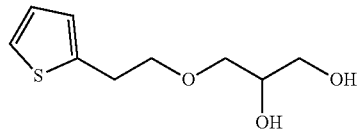

(26)

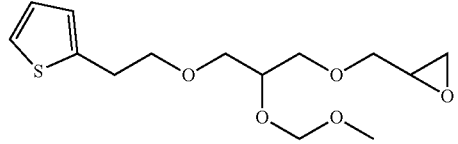

(27)

With the exception of replacing the compound (10) represented by the formula (10) used in Example 1, and instead using the compound (27) represented by the formula (27) (9.07 g), the same operations as Example 1 were conducted, yielding 17.7 g of the compound (11).

$^1$H-NMR and $^{19}$F-NMR measurements of the obtained compound (I1) were conducted, and the structure was identified based on the following results.

$^1$H-NMR (acetone-$d_6$): δ [ppm]=1.75 (2H), 3.07 (2H), 3.40 to 4.20 (35H), 6.90 (2H), 7.23 (1H)

$^{19}$F-NMR (acetone-$d_6$): δ [ppm]=−51.99 to −55.72 (6.8F), −78.48 (2F), −80.66 (2F), −89.16 to −91.14 (13.6F)

Example 32

A compound (I1) represented by the formula (I1) shown above (wherein within the formula (I1), the average polymerization degree represented by mi1 is 7.8, and the average polymerization degree represented by ni1 is 7.8) was obtained using the method described below.

With the exception of replacing the fluoropolyether in Example 31 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CF$_2$O(CF$_2$CF$_2$)$_g$(CF$_2$O)$_h$CF$_2$CH$_2$OH (wherein the average polymerization degree represented by g is 7.8, and the average polymerization degree represented by h is 7.8) (number average molecular weight: 1,600, molecular weight distribution: 1.1) (40.0 g), the same operations as Example 31 were conducted, yielding 15.4 g of the compound (11).

$^1$H-NMR and $^{19}$F-NMR measurements of the obtained compound (I1) were conducted, and the structure was identified based on the following results.

$^1$H-NMR (acetone-$d_6$): δ [ppm]=1.75 (2H), 3.07 (2H), 3.40 to 4.20 (35H), 6.90 (2H), 7.23 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Example 33

A compound (J1) represented by the formula (J1) shown above (wherein within the formula (J1), the average polymerization degree represented by mj1 is 3.4, and the average polymerization degree represented by nj1 is 3.4) was obtained using the method described below.

First, a compound (29) represented by a formula (29) shown below was synthesized using the method described below. Specifically, following reaction of epibromohydrin with 1-methylpyrazole-5-methanol, the epoxy group was hydrolyzed under acidic conditions to synthesize a compound (28) represented by a formula (28) shown below. Following protection of the primary hydroxyl group of the obtained compound (28) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (29) represented by the formula (29) shown below.

[Chemical formula 24]

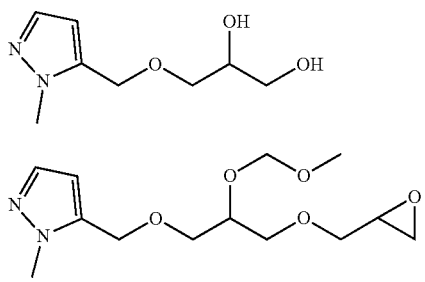

(28)

(29)

With the exception of replacing the compound (10) represented by the formula (10) used in Example 1, and instead using the compound (29) represented by the formula (29) (8.59 g), the same operations as Example 1 were conducted, yielding 17.5 g of the compound (J1).

$^1$H-NMR and $^{19}$F-NMR measurements of the obtained compound (J1) were conducted, and the structure was identified based on the following results.

$^1$H-NMR (acetone-$d_6$): δ [ppm]=1.75 (2H), 3.40 to 4.20 (38H), 6.20 (1H), 7.31 (1H)

$^{19}$F-NMR (acetone-$d_6$): δ [ppm]=−51.99 to −55.72 (6.8F), −78.48 (2F), −80.66 (2F), −89.16 to −91.14 (13.6F)

Example 34

A compound (J1) represented by the formula (J1) shown above (wherein within the formula (J1), the average polymerization degree represented by mj1 is 7.8, and the average polymerization degree represented by nj1 is 7.8) was obtained using the method described below.

With the exception of replacing the fluoropolyether in Example 33 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 33 were conducted, yielding 15.8 g of the compound (J1).

$^1$H-NMR and $^{19}$F-NMR measurements of the obtained compound (J1) were conducted, and the structure was identified based on the following results.

$^1$H-NMR (acetone-$d_6$): δ [ppm]=1.75 (2H), 3.40 to 4.20 (38H), 6.20 (1H), 7.31 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Example 35

A compound (K1) represented by the formula (K1) shown above (wherein within the formula (K1), the average polymerization degree represented by mk1 is 3.4, and the average polymerization degree represented by nk1 is 3.4) was obtained using the method described below.

First, a compound (30) represented by a formula (30) shown below was synthesized using the method described below. Specifically, following reaction of allyl glycidyl ether with 4-methoxyphenol, m-chloroperbenzoic acid was used to oxidize the double bond, thus synthesizing the compound (30) represented by the formula (30) shown below.

[Chemical formula 25]

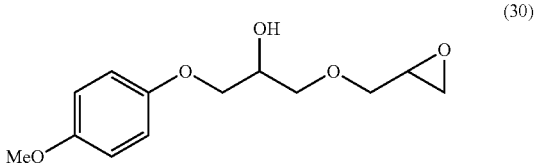

(30)

With the exception of replacing the compound (10) represented by the formula (10) used in Example 1, and instead using the compound (30) represented by the formula (30) (7.63 g), the same operations as Example 1 were conducted, yielding 17.7 g of the compound (K1).

$^1$H-NMR and $^{19}$F-NMR measurements of the obtained compound (K1) were conducted, and the structure was identified based on the following results.

$^1$H-NMR (acetone-$d_6$): δ [ppm]=1.75 (2H), 3.40 to 4.20 (36H), 6.85 (4H)

$^{19}$F-NMR (acetone-$d_6$): δ [ppm]=−51.99 to −55.72 (6.8F), −78.48 (2F), −80.66 (2F), −89.16 to −91.14 (13.6F)

Example 36

A compound (K1) represented by the formula (K1) shown above (wherein within the formula (K1), the average polymerization degree represented by mk1 is 7.8, and the average polymerization degree represented by nk1 is 7.8) was obtained using the method described below.

With the exception of replacing the fluoropolyether in Example 35 represented by $HOCH_2CF_2O(CF_2CF_2O)_g(CF_2O)_hCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_hCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 35 were conducted, yielding 16.1 g of the compound (K1).

$^1$H-NMR and $^{19}$F-NMR measurements of the obtained compound (K1) were conducted, and the structure was identified based on the following results.

$^1$H-NMR (acetone-$d_6$): δ [ppm]=1.75 (2H), 3.40 to 4.20 (36H), 6.85 (4H)

$^{19}$F-NMR (acetone-$d_6$): δ [ppm]=−51.99 to −55.72 (15.6F), −78.48 (2F), −80.66 (2F), −89.16 to −91.14 (31.2F)

Example 37

A compound (L1) represented by the formula (L1) shown above (wherein within the formula (L1), the average polymerization degree represented by ml1 is 3.4, and the average polymerization degree represented by nl1 is 3.4) was obtained using the method described below.

First, a compound (31) represented by a formula (31) shown below was synthesized using the method described below. Specifically, following reaction of allyl glycidyl ether with 3-cyanophenol, m-chloroperbenzoic acid was used to oxidize the double bond, thus synthesizing the compound (31) represented by the formula (31) shown below.

[Chemical formula 26]

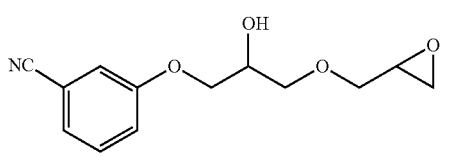

(31)

With the exception of replacing the compound (10) represented by the formula (10) used in Example 1, and instead using the compound (31) represented by the formula (31) (7.48 g), the same operations as Example 1 were conducted, yielding 17.6 g of the compound (L1).

$^1$H-NMR and $^{19}$F-NMR measurements of the obtained compound (L1) were conducted, and the structure was identified based on the following results.

$^1$H-NMR (acetone-$d_6$): δ [ppm]=1.75 (2H), 3.40 to 4.20 (33H), 7.28 to 7.34 (3H), 7.50 (1H)

$^{19}$F-NMR (acetone-$d_6$): δ [ppm]=−51.99 to −55.72 (6.8F), −78.48 (2F), −80.66 (2F), −89.16 to −91.14 (13.6F)

Example 38

A compound (L1) represented by the formula (L1) shown above (wherein within the formula (L1), the average polymerization degree represented by ml1 is 7.8, and the average polymerization degree represented by nl1 is 7.8) was obtained using the method described below.

With the exception of replacing the fluoropolyether in Example 37 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CF$_2$O(CF$_2$CF$_2$O)$_g$(CF$_2$O)$_h$CF$_2$CH$_2$OH (wherein the average polymerization degree represented by g is 7.8, and the average polymerization degree represented by h is 7.8) (number average molecular weight: 1.600, molecular weight distribution: 1.1) (40.0 g), the same operations as Example 37 were conducted, yielding 15.2 g of the compound (L1).

$^1$H-NMR and $^{19}$F-NMR measurements of the obtained compound (L1) were conducted, and the structure was identified based on the following results.

$^1$H-NMR (acetone-$d_6$): δ [ppm]=1.75 (2H), 3.40 to 4.20 (33H), 7.28 to 7.34 (3H), 7.50 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Example 39

A compound (M1) represented by the formula (M1) shown above (wherein within the formula (M1), the average polymerization degree represented by mm1 is 3.4, and the average polymerization degree represented by nm1 is 3.4) was obtained using the method described below.

First, a compound (33) represented by a formula (33) shown below was synthesized using the method described below. Specifically, following reaction of epibromohydrin with 3-cyanopropanoyl, the epoxy group was hydrolyzed under acidic conditions to synthesize a compound (32) represented by a formula (32) shown below.

Following protection of the primary hydroxyl group of the obtained compound (32) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (33) represented by the formula (33) shown below.

[Chemical formula 27]

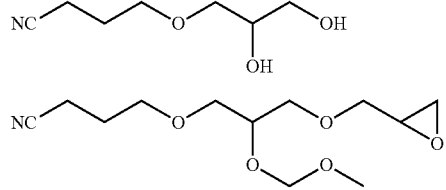

(32)

(33)

With the exception of replacing the compound (10) represented by the formula (10) used in Example 1, and instead using the compound (33) represented by the formula (33) (7.78 g), the same operations as Example 1 were conducted, yielding 17.1 g of the compound (M1).

$^1$H-NMR and $^{19}$F-NMR measurements of the obtained compound (M1) were conducted, and the structure was identified based on the following results.

$^1$H-NMR (acetone-$d_6$): δ [ppm]=1.75 (2H), 1.88 (2H), 2.54 (2H), 3.40 to 4.20 (35H)

$^{19}$F-NMR (acetone-$d_6$): δ [ppm]=−51.99 to −55.72 (6.8F), −78.48 (2F), −80.66 (2F), −89.16 to −91.14 (13.6F)

Example 40

A compound (M1) represented by the formula (M1) shown above (wherein within the formula (M1), the average polymerization degree represented by mm1 is 7.8, and the average polymerization degree represented by nm1 is 7.8) was obtained using the method described below.

With the exception of replacing the fluoropolyether in Example 39 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CFO(CF$_2$CF$_2$O)$_g$(CF$_2$O)$_h$CF$_2$CH$_2$OH (wherein the average polymerization degree represented by g is 7.8, and the average polymerization degree represented by h is 7.8) (number average molecular weight: 1.600, molecular weight distribution: 1.1) (40.0 g), the same operations as Example 39 were conducted, yielding 16.2 g of the compound (M1).

$^1$H-NMR and $^{19}$F-NMR measurements of the obtained compound (M1) were conducted, and the structure was identified based on the following results.

$^1$H-NMR (acetone-$d_6$): δ [ppm]=1.75 (2H), 1.88 (2H), 2.54 (2H), 3.40 to 4.20 (35H)

$^{19}$F-NMR (acetone-$d_6$): δ [ppm]=−51.99 to −55.72 (15.6F), −78.48 (2F), −80.66 (2F), −89.16 to −91.14 (31.2F)

Example 41

A compound (N1) represented by the formula (N1) shown above (wherein within the formula (N1), the average polymerization degree represented by mn1 is 3.4, and the average polymerization degree represented by nn1 is 3.4) was obtained using the method described below.

First, a compound (35) represented by a formula (35) shown below was synthesized using the method described below. Specifically, following reaction of epibromohydrin with 4-cyanobutanol, the epoxy group was hydrolyzed under acidic conditions to synthesize a compound (34) represented by a formula (34) shown below. Following protection of the primary hydroxyl group of the obtained compound (34) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (35) represented by the formula (35) shown below.

[Chemical formula 28]

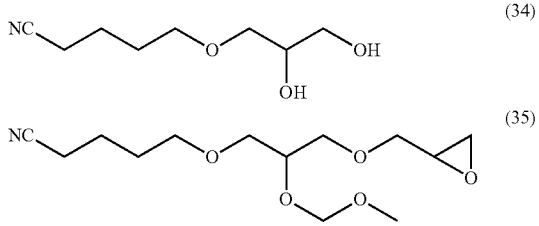

With the exception of replacing the compound (10) represented by the formula (10) used in Example 1, and instead using the compound (35) represented by the formula (35) (8.20 g), the same operations as Example 1 were conducted, yielding 17.3 g of the compound (N1).

$^1$H-NMR and $^{19}$F-NMR measurements of the obtained compound (N1) were conducted, and the structure was identified based on the following results.

$^1$H-NMR (acetone-$d_6$): δ [ppm]=1.75 (6H), 2.54 (2H), 3.40 to 4.20 (35H)

$^{19}$F-NMR (acetone-$d_6$): δ [ppm]=−51.99 to −55.72 (6.8F), −78.48 (2F), −80.66 (2F), −89.16 to −91.14 (13.6F)

Example 42

A compound (N1) represented by the formula (N1) shown above (wherein within the formula (N1), the average polymerization degree represented by mn1 is 7.8, and the average polymerization degree represented by nn1 is 7.8) was obtained using the method described below.

With the exception of replacing the fluoropolyether in Example 41 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CF$_2$O(CF$_2$CF$_2$O)$_g$(CF$_2$O)$_h$CF$_2$CH$_2$OH (wherein the average polymerization degree represented by g is 7.8, and the average polymerization degree represented by h is 7.8) (number average molecular weight: 1,600, molecular weight distribution: 1.1) (40.0 g), the same operations as Example 41 were conducted, yielding 15.4 g of the compound (N1).

$^1$H-NMR and $^{19}$F-NMR measurements of the obtained compound (N1) were conducted, and the structure was identified based on the following results.

$^1$H-NMR (acetone-$d_6$): δ [ppm]=1.75 (6H), 2.54 (2H), 3.40 to 4.20 (35H)

$^{19}$F-NMR (acetone-$d_6$): δ [ppm]=−51.99 to −55.72 (15.6F), −78.48 (2F), −80.66 (2F), −89.16 to −91.14 (31.2F)

Example 43

A compound (O1) represented by the formula (O1) shown above (wherein within the formula (O1), the average polymerization degree represented by mo1 is 3.4, and the average polymerization degree represented by no1 is 3.4) was obtained using the method described below.

First, a compound (36) represented by a formula (36) shown below was synthesized using the method described below. Specifically, following protection of the primary hydroxyl group of 3-methoxy-1,2-propanediol with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (36) represented by the formula (36) shown below.

[Chemical formula 29]

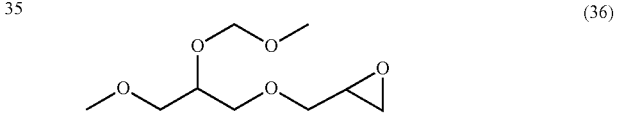

With the exception of replacing the compound (10) represented by the formula (10) used in Example 1, and instead using the compound (36) represented by the formula (36) (6.19 g), the same operations as Example 1 were conducted, yielding 16.4 g of the compound (O1).

$^1$H-NMR and $^{19}$F-NMR measurements of the obtained compound (O1) were conducted, and the structure was identified based on the following results.

$^1$H-NMR (acetone-$d_6$): δ [ppm]=1.75 (2H), 3.40 to 4.20 (36H)

$^{19}$F-NMR (acetone-$d_6$): δ [ppm]=−51.99 to −55.72 (6.8F), −78.48 (2F), −80.66 (2F), −89.16 to −91.14 (13.6F)

Example 44

A compound (O1) represented by the formula (O1) shown above (wherein within the formula (O1), the average polymerization degree represented by mo1 is 7.8, and the average polymerization degree represented by no1 is 7.8) was obtained using the method described below.

With the exception of replacing the fluoropolyether in Example 43 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CF$_2$O(CF$_2$CF$_2$O)$_g$(CF$_2$O)$_h$CF$_2$CH$_2$OH (wherein the average polymerization degree represented by g is 7.8, and the average polymerization degree represented by h is 7.8) (number average molecular weight: 1,600, molecular weight distribution: 1.1) (40.0 g), the same operations as Example 43 were conducted, yielding 16.1 g of the compound (O1).

$^1$H-NMR and $^{19}$F-NMR measurements of the obtained compound (O1) were conducted, and the structure was identified based on the following results.

$^1$H-NMR (acetone-d$_6$): δ [ppm]=1.75 (2H), 3.40 to 4.20 (36H)

$^{19}$F-NMR (acetone-d$_6$): δ [ppm]=−51.99 to −55.72 (15.6F), −78.48 (2F), −80.66 (2F), −89.16 to −91.14 (31.2F)

Example 45

A compound (P1) represented by the formula (P1) shown above (wherein within the formula (P1), the average polymerization degree represented by mp1 is 3.4, and the average polymerization degree represented by np1 is 3.4) was obtained using the method described below.

First, a compound (37) represented by a formula (37) shown below was synthesized using the method described below. Specifically, following reaction of the compound (11) described above in Example 1 with propyl bromide, m-chloroperbenzoic acid was used to oxidize the double bond, thus synthesizing the compound (37) represented by the formula (37) shown below.

[Chemical formula 30]

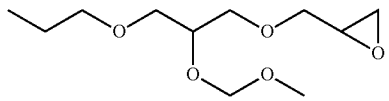

(37)

With the exception of replacing the compound (10) represented by the formula (10) used in Example 1, and instead using the compound (37) represented by the formula (37) (7.03 g), the same operations as Example 1 were conducted, yielding 16.8 g of the compound (P1).

$^1$H-NMR and $^{19}$F-NMR measurements of the obtained compound (P1) were conducted, and the structure was identified based on the following results.

$^1$H-NMR (acetone-d$_6$): δ [ppm]=0.84 (3H), 1.55 (2H), 1.75 (2H), 3.40 to 4.20 (35H)

$^{19}$F-NMR (acetone-d$_6$): δ [ppm]=−51.99 to −55.72 (6.8F), −78.48 (2F), −80.66 (2F), −89.16 to −91.14 (13.6F)

Example 46

A compound (P1) represented by the formula (P1) shown above (wherein within the formula (P1), the average polymerization degree represented by mp1 is 7.8, and the average polymerization degree represented by np1 is 7.8) was obtained using the method described below.

With the exception of replacing the fluoropolyether in Example 45 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CF$_2$O(CF$_2$CF$_2$O)$_g$(CF$_2$O)$_h$CF$_2$CH$_2$OH (wherein the average polymerization degree represented by g is 7.8, and the average polymerization degree represented by h is 7.8) (number average molecular weight: 1.600, molecular weight distribution: 1.1) (40.0 g), the same operations as Example 45 were conducted, yielding 14.4 g of the compound (P1).

$^1$H-NMR and $^{19}$F-NMR measurements of the obtained compound (P1) were conducted, and the structure was identified based on the following results.

$^1$H-NMR (acetone-d$_6$): δ [ppm]=0.84 (3H), 1.55 (2H), 1.75 (2H), 3.40 to 4.20 (35H)

$^{19}$F-NMR (acetone-d$_6$): δ [ppm]=−51.99 to −55.72 (15.6F), −78.48 (2F), −80.66 (2F), −89.16 to −91.14 (31.2F)

Example 47

A compound (Q1) represented by the formula (Q1) shown above (wherein within the formula (Q1), the average polymerization degree represented by mq1 is 3.4, and the average polymerization degree represented by nq1 is 3.4) was obtained using the method described below.

First, a compound (38) represented by a formula (38) shown below was synthesized using the method described below. Specifically, following reaction of 2,2,2-trifluoroethanol and allyl glycidyl ether, m-chloroperbenzoic acid was used to oxidize the double bond, thus synthesizing the compound (38) represented by the formula (38) shown below.

[Chemical formula 31]

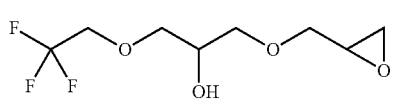

(38)

With the exception of replacing the compound (10) represented by the formula (10) used in Example 1, and instead using the compound (38) represented by the formula (38) (6.91 g), the same operations as Example 1 were conducted, yielding 17.3 g of the compound (Q1).

$^1$H-NMR and $^{19}$F-NMR measurements of the obtained compound (Q1) were conducted, and the structure was identified based on the following results.

$^1$H-NMR (acetone-d$_6$): δ [ppm]=1.75 (2H), 3.40 to 4.20 (35H)

$^{19}$F-NMR (acetone-d$_6$): δ [ppm]=−51.99 to −55.72 (6.8F), −75.22 (3F), −78.48 (2F), −80.66 (2F), −89.16 to −91.14 (13.6F)

Example 48

A compound (Q1) represented by the formula (Q1) shown above (wherein within the formula (Q1), the average polymerization degree represented by mq1 is 7.8, and the average polymerization degree represented by nq1 is 7.8) was obtained using the method described below.

With the exception of replacing the fluoropolyether in Example 47 represented by HOCH$_2$CF$_2$O(CF$_2$CF$_2$O)$_g$(CF$_2$O)$_h$CF$_2$CH$_2$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_2$CF$_2$O(CF$_2$CF$_2$O)$_g$(CF$_2$O)$_h$CF$_2$CH$_2$OH (wherein the average polymerization degree represented by g is 7.8, and the average polymerization degree represented by h is 7.8) (number average molecular weight: 1.600, molecular weight distribution: 1.1) (40.0 g), the same operations as Example 47 were conducted, yielding 16.3 g of the compound (Q1).

$^{1}$H-NMR and $^{19}$F-NMR measurements of the obtained compound (Q1) were conducted, and the structure was identified based on the following results.

$^{1}$H-NMR (acetone-d$_{6}$): δ [ppm]=1.75 (2H), 3.40 to 4.20 (35H)

$^{19}$F-NMR (acetone-d$_{6}$): δ [ppm]=−51.99 to −55.72 (15.6F), −75.22 (3F), −78.48 (2F), −80.66 (2F), −89.16 to −91.14 (31.2F)

Example 49

A compound (R1) represented by the formula (R1) shown above (wherein within the formula (R1), the average polymerization degree represented by mr1 is 3.4, and the average polymerization degree represented by nr1 is 3.4) was obtained using the method described below.

First, a compound (39) represented by a formula (39) shown below was synthesized using the method described below. Specifically, following reaction of 2,2,3,3,3-pentafluoro-1-propanol and allyl glycidyl ether, m-chloroperbenzoic acid was used to oxidize the double bond, thus synthesizing the compound (39) represented by the formula (39) shown below.

[Chemical formula 32]

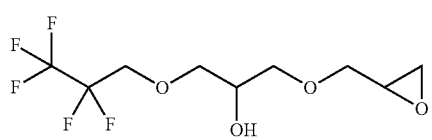

(39)

With the exception of replacing the compound (10) represented by the formula (10) used in Example 1, and instead using the compound (39) represented by the formula (39) (8.41 g), the same operations as Example 1 were conducted, yielding 18.0 g of the compound (R1).

$^{1}$H-NMR and $^{19}$F-NMR measurements of the obtained compound (R1) were conducted, and the structure was identified bused on the following results.

$^{1}$H-NMR (acetone-d$_{6}$): δ [ppm]=1.75 (2H), 3.40 to 4.20 (35H)

$^{19}$F-NMR (acetone-d$_{6}$): δ [ppm]=−51.99 to −55.72 (6.8F), −78.48 (2F), −80.66 (2F), −84.40 (3F), −89.16 to −91.14 (13.6F), −124.36 (2F)

Example 50

A compound (R1) represented by the formula (R1) shown above (wherein within the formula (R1), the average polymerization degree represented by mr1 is 7.8, and the average polymerization degree represented by nr1 is 7.8) was obtained using the method described below.

With the exception of replacing the fluoropolyether in Example 49 represented by HOCH$_{2}$CF$_{2}$O(CF$_{2}$CF$_{2}$O)$_{g}$(CF$_{2}$O)$_{h}$CF$_{2}$CH$_{2}$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_{2}$CF$_{2}$O(CF$_{2}$CF$_{2}$O)$_{g}$(CF$_{2}$O)$_{h}$CF$_{2}$CH$_{2}$OH (wherein the average polymerization degree represented by g is 7.8, and the average polymerization degree represented by h is 7.8) (number average molecular weight: 1.600, molecular weight distribution: 1.1) (40.0 g), the same operations as Example 49 were conducted, yielding 15.7 g of the compound (R1).

$^{1}$H-NMR and $^{19}$F-NMR measurements of the obtained compound (R1) were conducted, and the structure was identified based on the following results.

$^{1}$H-NMR (acetone-d$_{6}$): δ [ppm]=1.75 (2H), 3.40 to 4.20 (35H)

$^{19}$F-NMR (acetone-d$_{6}$): δ [ppm]=−51.99 to −55.72 (15.6F), −78.48 (2F), −80.66 (2F), −84.40 (3F), −89.16 to −91.14 (31.2F), −124.36 (2F)

Example 51

A compound (S1) represented by the formula (S1) shown above (wherein within the formula (S1), the average polymerization degree represented by ms1 is 3.4, and the average polymerization degree represented by ns1 is 3.4) was obtained using the method described below.

First, a compound (40) represented by a formula (40) shown below was synthesized using the method described below. Specifically, following reaction of the compound (11) described above in Example 1 with 2-bromoethyl methyl ether, m-chloroperbenzoic acid was used to oxidize the double bond, thus synthesizing the compound (40) represented by the formula (40) shown below.

[Chemical formula 33]

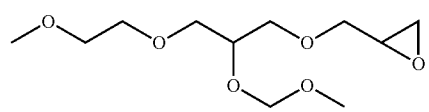

(40)

With the exception of replacing the compound (10) represented by the formula (10) used in Example 1, and instead using the compound (40) represented by the formula (40) (7.51 g), the same operations as Example 1 were conducted, yielding 17.6 g of the compound (S1).

$^{1}$H-NMR and $^{19}$F-NMR measurements of the obtained compound (S1) were conducted, and the structure was identified based on the following results.

$^{1}$H-NMR (acetone-d$_{6}$): δ [ppm]=1.75 (2H), 3.31 (3H), 3.40 to 4.20 (37H)

$^{19}$F-NMR (acetone-d$_{6}$): δ [ppm]=−51.99 to −55.72 (6.8F), −78.48 (2F), −80.66 (2F), −89.16 to −91.14 (13.6F)

Example 52

A compound (S1) represented by the formula (S1) shown above (wherein within the formula (S1), the average polymerization degree represented by ms1 is 7.8, and the average polymerization degree represented by ns1 is 7.8) was obtained using the method described below.

With the exception of replacing the fluoropolyether in Example 51 represented by HOCH$_{2}$CF$_{2}$O(CF$_{2}$CF$_{2}$O)$_{g}$(CF$_{2}$O)$_{h}$CF$_{2}$CH$_{2}$OH (wherein the average polymerization degree represented by g is 3.4, and the average polymerization degree represented by h is 3.4) (number average molecular weight: 800, molecular weight distribution: 1.1), and instead using a fluoropolyether represented by HOCH$_{2}$CF$_{2}$O(CF$_{2}$CF$_{2}$O)$_{g}$(CF$_{2}$O)$_{h}$CF$_{2}$CH$_{2}$OH (wherein the average polymerization degree represented by g is 7.8, and the average polymerization degree represented by h is 7.8) (number average molecular weight: 1.600, molecular weight distribution: 1.1) (40.0 g), the same operations as Example 51 were conducted, yielding 16.1 g of the compound (S1).

$^1$H-NMR and $^{19}$F-NMR measurements of the obtained compound (S1) were conducted, and the structure was identified based on the following results.

$^1$H-NMR (acetone-$d_6$): δ [ppm]=1.75 (2H), 3.31 (3H), 3.40 to 4.20 (37H)

$^{19}$F-NMR (acetone-$d_6$): δ [ppm]=−51.99 to −55.72 (15.6F), −78.48 (2F), −80.66 (2F), −89.16 to −91.14 (31.2F)

Example 53

A compound (T1) represented by the formula (T1) shown above (wherein within the formula (T1), the average polymerization degree represented by mt1 is 3.4, and the average polymerization degree represented by nt1 is 3.4) was obtained using the method described below.

First, a compound (42) represented by a formula (42) shown below was synthesized using the method described below. Specifically, following reaction of epibromohydrin with ethylene glycol monoallyl ether, the epoxy group was hydrolyzed under acidic conditions to synthesize a compound (41) represented by a formula (41) shown below. Following protection of the primary hydroxyl group of the obtained compound (41) with a t-butyldimethylsilyl group, the secondary hydroxyl group was protected with a methoxymethyl group, and the t-butyldimethylsilyl group was then removed from the resulting compound. Finally, epibromohydrin was reacted with the thus produced primary hydroxyl group, thus synthesizing the compound (42) represented by the formula (42) shown below.

[Chemical formula 34]

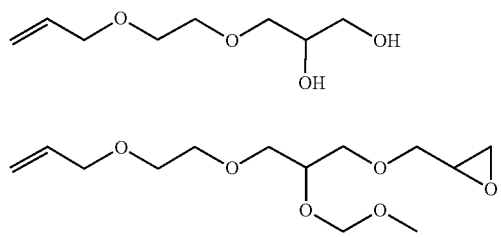

With the exception of replacing the compound (10) represented by the formula (10) used in Example 1, and instead using the compound (42) represented by the formula (42) (8.29 g), the same operations as Example 1 were conducted, yielding 17.3 g of the compound (T1).

$^1$H-NMR and $^{19}$F-NMR measurements of the obtained compound (TI) were conducted, and the structure was identified based on the following results.

$^1$H-NMR (acetone-$d_6$): δ [ppm]=1.75 (2H), 3.40 to 4.20 (39H), 5.10 (1H), 5.26 (1H), 5.91 (1H)

$^{19}$F-NMR (acetone-$d_6$): δ [ppm]=−51.99 to −55.72 (6.8F), −78.48 (21F), −80.66 (2F), −89.16 to −91.14 (13.6F)

Example 54

A compound (T1) represented by the formula (T1) shown above (wherein within the formula (T1), the average polymerization degree represented by mt1 is 7.8, and the average polymerization degree represented by nt1 is 7.8) was obtained using the method described below.

With the exception of replacing the fluoropolyether in Example 53 represented by $HOCH_2CF_2O(CF_2CF_2O)_g(CF_2O)_nCF_2CH_2OH$ (wherein the average polymerization degree represented by g is 3.4, and the average polymerization degree represented by h is 3.4) (number average molecular weight: 800, molecular weight distribution: 1.1), and instead using a fluoropolyether represented by $HOCH_2CF_2O(CF_2CF_2O)_g(CF_2O)_nCF_2CH_2OH$ (wherein the average polymerization degree represented by g is 7.8, and the average polymerization degree represented by h is 7.8) (number average molecular weight: 1.600, molecular weight distribution: 1.1) (40.0 g), the same operations as Example 53 were conducted, yielding 16.0 g of the compound (T1).

$^1$H-NMR and $^{19}$F-NMR measurements of the obtained compound (T1) were conducted, and the structure was identified based on the following results.

$^1$H-NMR (acetone-$d_6$): δ [ppm]=1.75 (2H), 3.40 to 4.20 (39H), 5.10 (1H), 5.26 (1H), 5.91 (1H)

$^{19}$F-NMR (acetone-$d_6$): δ [ppm]=−51.99 to −55.72 (15.6F), −78.48 (2F), −80.66 (2F), −89.16 to −91.14 (31.2F)

Comparative Examples 1 to 4

Compounds (AA) represented by a formula (AA) shown below were synthesized using the method disclosed in Patent Document 5.

[Chemical formula 35]

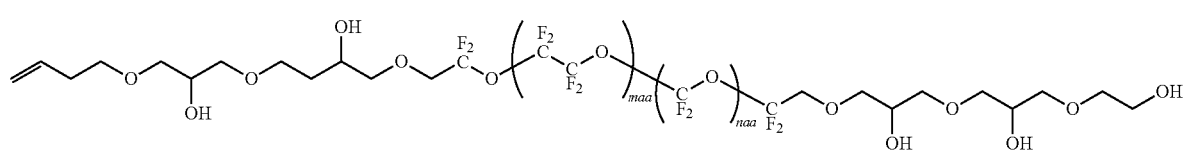

(In the formula (AA), the average polymerization degrees represented by maa and naa were 3.4 for both maa and naa in Comparative Example 1, were 6.2 for both maa and naa in Comparative Example 2, were 7.8 for both maa and naa in Comparative Example 3, and were 10 for both maa and naa in Comparative Example 4.)

Comparative Examples 5 to 8

Compounds (BB) represented by a formula (BB) shown below were synthesized using the method disclosed in Patent Document 4.

[Chemical formula 36]

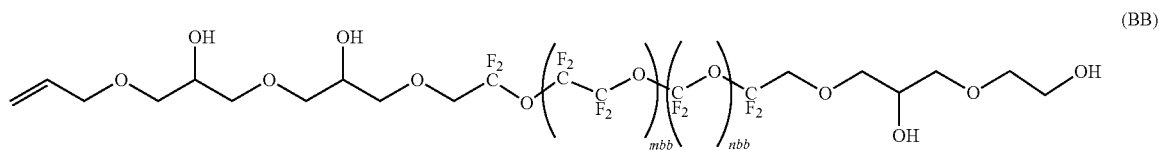

(BB)

(In the formula (BB), the average polymerization degrees represented by mbb and nbb were 3.4 for both mbb and nbb in Comparative Example 5, were 6.2 for both mbb and nbb in Comparative Example 6, were 7.8 for both mbb and nbb in Comparative Example 7, and were 10 for both mbb and nbb in Comparative Example 8.)

Comparative Example 9, Comparative Example 10

Compounds (CC) represented by a formula (CC) shown below were synthesized using the method disclosed in Patent Document 7.

[Chemical formula 37]

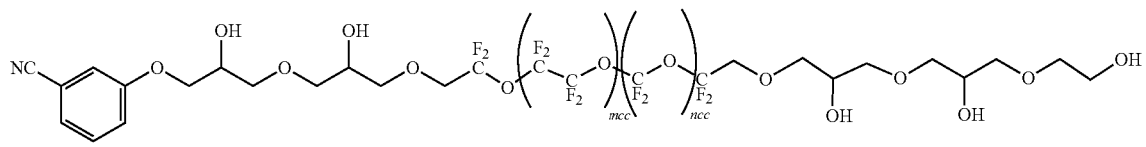

(CC)

(In the formula (CC), the average polymerization degrees represented by mcc and ncc were 3.4 for both mcc and ncc in Comparative Example 9, and were 7.8 for both mcc and ncc in Comparative Example 10.)

Comparative Example 11, Comparative Example 12

Compounds (DD) represented by a formula (DD) shown below were synthesized using the method disclosed in Patent Document 7.

[Chemical formula 38]

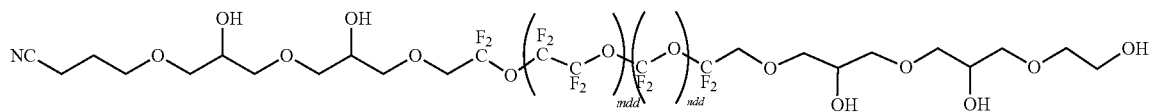

(DD)

(In the formula (DD), the average polymerization degrees represented by mdd and ndd were 3.4 for both mdd and ndd in Comparative Example 11, and were 7.8 for both mdd and ndd in Comparative Example 12.)

Comparative Example 13, Comparative Example 14

Compounds (EE) represented by a formula (EE) shown below were synthesized using the method disclosed in Patent Document 6.

[Chemical formula 39]

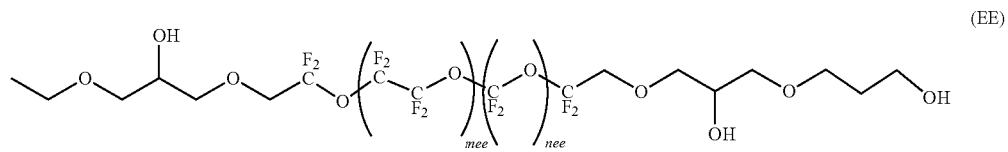

(EE)

(In the formula (EE), the average polymerization degrees represented by mee and nee were 3.4 for both mee and nee in Comparative Example 13, and were 7.8 for both mee and nee in Comparative Example 14.)

The structures for $R^1$ to $R^3$, $(O(CH_2)_b$, [A] and [B] when the compounds obtained in the above Examples 1 to 54 and Comparative Examples 1 to 14 were each applied to the formula (1) are shown below in Table 1.

TABLE 1

| Compound | $R^1$ | $(O(CH_2)_a)_b$ | | [A] | | [B] | | $R^2$ | $R^1$ |
|---|---|---|---|---|---|---|---|---|---|
| | | a | b | c | d | e | c + d | | f |
| (A1) | 3-butenyl group | — | 0 | 1 | 1 | 2 | 2 | (5) | 2 |
| (A2) | 3-butenyl group | — | 0 | 1 | 1 | 2 | 2 | (6) | 2 |
| (A3) | 3-butenyl group | — | 0 | 1 | 1 | 2 | 2 | (7) | 2 |
| (B1) | allyl group | — | 0 | 2 | 0 | — | 2 | (5) | 2 |
| (B2) | allyl group | — | 0 | 2 | 0 | — | 2 | (6) | 2 |
| (B3) | allyl group | — | 0 | 2 | 0 | — | 2 | (7) | 2 |
| (C1) | allyl group | — | 0 | 2 | 0 | — | 2 | (5) | 2 |
| (D1) | allyl group | — | 0 | 2 | 0 | — | 2 | (5) | 2 |
| (E1) | 3-butenyl group | — | 0 | 2 | 0 | — | 2 | (5) | 2 |
| (F1) | 4-pentenyl group | — | 0 | 2 | 0 | — | 2 | (5) | 2 |
| (G1) | propargyl group | — | 0 | 2 | 0 | — | 2 | (5) | 2 |
| (H1) | 4-pentynyl group | — | 0 | 2 | 0 | — | 2 | (5) | 2 |
| (I1) | thienylethyl group | — | 0 | 2 | 0 | — | 2 | (5) | 2 |
| (J1) | N-methylpyrazolylmethyl group | — | 0 | 2 | 0 | — | 2 | (5) | 2 |
| (K1) | methoxyphenyl group | — | 0 | 2 | 0 | — | 2 | (5) | 2 |
| (L1) | cyanophenyl group | — | 0 | 2 | 0 | — | 2 | (5) | 2 |
| (M1) | 3-cyanopropyl group | — | 0 | 2 | 0 | — | 2 | (5) | 2 |
| (N1) | 4-cyanobutyl group | — | 0 | 2 | 0 | — | 2 | (5) | 2 |
| (O1) | methyl group | — | 0 | 2 | 0 | — | 2 | (5) | 2 |
| (P1) | propyl group | — | 0 | 2 | 0 | — | 2 | (5) | 2 |
| (Q1) | 2.2.2-trifluoroethyl group | — | 0 | 2 | 0 | — | 2 | (5) | 2 |
| (R1) | 2.2.3.3.3-pentafluoropropyl group | — | 0 | 2 | 0 | — | 2 | (5) | 2 |
| (S1) | methyl group | 2 | 1 | 2 | 0 | — | 2 | (5) | 2 |
| (T1) | allyl group | 2 | 1 | 2 | 0 | — | 2 | (5) | 2 |
| (AA) | 3-butenyl group | — | 0 | 1 | 1 | 2 | 2 | (5) | 1 |
| (BB) | allyl group | — | 0 | 2 | 0 | — | 2 | (5) | *1 |
| (CC) | cyanophenyl group | — | 0 | 2 | 0 | — | 2 | (5) | 1 |
| (DD) | 3-cyanopropyl group | — | 0 | 2 | 0 | — | 2 | (5) | 1 |
| (EE) | ethyl group | — | 0 | 1 | 0 | — | 1 | (5) | *2 |

*1: Instead of $R^1$. —O—$CH_2$—CH(OH)—$CH_2$—O—$CH_2$—$CH_2$—OH
*2: Instead of $R^1$. —O—$CH_2$—CH(OH)—$CH_2$—O—$CH_2$—$CH_2$—$CH_2$—OH Next, using the method described below, the compounds obtained in Examples 1 to 54 and Comparative Examples 1 to 14 were each used to prepare a solution for forming a lubricant layer. Each of the obtained solutions for forming a lubricant layer was then used to form the lubricant layer of a magnetic recording medium in accordance with the method described below, thus obtaining magnetic recording media of Examples 1 to 54 and Comparative Examples 1 to 14.

[Solution for Forming Lubricant Layer]

Each of the compounds obtained in Examples 1 to 54 and Comparative Examples 1 to 14 was dissolved in the fluorine-based solvent Vertrel (a registered trademark) XF (a product name, manufactured by Mitsui DuPont Fluorochemicals Co., Ltd.), and the solution was then diluted with Vertrel XF so that application to a protective layer yielded a film thickness of 8.5 Å to 10 Å, thus completing preparation of a solution for forming a lubricant layer with a compound concentration of 0.001% by mass to 0.01% by mass.

[Magnetic Recording Medium]

A magnetic recording medium was prepared having an adhesive layer, a soft magnetic layer, a first base layer, a second base layer, a magnetic layer and a protective layer provided sequentially on a substrate having a diameter of 65 mm. The protective layer was formed from nitrogenated carbon. The solutions for forming a lubricant layer of Examples 1 to 54 and Comparative Examples 1 to 14 were each applied by a dipping method to the protective layer of a magnetic recording medium having each of the above layers up to and including the protective layer already formed.

Subsequently, the magnetic recording medium with the solution for forming a lubricant layer applied was subjected to a heat treatment by heating in a 120° C. thermostatic chamber for 10 minutes. This formed a lubricant layer on top of the protective layer, yielding a magnetic recording medium.

The magnetic recording media of Examples 1 to 54 and Comparative Examples 1 to 14 obtained in the manner described above were each evaluated by using the methods described below to measure the thickness of the lubricant layer, measure the adhesion (bond ratio) between the lubricant layer and the protective layer, and conduct a pickup characteristics test and a spin-off characteristics test. The results are shown in Tables 2 to 5.

[Measurement of Thickness of Lubricant Layer]

An FT-IR (product name: Nicolet iS50, manufactured by Thermo Fisher Scientific Inc.) was used to measure the peak height for the C—F stretching vibration of the lubricant layer. Using a correlation formula determined by the method outlined below, the film thickness of the lubricant layer was then calculated from the measured value for the peak height for the C—F stretching vibration of the lubricant layer.

[Method for Calculating Correlation Formula]

Lubricant layers having thicknesses of 6 to 20 Å (at intervals of 2 Å) were formed on the surfaces of disks having an adhesive layer, a soft magnetic layer, a first base layer, a second base layer, a magnetic layer and a protective layer provided sequentially on a substrate having a diameter of 65 mm.

Subsequently, for each of these disks with a lubricant layer formed thereon, an ellipsometer was used to measure the increase in film thickness from the surface of a disk on which no lubricant layer had been formed, thus determining the thickness of the lubricant layer. Further, FT-IR was also used to measure the peak height for the C—F stretching vibration for each of the disks having a lubricant layer formed thereon.

A correlation formula was then determined between the peak height obtained by FT-IR and the lubricant layer thickness measured using the ellipsometer.

[Measurement of Adhesion (Bond Ratio) Between Lubricant Layer and Protective Layer]

The magnetic recording medium having the lubricant layer formed thereon was cleaned by immersion for 10 minutes in the solvent Vertrel XF and subsequent removal from the solvent. The speed with which the magnetic recording medium was immersed in the solvent was 10 mm/sec, and the withdrawal speed was 1.2 mm/sec. Subsequently, the thickness of the lubricant layer was measured using the same method as that used for the lubricant layer thickness measurement conducted prior to the cleaning process.

The lubricant layer thickness prior to cleaning was deemed $\alpha$, the lubricant layer thickness following cleaning (following solvent immersion) was deemed $\beta$, and the bond ratio of the lubricant was calculated as the ratio between $\alpha$ and $\beta$ (($\beta/\alpha$)×100(%)). Using the calculated bond ratio, the adhesion between the lubricant layer and the protective layer was evaluated against the following evaluation criteria.

The bond ratio can be used as an indicator representing the bonding strength between the lubricant layer and the protective layer. If the adhesion between the lubricant layer and the protective layer is poor, then a portion of the fluorine-containing ether compound contained in the lubricant layer dissolves in the Vertrel XF and is washed away. As a result, the lubricant layer thickness following cleaning decreases, and the bond ratio falls.

[Evaluation Criteria for Adhesion (Bond Ratio)]

A: bond ratio of 75% or higher
B: bond ratio of 70% to 74%
C: bond ratio of 50% to 69%
D: bond ratio of 49% or less

[Pickup Characteristics Test]

The magnetic recording medium and a magnetic head were mounted on a spin stand, and the magnetic head was floated at a fixed point for 10 minutes under normal temperature and reduced pressure conditions (about 250 Torr). Subsequently, the surface of the magnetic head opposing the magnetic recording medium was analyzed using an ESCA (Electron Spectroscopy for Chemical Analysis) device. The intensity (signal intensity (a.u.)) of the peak derived from fluorine in the ESCA analysis indicates the amount of lubricant adhered to the magnetic head. Using the thus obtained signal intensity, the pickup characteristics were evaluated against the following evaluation criteria.

[Evaluation Criteria for Pickup Characteristics]

A: signal intensity of 160 or less (very little adhesion)
B: signal intensity of 161 to 300 (little adhesion)
C: signal intensity of 301 to 1,000 (high adhesion)
D: signal intensity of 1,001 or higher (very high adhesion)

[Spin-Off Characteristics Test]

The magnetic recording medium was mounted on a spin stand, and rotated at a rotational speed of 10,000 rpm for 72 hours in an environment at 80° C. The thickness of the lubricant layer at a position 20 mm radially from the center of the magnetic recording medium was measured by FT-IR before and after the rotation operation, and the reduction in the thickness of the lubricant layer from before to after the test was calculated. Using this calculated reduction in thickness, the spin-off characteristics were evaluated against the following evaluation criteria.

[Evaluation Criteria for Spin-Off Characteristics]

A: thickness reduction of 2% or less

B: thickness reduction of more than 2% but not more than 3%

C: thickness reduction of more than 3% but not more than 9%

D: thickness reduction of 10% or more

Based on these results, an overall evaluation was made using the following criteria.

[Overall Evaluation]

A: the evaluations of the bond ratio, the pickup characteristics and the spin-off characteristics were all A.

B: the evaluations of the bond ratio, the pickup characteristics and the spin-off characteristics were all either A or B, but at least one was B.

C: among the evaluations of the bond ratio, the pickup characteristics and the spin-off characteristics, at least one evaluation was C, but there were no D evaluations.

D: among the evaluations of the bond ratio, the pickup characteristics and the spin-off characteristics, at least one evaluation was D.

TABLE 2

| | Compound | Number average molecular weight PFPE portion | Number average molecular weight Total molecule | Film thickness (Å) | Bond ratio (%) | | Pickup characteristics Signal intensity (a.u.) | | Spin-off characteristics Thickness reduction (%) | | Overall evaluation |
|---|---|---|---|---|---|---|---|---|---|---|---|
| Example 1 | (A1) | 800 | 1223 | 9.0 | 81 | A | 121 | A | 1 | A | A |
| Example 2 | (A1) | 1300 | 1723 | 9.0 | 82 | A | 101 | A | 1 | A | A |
| Example 3 | (A1) | 1600 | 2023 | 9.0 | 82 | A | 69 | A | 0 | A | A |
| Example 4 | (A2) | 800 | 1223 | 9.0 | 79 | A | 113 | A | 1 | A | A |
| Example 5 | (A2) | 1300 | 1723 | 9.0 | 80 | A | 95 | A | 1 | A | A |
| Example 6 | (A2) | 1600 | 2023 | 9.0 | 78 | A | 61 | A | 0 | A | A |
| Example 7 | (A3) | 800 | 1223 | 9.0 | 77 | A | 110 | A | 2 | A | A |
| Example 8 | (A3) | 1300 | 1723 | 9.0 | 79 | A | 91 | A | 1 | A | A |
| Example 9 | (A3) | 1600 | 2023 | 9.0 | 78 | A | 57 | A | 0 | A | A |
| Example 10 | (B1) | 800 | 1194 | 9.0 | 82 | A | 117 | A | 1 | A | A |
| Example 11 | (B1) | 1300 | 1694 | 9.0 | 82 | A | 98 | A | 0 | A | A |
| Example 12 | (B1) | 1600 | 1994 | 9.0 | 83 | A | 63 | A | 0 | A | A |
| Example 13 | (B2) | 800 | 1194 | 9.0 | 80 | A | 111 | A | 1 | A | A |
| Example 14 | (B2) | 1300 | 1694 | 9.0 | 82 | A | 93 | A | 0 | A | A |
| Example 15 | (B2) | 1600 | 1994 | 9.0 | 79 | A | 59 | A | 0 | A | A |
| Example 16 | (B3) | 800 | 1194 | 9.0 | 78 | A | 106 | A | 2 | A | A |
| Example 17 | (B3) | 1300 | 1694 | 9.0 | 79 | A | 89 | A | 1 | A | A |
| Example 18 | (B3) | 1600 | 1994 | 9.0 | 79 | A | 54 | A | 0 | A | A |

TABLE 3

| | Compound | Number average molecular weight PFPE portion | Number average molecular weight Total molecule | Film thickness (Å) | Bond ratio (%) | | Pickup characteristics Signal intensity (a.u.) | | Spin-off characteristics Thickness reduction (%) | | Overall evaluation |
|---|---|---|---|---|---|---|---|---|---|---|---|
| Example 19 | (C1) | 800 | 1208 | 9.0 | 80 | A | 125 | A | 2 | A | A |
| Example 20 | (C1) | 1600 | 2008 | 9.0 | 79 | A | 71 | A | 0 | A | A |
| Example 21 | (D1) | 800 | 1237 | 9.0 | 78 | A | 141 | A | 2 | A | A |
| Example 22 | (D1) | 1600 | 2037 | 9.0 | 77 | A | 83 | A | 0 | A | A |
| Example 23 | (E1) | 800 | 1208 | 9.0 | 80 | A | 121 | A | 1 | A | A |
| Example 24 | (E1) | 1600 | 2008 | 9.0 | 78 | A | 69 | A | 0 | A | A |
| Example 25 | (E1) | 800 | 1223 | 9.0 | 79 | A | 132 | A | 2 | A | A |
| Example 26 | (F1) | 1600 | 2023 | 9.0 | 77 | A | 76 | A | 0 | A | A |
| Example 27 | (G1) | 800 | 1192 | 9.0 | 81 | A | 123 | A | 1 | A | A |
| Example 28 | (G1) | 1600 | 1992 | 9.0 | 82 | A | 74 | A | 0 | A | A |
| Example 29 | (H1) | 800 | 1221 | 9.0 | 80 | A | 135 | A | 1 | A | A |
| Example 30 | (H1) | 1600 | 2021 | 9.0 | 79 | A | 84 | A | 0 | A | A |
| Example 31 | (I1) | 800 | 1265 | 9.0 | 79 | A | 158 | A | 1 | A | A |
| Example 32 | (I1) | 1600 | 2065 | 9.0 | 78 | A | 92 | A | 0 | A | A |
| Example 33 | (J1) | 800 | 1249 | 9.0 | 83 | A | 123 | A | 1 | A | A |
| Example 34 | (J1) | 1600 | 2049 | 9.0 | 84 | A | 71 | A | 0 | A | A |
| Example 35 | (K1) | 800 | 1261 | 9.0 | 81 | A | 171 | B | 1 | A | B |
| Example 36 | (K1) | 1600 | 2061 | 9.0 | 80 | A | 101 | A | 0 | A | A |
| Example 37 | (L1) | 800 | 1256 | 9.0 | 85 | A | 126 | A | 0 | A | A |
| Example 38 | (L1) | 1600 | 2056 | 9.0 | 84 | A | 64 | A | 0 | A | A |

TABLE 4

| | Compound | Number average molecular weight PFPE portion | Number average molecular weight Total molecule | Film thickness (Å) | Bond ratio (%) | | Pickup characteristics Signal intensity (a.u.) | | Spin-off characteristics Thickness reduction (%) | | Overall evaluation |
|---|---|---|---|---|---|---|---|---|---|---|---|
| Example 39 | (M1) | 800 | 1221 | 9.0 | 81 | A | 156 | A | 1 | A | A |
| Example 40 | (M1) | 1600 | 2021 | 9.0 | 79 | A | 89 | A | 0 | A | A |
| Example 41 | (N1) | 800 | 1236 | 9.0 | 79 | A | 170 | B | 2 | A | B |
| Example 42 | (N1) | 1600 | 2036 | 9.0 | 79 | A | 98 | A | 0 | A | A |
| Example 43 | (O1) | 800 | 1168 | 9.0 | 76 | A | 201 | B | 0 | A | B |
| Example 44 | (O1) | 1600 | 1968 | 9.0 | 77 | A | 123 | A | 0 | A | A |
| Example 45 | (P1) | 800 | 1196 | 9.0 | 75 | A | 242 | B | 2 | A | B |
| Example 46 | (P1) | 1600 | 1996 | 9.0 | 74 | B | 159 | A | 0 | A | B |
| Example 47 | (Q1) | 800 | 1236 | 9.0 | 74 | B | 121 | A | 1 | A | B |
| Example 48 | (Q1) | 1600 | 2036 | 9.0 | 75 | A | 67 | A | 0 | A | A |
| Example 49 | (R1) | 800 | 1286 | 9.0 | 72 | B | 109 | A | 1 | A | B |
| Example 50 | (R1) | 1600 | 2086 | 9.0 | 73 | B | 57 | A | 0 | A | B |
| Example 51 | (S1) | 800 | 1257 | 9.0 | 70 | B | 273 | B | 3 | B | B |
| Example 52 | (S1) | 1600 | 2057 | 9.0 | 71 | B | 178 | B | 1 | B | B |
| Example 53 | (T1) | 800 | 1239 | 9.0 | 72 | B | 264 | B | 3 | B | B |
| Example 54 | (T1) | 1600 | 2039 | 9.0 | 71 | B | 159 | A | 1 | A | B |

TABLE 5

| | Compound | Number average molecular weight PFPE portion | Number average molecular weight Total molecule | Film thickness (Å) | Bond ratio (%) | | Pickup characteristics Signal intensity (a.u.) | | Spin-off characteristics Thickness reduction (%) | | Overall evaluation |
|---|---|---|---|---|---|---|---|---|---|---|---|
| Comparative Example 1 | (AA) | 800 | 1208 | 9.0 | 61 | C | 3034 | D | 26 | D | D |
| Comparative Example 2 | (AA) | 1300 | 1708 | 9.0 | 62 | C | 1521 | D | 18 | D | D |
| Comparative Example 3 | (AA) | 1600 | 2008 | 9.0 | 61 | C | 856 | C | 8 | C | C |
| Comparative Example 4 | (AA) | 2000 | 2408 | 9.0 | 61 | C | 385 | C | 3 | B | C |
| Comparative Example 5 | (BB) | 800 | 1106 | 9.0 | 56 | C | 3621 | D | 28 | D | D |
| Comparative Example 6 | (BB) | 1300 | 1606 | 9.0 | 55 | C | 1842 | D | 19 | D | D |
| Comparative Example 7 | (BB) | 1600 | 1906 | 9.0 | 56 | C | 979 | C | 9 | C | C |
| Comparative Example 8 | (BB) | 2000 | 2306 | 9.0 | 56 | C | 475 | C | 3 | B | C |
| Comparative Example 9 | (CC) | 800 | 1241 | 9.0 | 65 | C | 2756 | D | 21 | D | D |
| Comparative Example 10 | (CC) | 1600 | 2041 | 9.0 | 64 | C | 721 | C | 5 | C | C |
| Comparative Example 11 | (DD) | 800 | 1207 | 9.0 | 61 | C | 3256 | D | 24 | D | D |
| Comparative Example 12 | (DD) | 1600 | 2007 | 9.0 | 60 | C | 941 | C | 7 | C | C |
| Comparative Example 13 | (EE) | 800 | 1034 | 9.0 | 43 | D | 5982 | D | 36 | D | D |
| Comparative Example 14 | (EE) | 1600 | 1834 | 9.0 | 44 | D | 1984 | D | 14 | D | D |

As illustrated in Tables 2 to 5, the magnetic recording media of Examples 1 to 54 each used a fluorine-containing ether compound represented by the formula (1), and therefore exhibited a higher bond ratio and superior adhesion between the lubricant layer and the protective layer compared with the magnetic recording media of Comparative Examples 1 to 14.

Further, as illustrated in Tables 2 to 5, because the magnetic recording media of Examples 1 to 54 each used a fluorine-containing ether compound represented by the formula (1), the signal intensity derived from fluorine in the ESCA analysis was smaller than that observed in the Comparative Examples 1 to 14, clearly indicating that pickup was able to be suppressed.

Furthermore, as illustrated in Tables 2 to 5, because the magnetic recording media of Examples 1 to 54 each used a fluorine-containing ether compound represented by the formula (1), the thickness reduction was less than that observed for the magnetic recording medium of Comparative Examples 1 to 3, 5 to 7, and 9 to 14 which had similar number average molecular weights, clearly indicating that spin-off was able to be suppressed.

Among the magnetic recording media of Comparative Examples 1 to 14, comparison of those comparative examples that used the same fluorine-containing ether compound revealed that the pickup characteristics and spin-off characteristics deteriorated significantly as the number average molecular weight decreased.

In contrast, among the magnetic recording media of Examples 1 to 54, no marked deterioration in the pickup characteristics and spin-off characteristics was observed even when the number average molecular weight decreased.

In Comparative Examples 1 to 4, the evaluation tests were conducted using the compound (AA), in which f=1 in the group $R^3$ represented by the formula (4) within the formula (1). Since f=1 in the compound (AA), the structure stabilizes as a result of a regular alignment of five-membered ring-based intramolecular hydrogen bonding between the ether oxygen atom and the hydroxyl group within the formula (4), and a tendency for a deterioration in the adhesion (bond ratio) to the protective layer, and a deterioration in the pickup characteristics and spin-off characteristics was confirmed.

Further, comparison of Comparative Examples 1 and 2 with Comparative Examples 3 and 4, each of which used the compound (AA), confirmed that there was a tendency for the pickup characteristics and spin-off characteristics to deteriorate in Comparative Examples 1 and 2 in which the number average molecular weight was smaller.

In Comparative Examples 5 to 8, $R^3$ in the formula (1) has been replaced with —O—$CH_2$—CH(OH)—$CH_2$—O—$CH_2$—$CH_2$—OH, with one secondary hydroxyl group and one primary hydroxyl group. In other words, the number of secondary hydroxyl groups is less than that of $R^3$ in the formula (1) of the present invention. As a result, the adhesion to the protective layer deteriorates, and the fluorine-containing ether compound that exists in a state not adhered to the protective layer tends to aggregate, and becomes more likely to adhere to the magnetic head as foreign matter.

Further, comparison of Comparative Examples 5 and 6 with Comparative Examples 7 and 8, each of which used the compound (BB), confirmed that there was a tendency for the pickup characteristics and spin-off characteristics to deteriorate in Comparative Examples 5 and 6 in which the number average molecular weight was smaller.

In Comparative Examples 9 to 12, the evaluation tests were conducted using the compound (CC) and the compound (DD) in which f=1 in the group $R^3$ represented by the formula (4) within the formula (1). Since f=1 in the compound (CC) and the compound (DD), the structure stabilizes as a result of a regular alignment of five-membered ring-based intramolecular hydrogen bonding between the ether oxygen atom and the hydroxyl group within the formula (4), and a tendency for a deterioration in the adhesion (bond ratio) to the protective layer, and a deterioration in the pickup characteristics and spin-off characteristics was confirmed.

Further, comparison of Comparative Example 9 and Comparative Example 10, each of which used the compound (CC), confirmed that there was a tendency for the pickup characteristics and spin-off characteristics to deteriorate in Comparative Example 9 in which the number average molecular weight was smaller. Comparison of Comparative Example 11 and Comparative Example 12, each of which used the compound (DD), also confirmed that there was a tendency for the pickup characteristics and spin-off characteristics to deteriorate in Comparative Example 11 in which the number average molecular weight was smaller.

In Comparative Examples 13 and 14, the sum of c and d in the -[A]-[B]— structure within the formula (1) is 1, and $R^3$ in the formula (1) has been replaced with —O—$CH_2$—CH(OH)—$CH_2$—O—$CH_2$—$CH_2$—$CH_2$—OH, with one secondary hydroxyl group and one primary hydroxyl group. In other words, the compound (EE) was used, in which the number of secondary hydroxyl groups in both the -[A]-[B]— structure and in the $R^3$ structure is less than in the formula (1) of the present invention. As a result, a tendency for a deterioration in the adhesion to the protective layer, and a deterioration in the pickup characteristics and spin-off characteristics was confirmed.

Comparison of Examples 1 to 3 (compound (A1)) with Comparative Examples 1 to 4 (compound (AA)). Examples 37 and 38 (compound (L1)) with Comparative Examples 9 and 10 (compound (CC)), and Examples 39 and 40 (compound (M1)) with Comparative Examples 11 and 12 (compound (DD)) clearly indicated that by increasing by one the number of methylene carbons in the group $R^3$ in the fluorine-containing ether compound represented by the formula (1), the bond ratio could be improved dramatically, and the pickup characteristics and spin-off characteristics could be markedly improved.

It is thought that these results are due to the fact that the terminal primary hydroxyl group of the compound (AA), the compound (CC) and the compound (DD) are unable to participate effectively in bonding with the active sites on the protective layer, meaning satisfactory adhesion with the protective layer cannot be achieved. On the other hand, in the compound (A1), the compound (L1) and the compound (M1), it is thought that by increasing the number of methylene carbons in $R^3$, the five-membered ring-like regular alignment between the ether oxygen atom and the hydroxyl group within the molecule is disrupted, and intramolecular interactions of the hydroxyl groups are inhibited, and as a result, the adhesion to the protective layer was able to be dramatically improved.

INDUSTRIAL APPLICABILITY

The present invention provides a fluorine-containing ether compound that can be used favorably as a material for a magnetic recording medium lubricant that is capable of forming a lubricant layer that exhibits favorable adhesion to the protective layer and can suppress pickup and spin-off even when the molecular weight is reduced.

DESCRIPTION OF THE REFERENCE SIGNS

10: Magnetic recording medium
11: Substrate
12: Adhesive layer
13: Soft magnetic layer
14: First base layer
15: Second base layer
16: Magnetic layer
17: Protective layer
18: Lubricant layer

What is claimed is:

1. A fluorine-containing ether compound represented by a formula (1) shown below:

    (1)

wherein in the formula (1), $R^1$ is an alkyl group which may have a substituent, or an organic group having at least one double bond or triple bond, a represents an integer of 2 to 4, b represents 0 or 1, [A] is represented by a formula (2) shown below, wherein c in the formula (2) is 1 or 2, [B] is represented by a formula (3) shown below, wherein d in the formula (3) is 0 or 1, and e represents an integer of 2 to 4, provided that a sum of c in the formula (2) and d in the formula (3) is 2, $R^2$ is a perfluoropolyether chain, $R^3$ is represented by a formula (4) shown below, and f in the formula (4) represents an integer of 2 to 5.

[Chemical formula 1]

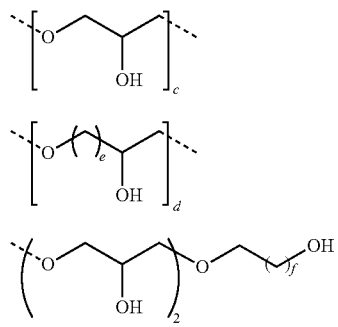

2. The fluorine-containing ether compound according to claim 1, wherein the fluorine-containing ether compound has a number average molecular weight within a range from 1,000 to 2,300.

3. The fluorine-containing ether compound according to claim 1, wherein $R^1$ in the formula (1) is an alkyl group of 1 to 6 carbon atoms.

4. The fluorine-containing ether compound according to claim 1,
wherein $R^1$ in the formula (1) is an alkyl group of 1 to 6 carbon atoms that has a substituent, and
the substituent is a fluoro group or a cyano group.

5. The fluorine-containing ether compound according to claim 1, wherein $R^1$ in the formula (1) is any one of an organic group of 6 to 12 carbon atoms containing an aromatic hydrocarbon, an organic group of 3 to 10 carbon atoms containing an aromatic heterocycle, an alkenyl group of 2 to 8 carbon atoms, and an alkynyl group of 3 to 8 carbon atoms.

6. The fluorine-containing ether compound according to claim 1, wherein $R^1$ in the formula (1) is one group selected from a group consisting of a methyl group, ethyl group, n-propyl group, isopropyl group, 2,2,2-trifluoroethyl group, 2,2,3,3,3-pentafluoropropyl group, 2,2,2,2,2-hexafluoroisopropyl group, 2-cyanoethyl group, 3-cyanopropyl group, 4-cyanobutyl group, phenyl group, methoxyphenyl group, cyanophenyl group, phenethyl group, thienylethyl group, N-methylpyrazolylmethyl group, allyl group, 3-butenyl group, 4-pentenyl group, propargyl group, 3-butynyl group, and 4-pentynyl group.

7. The fluorine-containing ether compound according to claim 1,
wherein $R^2$ in the formula (1) is represented by one of formula (5) to (8) shown below:

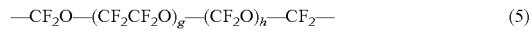    (5)

in the formula (5), g and h indicate average polymerization degrees, wherein g represents a number from 3 to 8, and h represents a number from 3 to 8,

    (6)

in the formula (6), i indicates an average polymerization degree, and represents a number from 5 to 13,

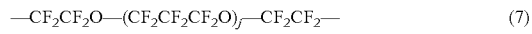    (7)

in the formula (7), j indicates an average polymerization degree, and represents a number from 3 to 8, and

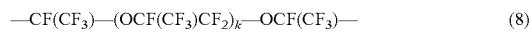    (8)

in the formula (8), k indicates an average polymerization degree, and represents a number from 3 to 8.

8. The fluorine-containing ether compound according to claim 1, wherein the compound represented by the formula (1) is a compound represented by one of formulas (A1) to (A3), (B1) to (B3), (L1) and (M1) shown below:

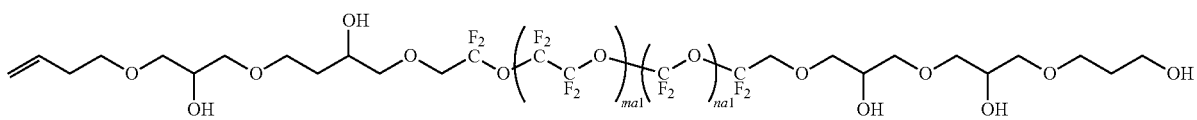

(A1)

-continued

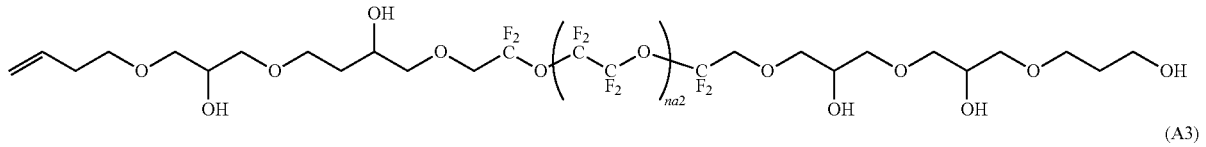
(A2)

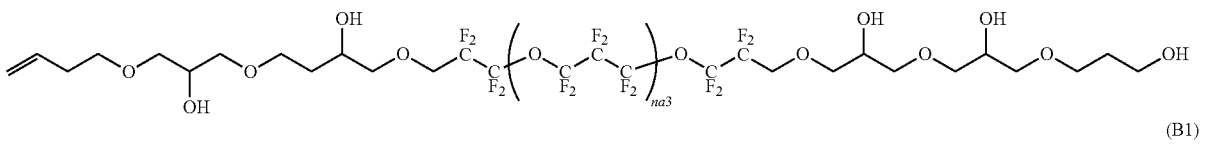
(A3)

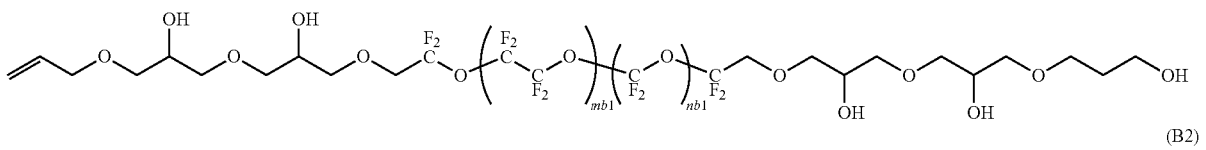
(B1)

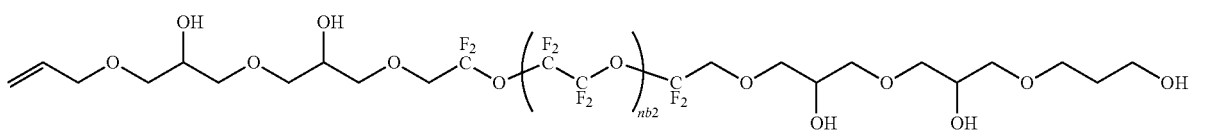
(B2)

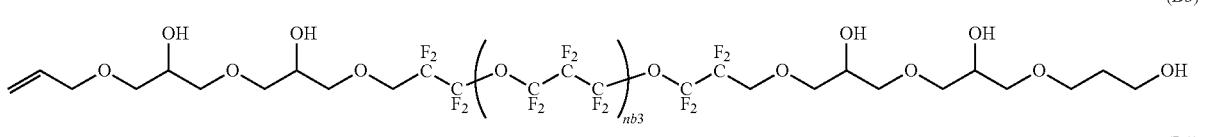
(B3)

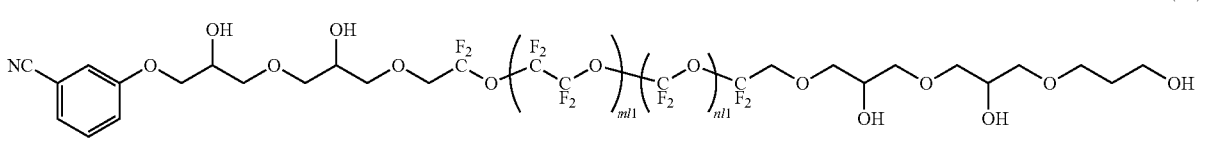
(L1)

(M1)

in the formula (A1), ma1 and na1 indicate average polymerization degrees, wherein ma1 represents a number from 3 to 8, and na1 represents a number from 3 to 8, in the formula (A2), na2 indicates an average polymerization degree, and represents a number from 5 to 13, in the formula (A3), na3 indicates an average polymerization degree, and represents a number from 3 to 8, in the formula (B1), mb1 and nb1 indicate average polymerization degrees, wherein mb1 represents a number from 3 to 8, and nb1 represents a number from 3 to 8, in the formula (B2), nb2 indicates an average polymerization degree, and represents a number from 5 to 13, in the formula (B3), nb3 indicates an average polymerization degree, and represents a number from 3 to 8, in the formula (L1), ml1 and nl1 indicate average polymerization degrees, wherein ml1 represents a number from 3 to 8, and nl1 represents a number from 3 to 8, and in the formula (M1), mm1 and nm1 indicate average polymerization degrees, wherein mm1 represents a number from 3 to 8, and nm1 represents a number from 3 to 8.

9. A lubricant for a magnetic recording medium, the lubricant comprising the fluorine-containing ether compound according to claim 1.

10. A magnetic recording medium comprising:
at least a magnetic layer, a protective layer and a lubricant layer provided sequentially on a substrate,
wherein the lubricant layer contains the fluorine-containing ether compound according to claim 1.

11. The magnetic recording medium according to claim 10, wherein an average thickness of the lubricant layer is within a range from 0.5 nm to 2.0 nm.

* * * * *